(12) United States Patent
Inoue et al.

(10) Patent No.: US 9,005,773 B2
(45) Date of Patent: Apr. 14, 2015

(54) ORGANOMETALLIC COMPLEX, LIGHT-EMITTING ELEMENT, DISPLAY DEVICE, ELECTRONIC DEVICE, AND LIGHTING DEVICE

(75) Inventors: Hideko Inoue, Kanagawa (JP); Tomoka Nakagawa, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 649 days.

(21) Appl. No.: 13/044,744

(22) Filed: Mar. 10, 2011

(65) Prior Publication Data

US 2011/0220882 A1 Sep. 15, 2011

(30) Foreign Application Priority Data

Mar. 15, 2010 (JP) ................................. 2010-058184

(51) Int. Cl.
| | | |
|---|---|---|
| H01L 51/54 | (2006.01) | |
| C09K 11/06 | (2006.01) | |
| C07F 15/00 | (2006.01) | |
| H01L 51/00 | (2006.01) | |
| H01L 51/50 | (2006.01) | |

(52) U.S. Cl.
CPC ........ *C07F 15/0033* (2013.01); *H01L 51/0085* (2013.01); *H01L 51/5016* (2013.01); *Y10S 428/917* (2013.01)

(58) Field of Classification Search
None
See application file for complete search history.

(56) References Cited

U.S. PATENT DOCUMENTS

| | | | |
|---|---|---|---|
| 7,915,415 | B2 | 3/2011 | Knowles et al. |
| 8,142,909 | B2 | 3/2012 | Beers et al. |
| 8,778,506 | B2 | 7/2014 | Ikemizu et al. |
| 2004/0124766 | A1 | 7/2004 | Nakagawa et al. |
| 2006/0036097 | A1 | 2/2006 | Qui et al. |
| 2007/0009759 | A1* | 1/2007 | Burn et al. ................... 428/690 |
| 2007/0085073 | A1 | 4/2007 | Inoue et al. |
| 2007/0190359 | A1 | 8/2007 | Knowles et al. |
| 2007/0196690 | A1 | 8/2007 | Ikemizu et al. |
| 2011/0073849 | A1 | 3/2011 | Knowles et al. |
| 2011/0101854 | A1* | 5/2011 | Inoue et al. ................... 313/504 |
| 2011/0187265 | A1 | 8/2011 | De Cola et al. |

FOREIGN PATENT DOCUMENTS

| | | |
|---|---|---|
| CN | 001919842 A | 2/2007 |
| EP | 1 777 229 A1 | 4/2007 |
| EP | 1 988 143 A1 | 11/2008 |
| EP | 1 988 144 A1 | 11/2008 |
| JP | 2007-137872 | 6/2007 |
| JP | 2007-208102 | 8/2007 |
| JP | 2008-69221 | 3/2008 |
| JP | 2008-074921 A | 4/2008 |
| JP | 2009-021336 A | 1/2009 |
| JP | 2012-046479 A | 3/2012 |
| WO | WO 2007/095118 A2 | 8/2007 |
| WO | WO 2007/097153 A1 | 8/2007 |
| WO | WO 2008/156879 A1 | 12/2008 |
| WO | WO 2009/107497 A1 | 9/2009 |
| WO | WO 2010/007107 A1 | 1/2010 |
| WO | WO 2011/052516 A1 | 5/2011 |

OTHER PUBLICATIONS

Van Diemen, J.H. et al., "Synthesis and Characterization of Orthometalated Rhodium (III) Complexes Containing Substituted Triazoles," Inorganic Chemistry, vol. 30, No. 21, 1991, pp. 4038-4043, American Chemical Society.
Zamora, F. et al., "Synthesis of Several Palladium Complexes Derived from 2,5-diphenyl-1,3,4-Oxadiazole. Reactivity Against Nucleobase Models,", Journal of Inorganic Biochemistry, vol. 68, No. 4, Dec. 1, 1997, pp. 257-263.
Baldo, M.A. et al., "Very High-Efficiency Green Organic Light-Emitting Devices Based on Electrophosphorescence," Applied Physics Letters, vol. 75, No. 1, Jul. 5, 1999, pp. 4-6.
Liu, J. et al., "Green-Yellow Electrophosphorescence from di [2,5-diphenyl-1,3,4-oxadiazole $C^{2'}$, $N^3$] Platinum (II ) Doped PVK Devices," Chinese Physics Letters, vol. 22, No. 3, pp. 2005, 723-726.
Wu, Z.L. et al., "Synthesis and Photoluminescence of a Novel Iridium Complex (BuPhOXD)2Ir(acac) with Unit of 1,3,4-Oxadiazole," Chinese Chemical Society, vol. 16, No. 2, 2005, pp. 241-244, (abstract only).
Chen, L. et al., "Synthesis, Structure, Electrochemistry, Photophysics and Electroluminescence of 1,3,4-Oxadiazole-Based Ortho-Metalated Iridium(III) Complexes,", Journal of Organometallic Chemistry, vol. 691, No. 16, Aug. 1, 2006, pp. 3519-3530.
European Search Report re Application No. EP 06021150.5, dated Jan. 29, 2007.
International Search Report re Application No. PCT/JP2010/068796, dated Nov. 30, 2010.
Written Opinion re Application No. PCT/JP2010/068796, dated Nov. 30, 2010.

* cited by examiner

*Primary Examiner* — Marie R. Yamnitzky
(74) *Attorney, Agent, or Firm* — Husch Blackwell LLP

(57) ABSTRACT

A novel substance exhibiting phosphorescence is provided. The novel substance is an organometallic complex represented by General Formula (G1). In General Formula (G1), $R^1$ represents a haloalkyl group having 1 to 9 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an arylene group having 6 to 13 carbon atoms which may have a substituent. M represents either a Group 9 element or a Group 10 element.

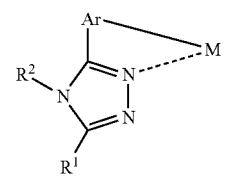

18 Claims, 20 Drawing Sheets

ORGANOMETALLIC COMPLEX, LIGHT-EMITTING ELEMENT, DISPLAY DEVICE, ELECTRONIC DEVICE, AND LIGHTING DEVICE

BACKGROUND OF THE INVENTION

1. Field of the Invention

The invention disclosed in this specification relates to substances that can emit light by electric current excitation. In particular, the invention relates to substances that can emit light from a triplet excited state. In addition, the invention relates to light-emitting elements, display devices, electronic devices, light-emitting devices, and lighting devices in each of which any of the aforementioned substances is used.

2. Description of the Related Art

A light-emitting element includes a layer (a light-emitting layer) containing a light-emitting substance between a pair of electrodes (an anode and a cathode). It has been reported that a variety of organic compounds can be used as the light-emitting substance.

It is said that light emission mechanism of a light-emitting element is as follows: when voltage is applied between a pair of electrodes with a light-emitting layer interposed therebetween, electrons injected from a cathode and holes injected from an anode are recombined in the light emission center of the light-emitting layer to form molecular excitons, and energy is released and light is emitted when the molecular excitons relax to a ground state. Singlet excitation and triplet excitation are known as excited states, and light emission can probably be achieved through either of the excited states.

In such a light-emitting element, since more excitons are generated in a triplet excited state than in a singlet excited state, emission efficiency of the light-emitting element can be increased by using a material that can emit light from a triplet excited state (a phosphorescent material). Therefore, numerous attempts to use a phosphorescent material as a light-emitting substance have been made.

A metal complex where iridium (Ir) is the central metal (hereinafter, referred to as an Ir complex) is a typical phosphorescent material which emits green to blue light (for example, see Patent Document 1). Disclosed in Patent Document 1 is an Ir complex where a triazole derivative is a ligand.

REFERENCE

Patent Document

[Patent Document 1] Japanese Published Patent Application No. 2007-137872

SUMMARY OF THE INVENTION

As reported in Patent Document 1, although phosphorescent materials emitting green to blue light have been developed, further development is required for obtaining phosphorescent materials that are better in reliability, light-emitting characteristics, cost, or the like.

In view of the above problems, an object of one embodiment of the present invention is to provide a novel substance that can exhibit phosphorescence. Another object is to provide a novel substance that exhibits phosphorescence in a wavelength band of green to blue. Another object is to provide a light-emitting element, a light-emitting device, a lighting device, or an electronic device in which the novel substance that can exhibit phosphorescence is used. Another object is to provide a light-emitting element, a light-emitting device, a lighting device, or an electronic device in which the novel substance that exhibits phosphorescence in a wavelength band of green to blue is used.

Note that the present invention is considered as acceptable as long as it can achieve at least one of the above plurality of objects.

The present inventors found that an ortho-metalated complex where a 3-aryl-4H-1,2,4-triazole derivative is a ligand exhibits phosphorescence in a wavelength band of green to blue.

One embodiment of the present invention is an organometallic complex including a structure represented by General Formula (G1).

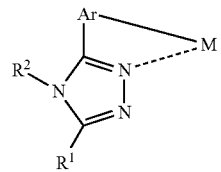

Another embodiment of the present invention is an organometallic complex represented by General Formula (G2).

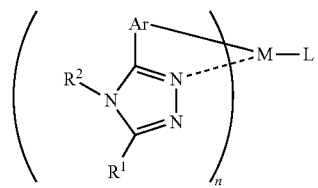

In General Formulas (G1) and (G2), $R^1$ represents a haloalkyl group having 1 to 9 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an arylene group having 6 to 13 carbon atoms which may have a substituent. M represents either a Group 9 element or a Group 10 element.

In General Formula (G2), when M is a Group 9 element, n is 2, and when M is a Group 10 element, n is 1. Moreover, L represents a monoanionic bidentate ligand.

Here, specific examples of a haloalkyl group having 1 to 9 carbon atoms which may have a substituent in $R^1$ include a fluoromethyl group, a trifluoromethyl group, a 1,1-difluoroethyl group, and a 1,1,2,2,3,3,3-heptafluoropropyl group, and a 1,1,2,2,3,3,4,4,5,5,6,6,7,7,8,8,9,9,9-nonadecafluorononyl group. In particular, a trifluoromethyl group is preferable.

Specific examples of an alkyl group having 1 to 6 carbon atoms in $R^2$ include a methyl group, an ethyl group, a propyl group, an isopropyl group, a butyl group, a sec-butyl group, an isobutyl group, a tert-butyl group, and a hexyl group. In addition, specific examples of a cycloalkyl group having 5 to 8 carbon atoms which may have a substituent in $R^2$ include a cyclopentyl group, a cyclohexyl group, a cycloheptyl group, a cyclooctyl group, a 1-methylcyclohexyl group, and a 2,6-dimethylcyclohexyl group. In addition, specific examples of an aryl group having 6 to 12 carbon atoms which may have a substituent in $R^2$ include a phenyl group, a biphenyl group, a phenyl group substituted by one or more methyl groups, a phenyl group substituted by one or more ethyl groups, a phenyl group substituted by one or more isopropyl groups, a phenyl group substituted by a tert-butyl group, a phenyl group substituted by a fluoro group, and a phenyl group substituted by a trifluoromethyl group.

Specific examples of Ar include a phenylene group, a phenylene group substituted by one or more alkyl groups, a phenylene group substituted by a cycloalkyl group, a phenylene group substituted by an alkoxy group, a phenylene group substituted by an aryloxy group, a phenylene group substituted by an alkylthio group, a phenylene group substituted by an arylthio group, a phenylene group substituted by a monoalkylamino group or a dialkylamino group, a phenylene group substituted by a monoarylamino group or a diarylamino group, a phenylene group substituted by an aryl group, a phenylene group substituted by one or more halogen groups, a phenylene group substituted by one or more haloalkyl groups, a biphenyl-diyl group, a naphthalene-diyl group, a fluorene-diyl group, a 9,9-dialkylfluorene-diyl group, and a 9,9-diarylfluorene-diyl group. Note that among these specific examples, when a substituent in which conjugation is extended from a benzene ring included in Ar is used as Ar (specifically, when a substituent having more than or equal to 10 carbon atoms is used as Ar) such as a biphenyl-diyl group, a naphthalene-diyl group, a fluorene-diyl group, a 9,9-dialkylfluorene-diyl group, or a 9,9-diarylfluorene-diyl group, an emission spectrum of the organometallic complex can be narrowed. When Ar is a phenylene group, electron spin in an excited spin state exists between Ar and a triazole ring; thus, when light is emitted, stretching vibration of carbon-carbon bonds of Ar and the triazole ring causes a local change. This is considered to be the reason why the second peak from the short wavelength side in a spectrum, which originates from the stretching vibration, is large. In contrast, when the conjugation in Ar is extended from the benzene ring, the electron in an excited spin state is not present between Ar and the triazole ring. Thus, the stretching vibration of carbon-carbon bonds of Ar and the triazole ring does not cause a local change, and the second peak becomes smaller. That is, the first peak on the shortest wavelength side in the emission spectrum becomes large. As a result, an emission wavelength of an organometallic complex can be shorter. In addition, an emission spectrum of the organometallic complex can be narrower.

Iridium and platinum are preferably used as the Group 9 element and the Group 10 element, respectively. This is because in terms of a heavy atom effect, a heavy metal is preferably used as a central metal of an organometallic complex in order to increase efficiency of phosphorescence.

A phenyl group and a phenylene group are preferably used in $R^2$ and Ar, respectively, in an organometallic complex including the structure represented by General Formula (G1) because synthesis is easy. That is, another embodiment of the present invention is an organometallic complex including a structure represented by General Formula (G3).

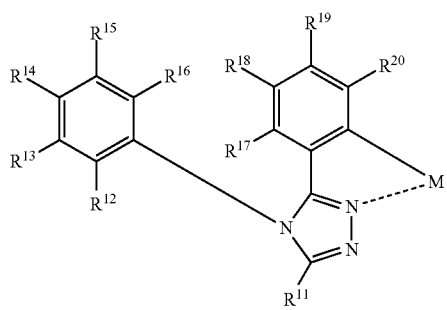

(G3)

A phenyl group and a phenylene group are preferably used in $R^2$ and Ar, respectively, in the organometallic complex represented by General Formula (G2) because synthesis is easy. That is, another embodiment of the present invention is an organometallic complex represented by General Formula (G4).

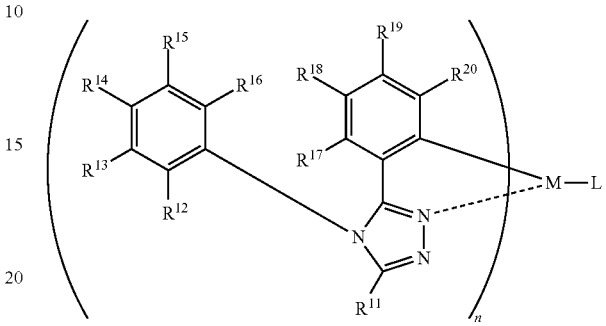

(G4)

In General Formulas (G3) and (G4), $R^{11}$ represents a haloalkyl group having 1 to 9 carbon atoms which may have a substituent. In addition, $R^{12}$ to $R^{16}$ individually represent any of hydrogen, an alkyl group having 1 to 6 carbon atoms, a cycloalkyl group having 5 to 8 carbon atoms, and a phenyl group. Further, $R^{17}$ to $R^{20}$ individually represent any of hydrogen, an alkyl group having 1 to 6 carbon atoms, a cycloalkyl group having 5 to 8 carbon atoms, an alkoxy group having 1 to 4 carbon atoms, an aryloxy group having 6 to 12 carbon atoms, an alkylthio group having 1 to 4 carbon atoms, an arylthio group having 6 to 12 carbon atoms, an alkylamino group having 1 to 4 carbon atoms, a monoarylamino or diarylamino group having 6 to 24 carbon atoms, a cyano group, a halogen group, a haloalkyl group having 1 to 4 carbon atoms, and an aryl group having 6 to 12 carbon atoms. Note that substituents that are adjacent to each other in $R^{17}$ to $R^{20}$ may be directly bonded to each other to form a ring structure. M represents either a Group 9 element or a Group 10 element.

In General Formula (G4), when M is a Group 9 element, n is 2, and when M is a Group 10 element, n is 1. Moreover, L represents a monoanionic bidentate ligand.

Note that specific examples of $R^{11}$ in General Formulas (G3) and (G4) can be the same as those of $R^1$ in General Formulas (G1) and (G2). In addition, specific examples of $R^{12}$ to $R^{16}$ include hydrogen, a methyl group, an ethyl group, an isopropyl group, a tert-butyl group, a hexyl group, a cyclohexyl group, and a phenyl group.

Specific examples of $R^{17}$ to $R^{20}$ individually include hydrogen, a methyl group, an ethyl group, an isopropyl group, a tert-butyl group, a hexyl group, a cyclohexyl group, a methoxy group, an ethoxy group, a propoxy group, an isopropoxy group, a phenoxy group, a methylthio group, a phenylthio group, a dimethylamino group, a diphenylamino group, a fluoro group, a fluoromethyl group, a difluoromethyl group, a trifluoromethyl group, a chloromethyl group, a dichloromethyl group, a bromomethyl group, a 2,2,2-trifluoroethyl group, a 3,3,3-trifluoropropyl group, a 1,1,1,3,3,3-hexafluoroisopropyl group, a phenyl group, a phenyl group substituted by a fluoro group, and a phenyl group substituted by a trifluoromethyl group.

Note that at least one of $R^{17}$ to $R^{20}$ is preferably an electron-withdrawing group. Examples of the electron-withdrawing group include a halogen group, a haloalkyl group, a phenyl group substituted by a halogen group, and a phenyl group substituted by a haloalkyl group. More specific examples include a cyano group, a fluoro group, a trifluoromethyl group, a phenyl group substituted by a fluoro group, a phenyl group substituted by a trifluoromethyl group; in particular, a fluoro group and a trifluoromethyl group are preferable. Since at least one of $R^{17}$ to $R^{20}$ is an electron-withdrawing group, the HOMO level of an organometallic complex is decreased, and an energy gap is increased accordingly; thus, the energy of the organometallic complex is stabilized. As a result, the emission wavelength of the organometallic complex can be shorter. For that reason, an organometallic complex having an electron-withdrawing group is especially preferable as a material that exhibits phosphorescence in a wavelength band of blue. In the case where $R^{17}$ and/or $R^{19}$ in General Formulas (G3) and (G4) are substituted by an alkoxy group such as a methoxy group, an ethoxy group, a propoxy group, or an isopropoxy group, the alkoxy group can function as the electron-withdrawing group.

Another embodiment of the present invention is an organometallic complex where the above monoanionic bidentate ligand is any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen.

Another embodiment of the present invention is an organometallic complex where the above monoanionic bidentate ligand is a ligand represented by any of Structural Formulas (L1) to (L6).

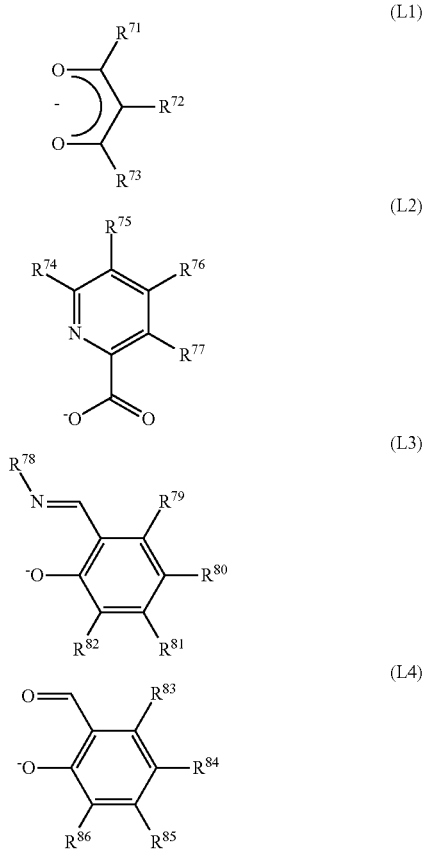

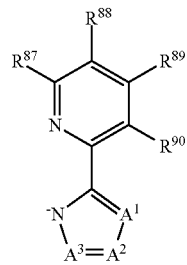

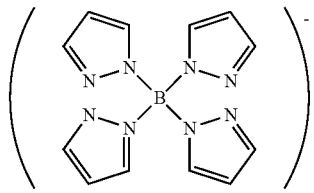

In Structural Formulas (L1) to (L6), $R^{71}$ to $R^{90}$ represent any of hydrogen, an alkyl group having 1 to 4 carbon atoms, a halogen group, a haloalkyl group, an alkoxy group having 1 to 4 carbon atoms, and an alkylthio group having 1 to 4 carbon atoms. In addition, $A^1$, $A^2$, and $A^3$ represent nitrogen N or carbon C—R. R represents hydrogen, an alkyl group having 1 to 4 carbon atoms, a halogen group, a haloalkyl group having 1 to 4 carbon atoms, or a phenyl group.

Another embodiment of the present invention is a light-emitting element including a layer containing any of the organometallic complexes between a pair of electrodes. The layer containing the organometallic complex may be a light-emitting layer.

Another embodiment of the present invention is a light-emitting element including, between a pair of electrodes, a first light-emitting unit containing any of the organometallic complexes and a second light-emitting unit containing a light-emitting material that emits light with a longer wavelength than the organometallic complex.

Another embodiment of the present invention is a light-emitting element including, between a pair of electrodes, a first light-emitting unit containing any of the organometallic complexes, a second light-emitting unit containing a first light-emitting material that emits light with a longer wavelength than the organometallic complex, and a third light-emitting unit containing a second light-emitting material that emits light with a longer wavelength than the organometallic complex and a shorter wavelength than the first light-emitting material.

Another embodiment of the present invention is a display device including any of the light-emitting elements in a pixel portion.

Another embodiment of the present invention is an electronic device including the display device in a display portion.

Another embodiment of the present invention is a lighting device including any of the light-emitting elements as a light source.

In one embodiment of the present invention, a haloalkyl group having 1 to 9 carbon atoms, a cycloalkyl group having 5 to 8 carbon atoms, an aryl group having 6 to 12 carbon atoms, and an arylene group having 6 to 13 carbon atoms each may have a substituent or may not have a substituent. When a substituent is included, carbon atoms contained in the substituent are not counted as the carbon atoms described above.

For example, a cycloalkyl group having a substituent has 5 or more and 8 or less carbon atoms except for carbon contained in the substituent.

In this specification, "a light-emitting device" means general devices each having a light-emitting element; specifically, it includes in its category a backlight used in a display device such as a television or a mobile phone, a traffic light, a lighting application such as a streetlight or illuminations on the street, a lighting device, lighting for breeding that can be used in a plastic greenhouse, and the like.

With one embodiment of the present invention, it is possible to provide a novel substance that can exhibit phosphorescence. It is also possible to provide a light-emitting element, a display device, a light-emitting device, a lighting device, and an electronic device including the novel substance.

DETAILED DESCRIPTION OF THE INVENTION

Figure 1A:
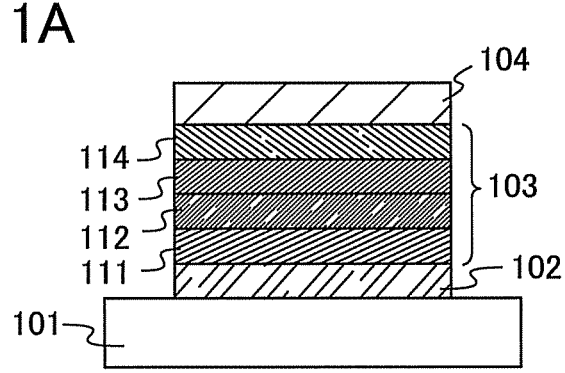
FIGS. 1A and 1B are conceptual diagrams of a light-emitting element according to one embodiment of the present invention.

Embodiments and examples of the present invention will be described in detail with reference to the accompanying drawings. Note that the present invention is not limited to the description below, and it is easily understood by those skilled in the art that modes and details can be modified in various ways without departing from the purpose and the scope of the present invention. Therefore, in the embodiments and examples of the present invention which will be described below, the same portions are commonly denoted by the same reference numerals in different drawings.

Besides, each of the embodiments and examples described below can be implemented in appropriate combination with any of the other embodiments and examples which are described in this specification unless otherwise mentioned.

Embodiment 1

One embodiment of the present invention is an organometallic complex including a structure represented by General Formula (G1).

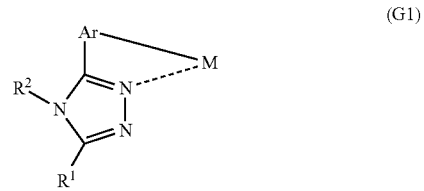

(G1)

In General Formula (G1), $R^1$ represents a haloalkyl group having 1 to 9 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an arylene group having 6 to 13 carbon atoms which may have a substituent. M represents either a Group 9 element or a Group 10 element.

Specific examples of organometallic complexes having the structure represented by General Formula (G1) can be organometallic complexes represented by Structural Formulas (100) to (178). Note that the present invention is not limited to the organometallic complexes represented by these structural formulas.

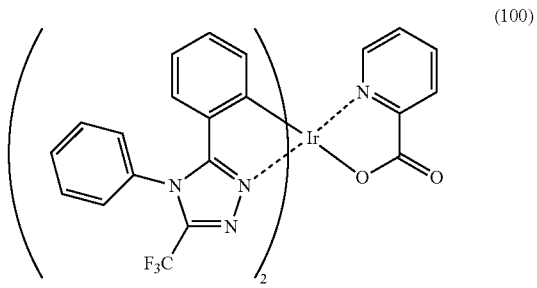

(100)

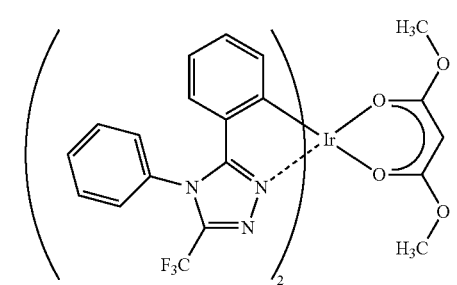 (101)
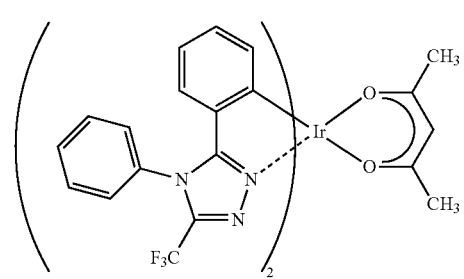 (102)
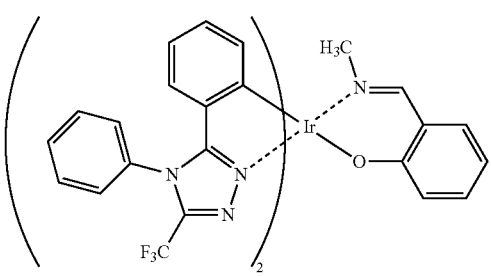 (103)
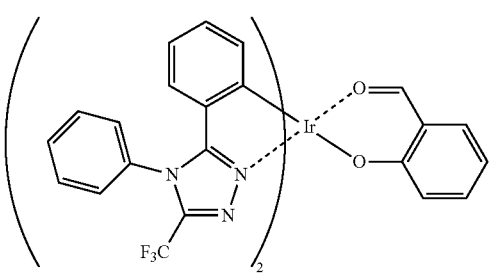 (104)
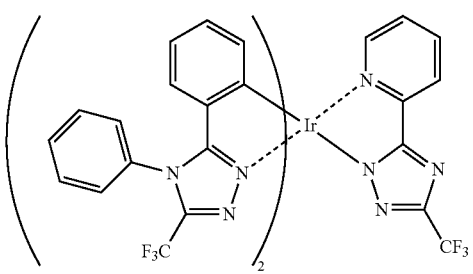 (105)
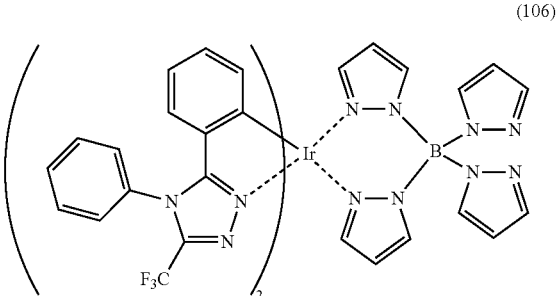 (106)
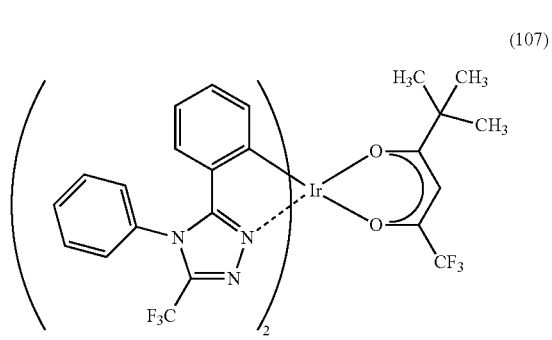 (107)
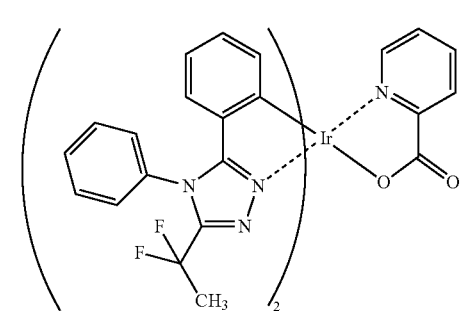 (108)
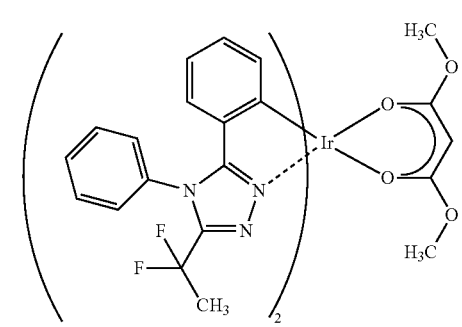 (109)
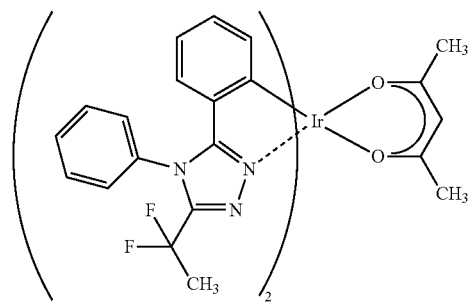 (110)

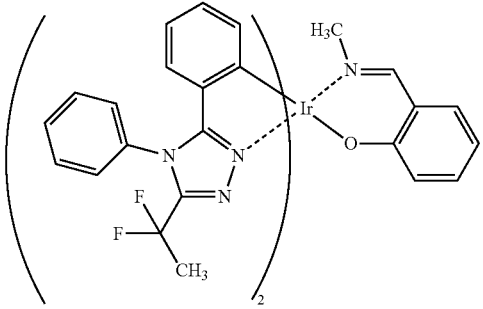
(111)
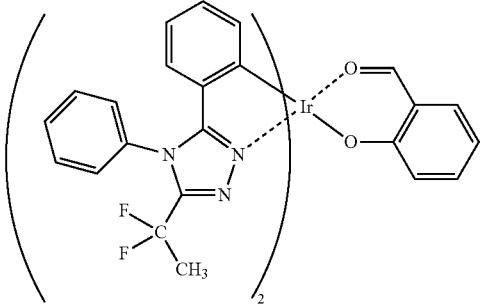
(112)
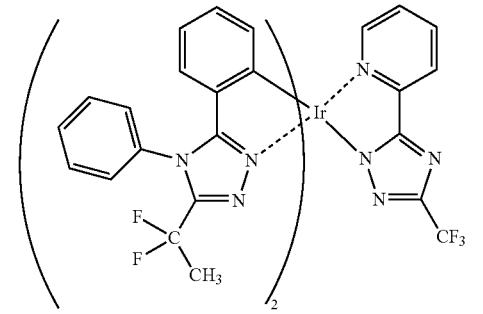
(113)
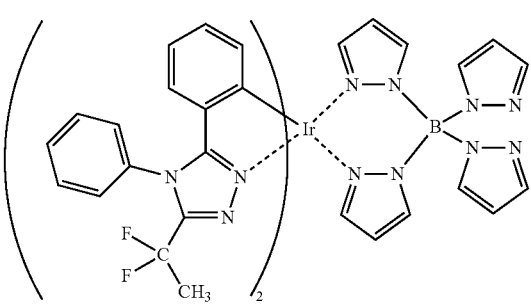
(114)
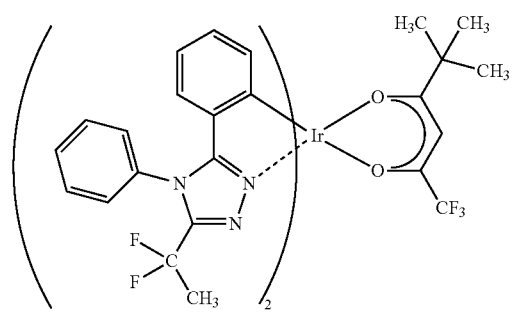
(115)
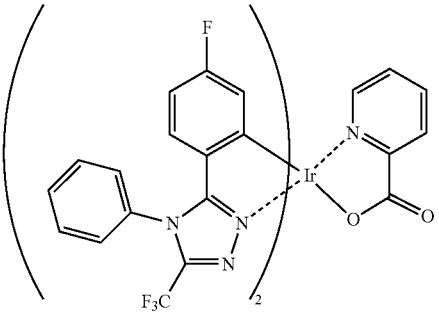
(116)
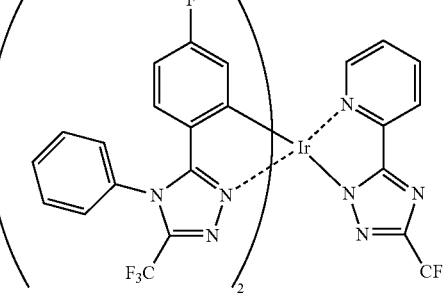
(117)
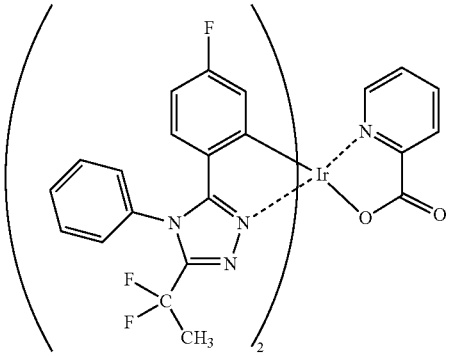
(118)
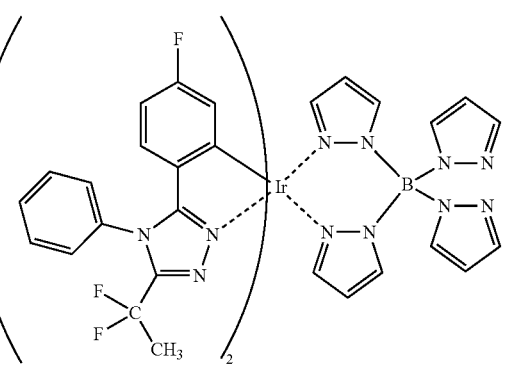
(119)

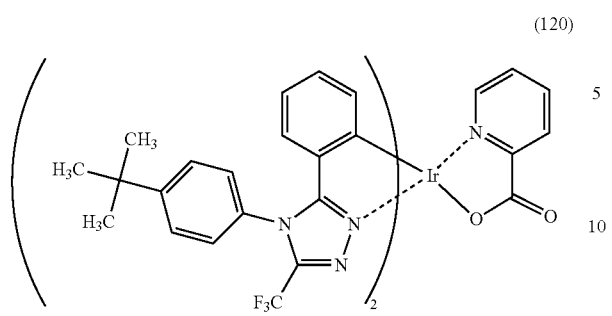
(120)
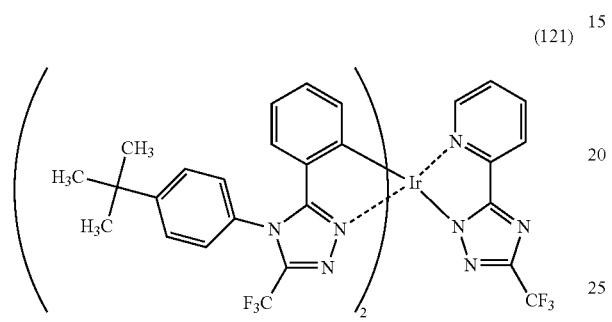
(121)
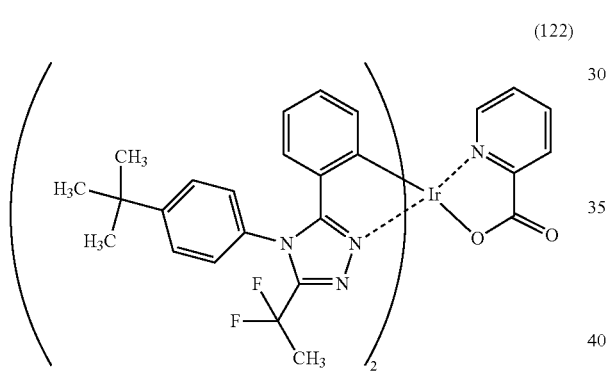
(122)
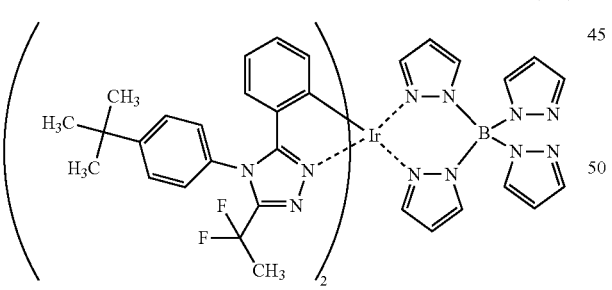
(123)
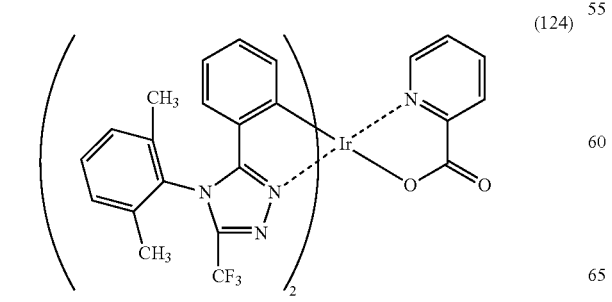
(124)
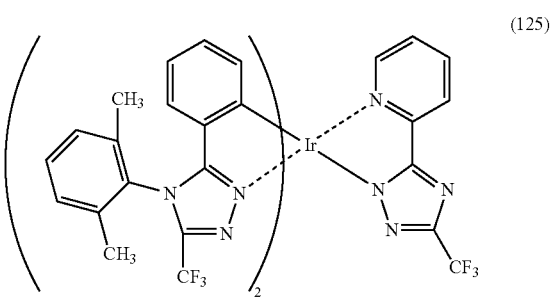
(125)
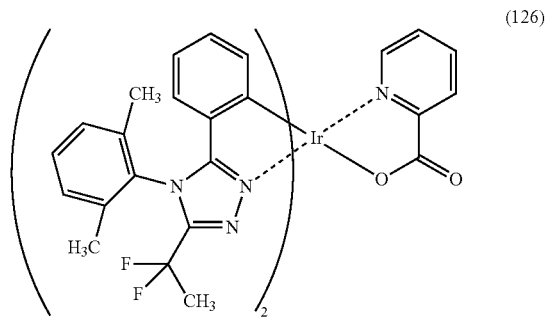
(126)
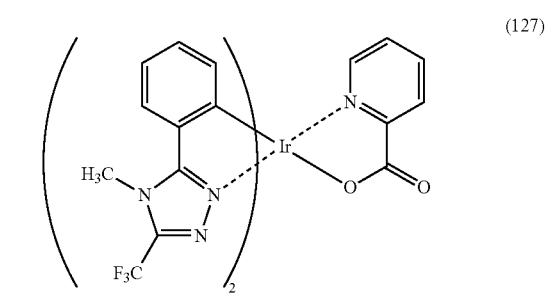
(127)
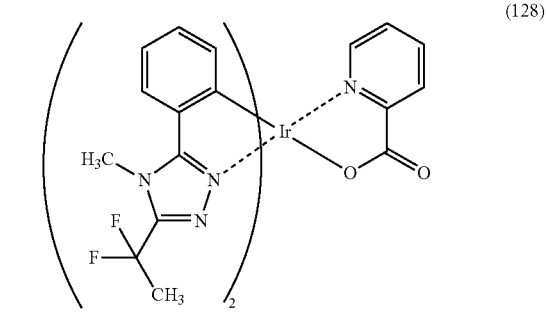
(128)
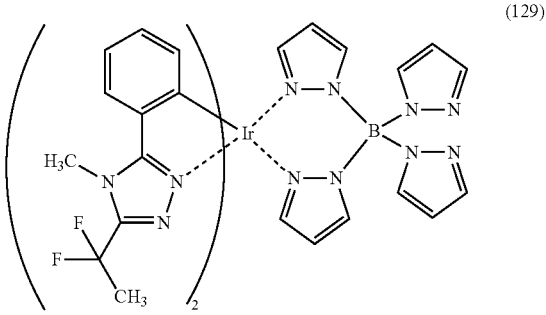
(129)

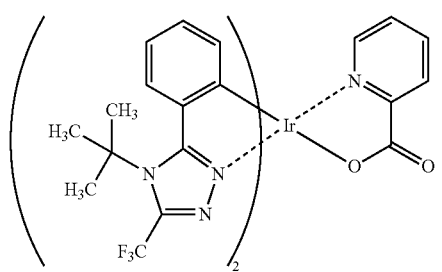
(130)
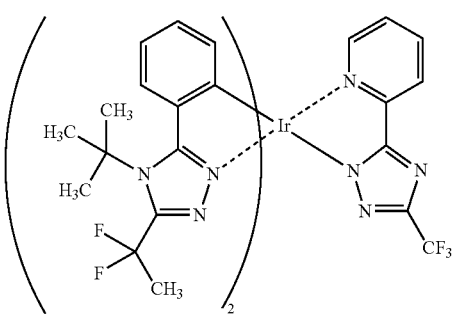
(131)
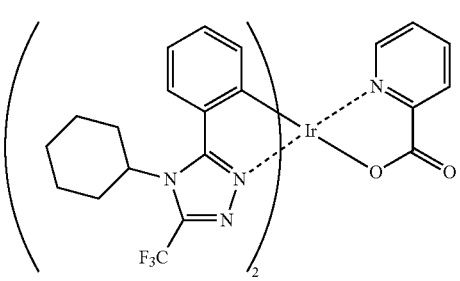
(132)
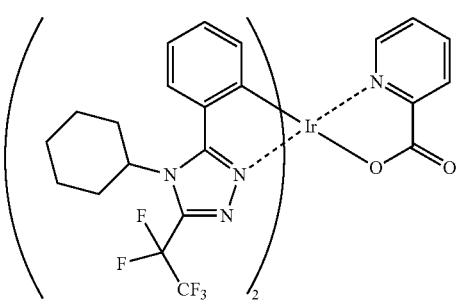
(133)
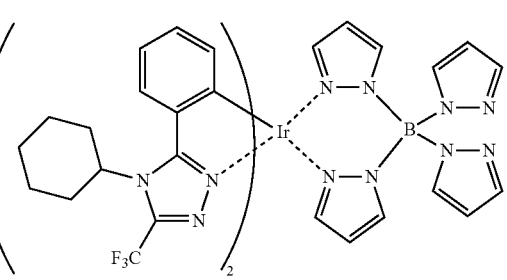
(134)
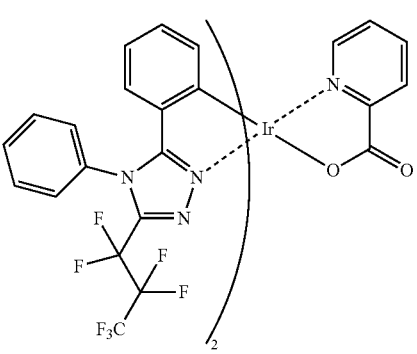
(135)
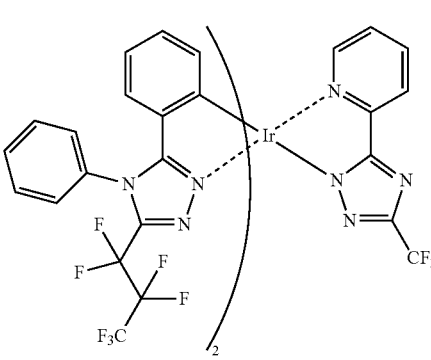
(136)
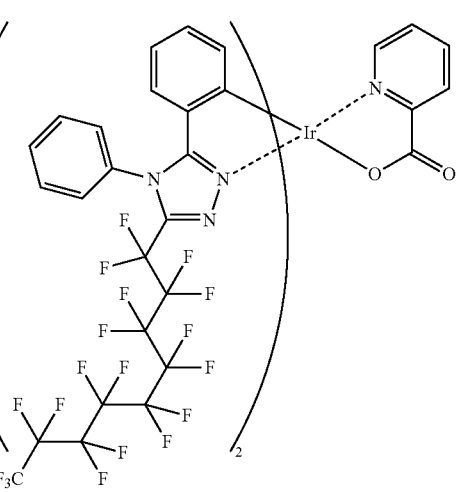
(137)

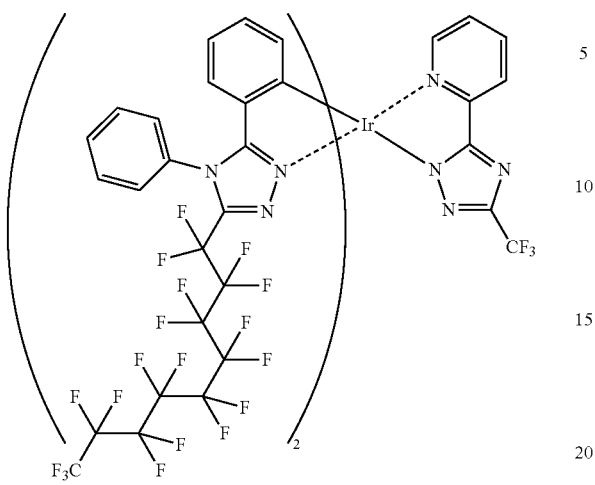
(138)
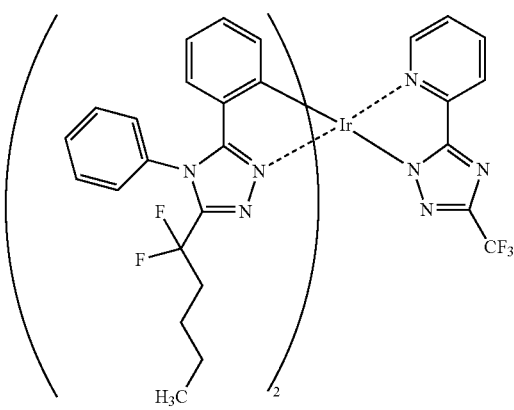
(142)
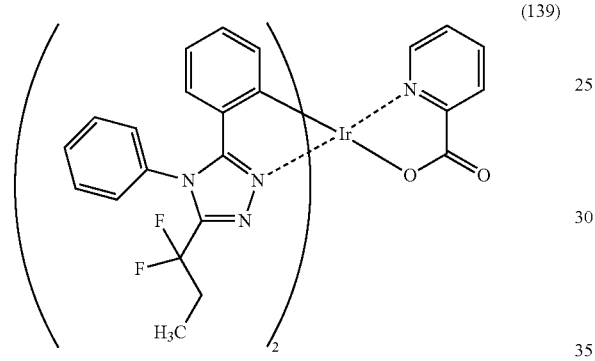
(139)
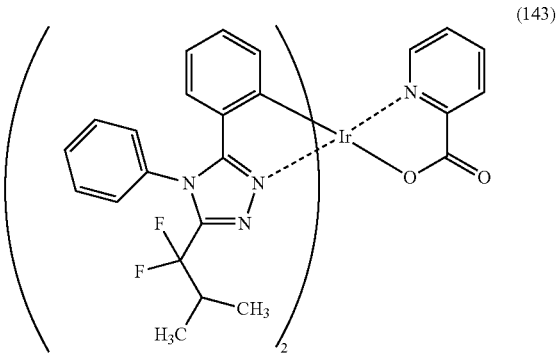
(143)
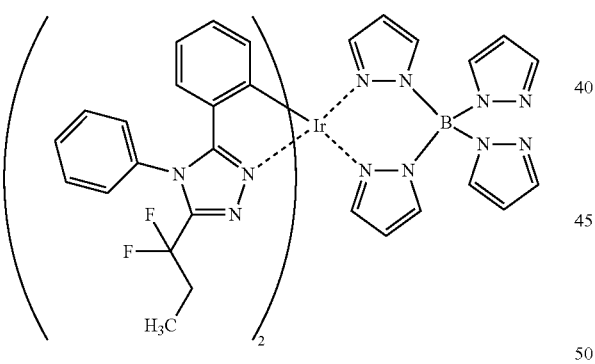
(140)
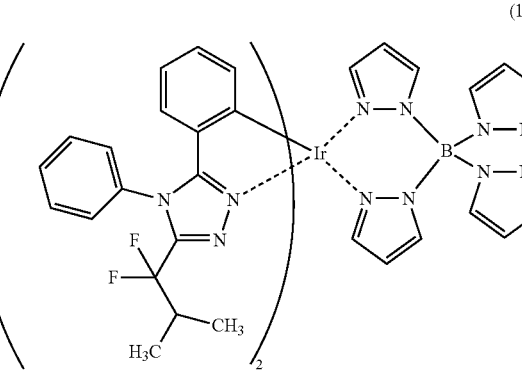
(144)
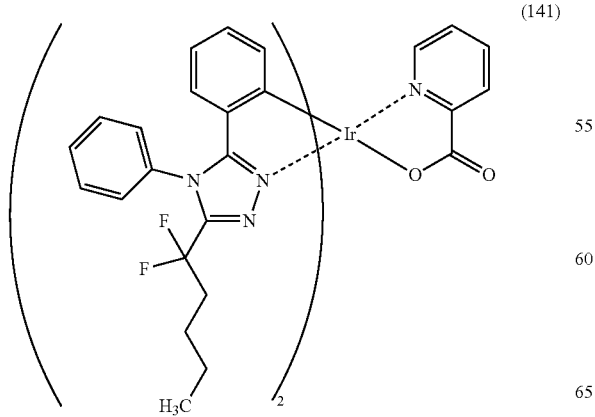
(141)
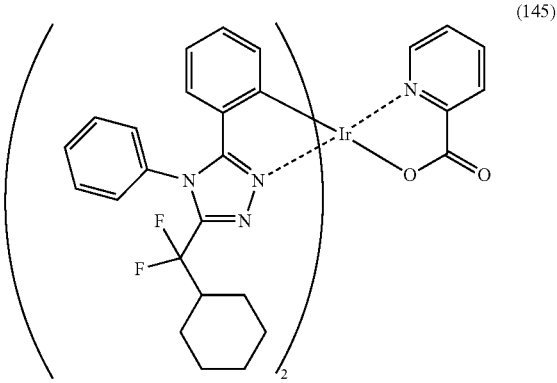
(145)

(146) 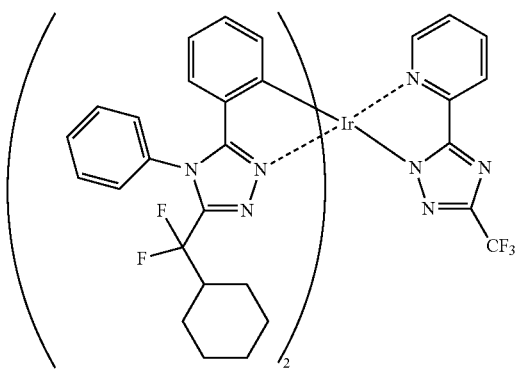
(147) 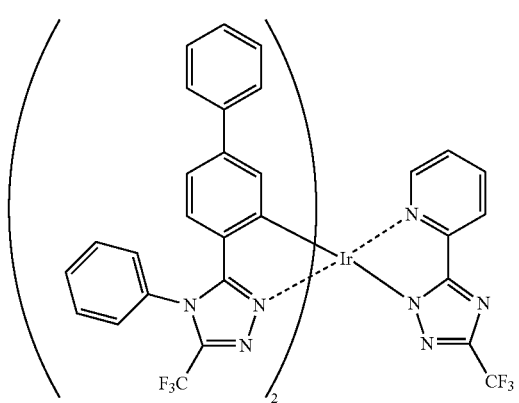
(148) 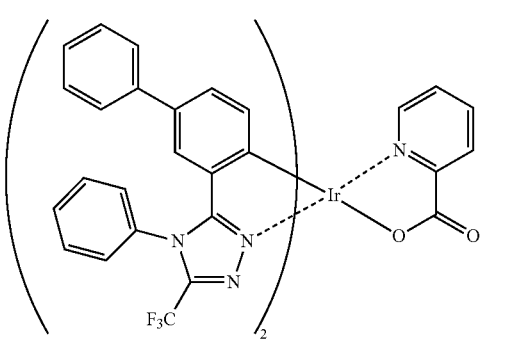
(149) 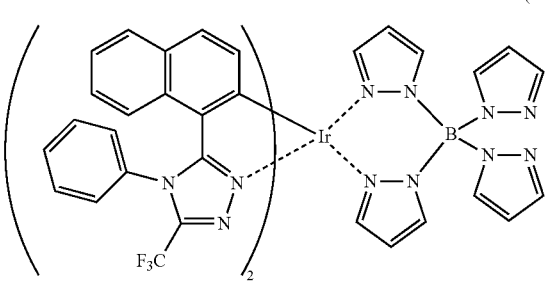
(150) 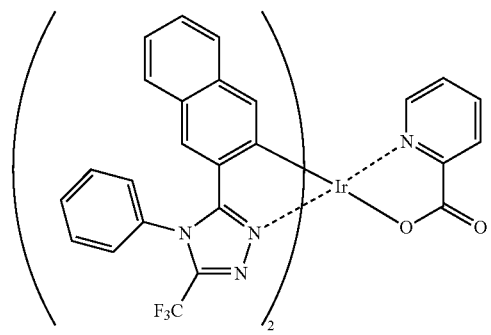
(151) 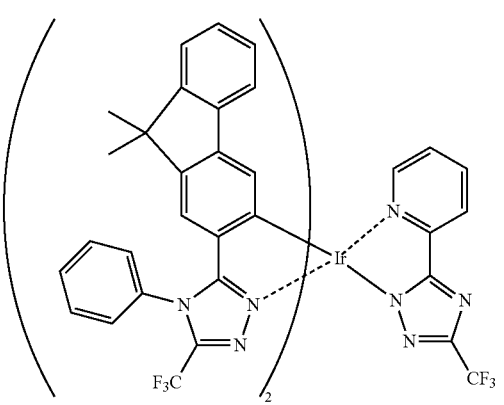
(152) 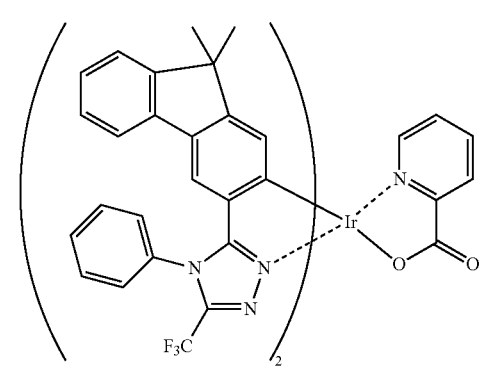
(153) 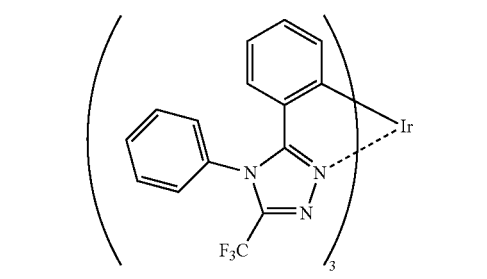

(154) 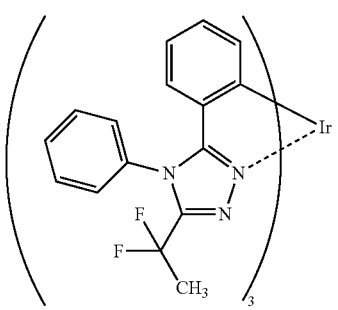
(155) 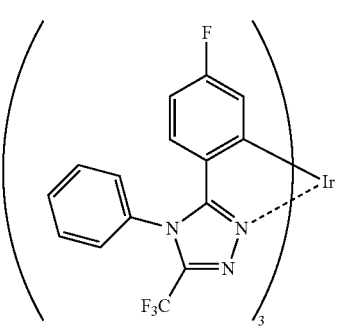
(156) 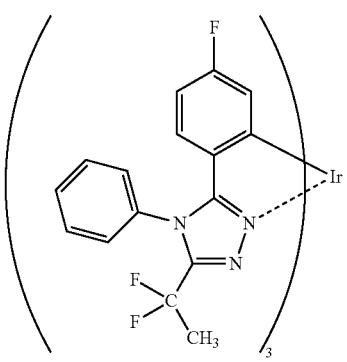
(157) 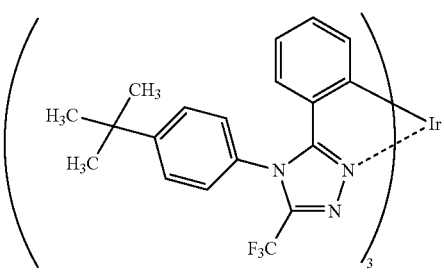
(158) 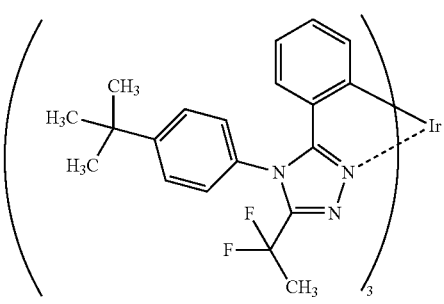
(159) 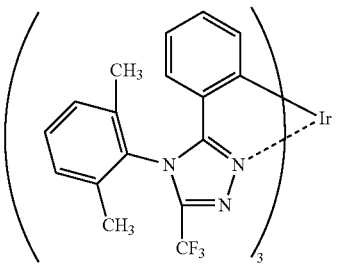
(160) 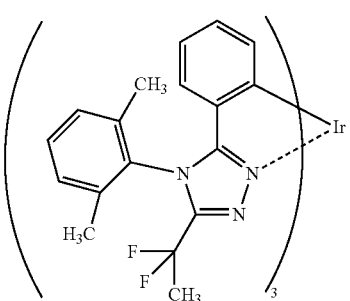
(161) 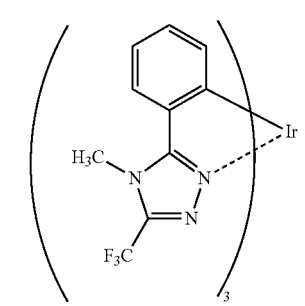
(162) 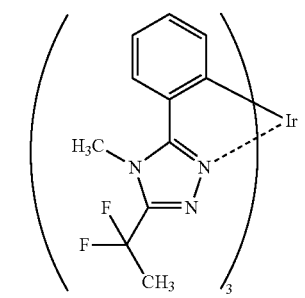
(163) 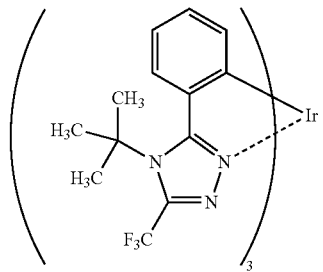

(164) 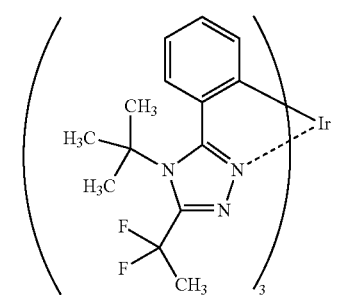
(165) 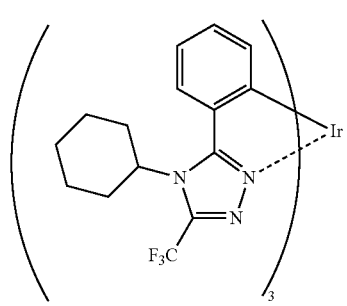
(166) 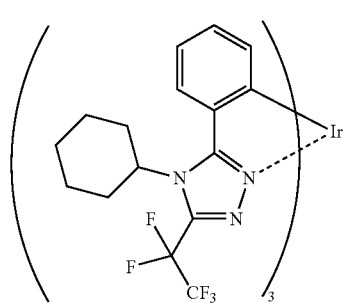
(167) 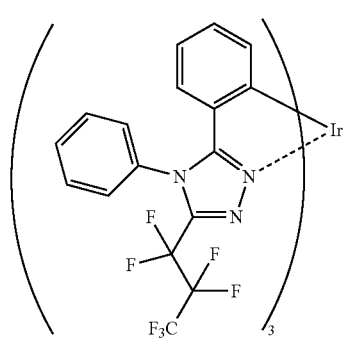
(168) 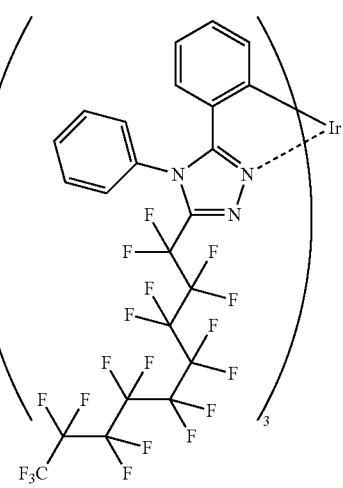
(169) 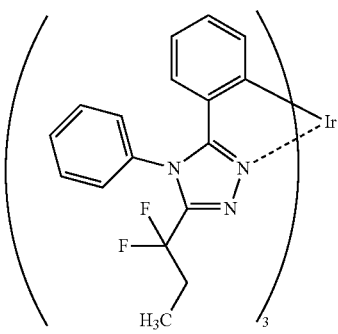
(170) 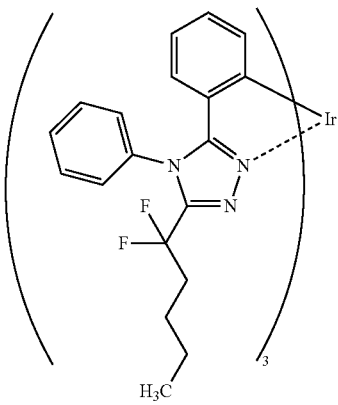
(171) 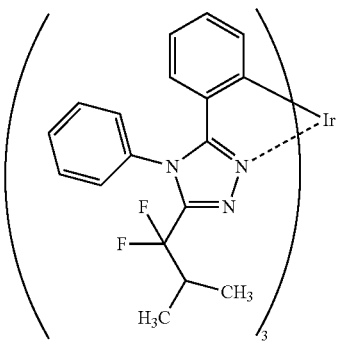

-continued (172) 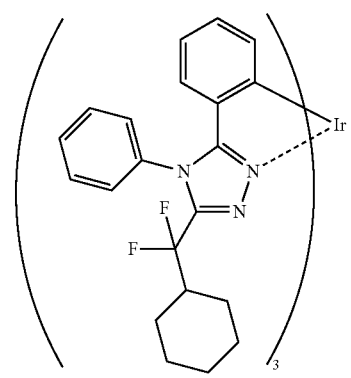

(173) 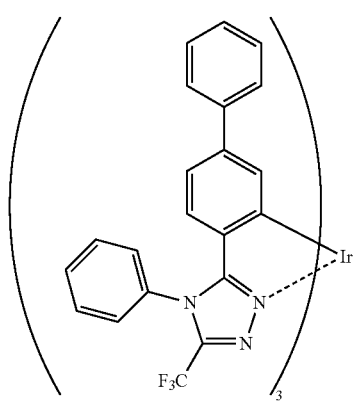

(174) 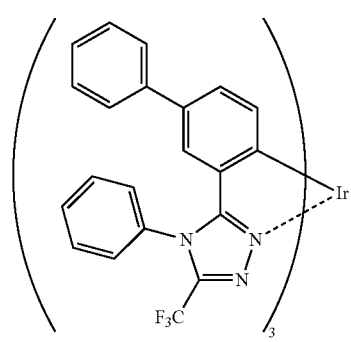

(175) 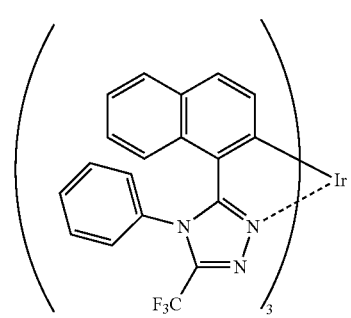

-continued (176) 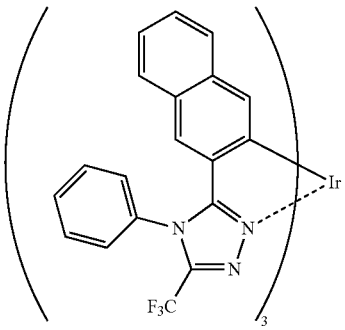

(177) 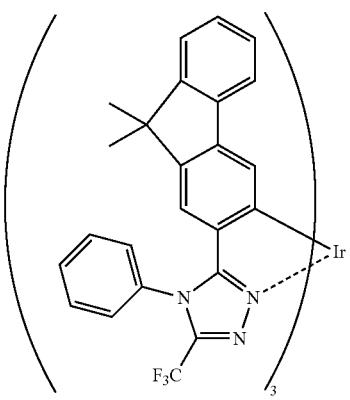

(178) 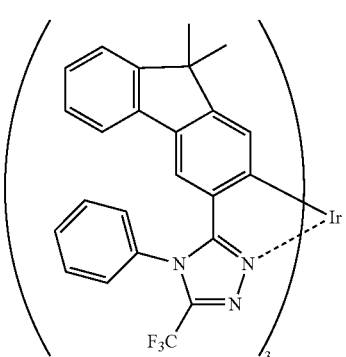

The above organometallic complexes each of which is one embodiment of the present invention are novel substances that can exhibit phosphorescence.

Next, an example of a synthesis method of an organometallic complex having the structure represented by General Formula (G1) is described.

Step 1: Synthesis Method of
3-Aryl-4H-1,2,4-Triazole Derivative

First, since a 3-aryl-4H-1,2,4-triazole derivative which is represented by General Formula (G0) below is a novel substance, an example of a synthesis method thereof is described. Note that in General Formula (G0), $R^1$ represents a haloalkyl group having 1 to 9 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an aryl group having 6 to 13 carbon atoms which may have a substituent.

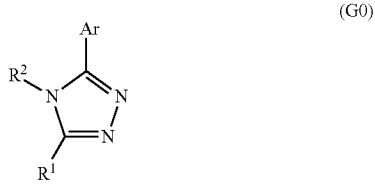

(G0)

Note that specific examples of $R^1$ include a fluoromethyl group, a trifluoromethyl group, a 1,1-difluoroethyl group, and a 1,1,2,2,3,3,3-heptafluoropropyl group, and a 1,1,2,2,3,3,4,4,5,5,6,6,7,7,8,8,9,9,9-nonadecafluorononyl group.

Specific examples of $R^2$ include a methyl group, an ethyl group, a propyl group, an isopropyl group, a butyl group, a sec-butyl group, an isobutyl group, a tert-butyl group, a hexyl group, a cyclopentyl group, a cyclohexyl group, a cycloheptyl group, a cyclooctyl group, a 1-methylcyclohexyl group, a 2,6-dimethylcyclohexyl group, a phenyl group, a biphenyl group, a phenyl group substituted by one or more methyl groups, a phenyl group substituted by one or more ethyl groups, a phenyl group substituted by one or more isopropyl groups, a phenyl group substituted by a tert-butyl group, a phenyl group substituted by a fluoro group, and a phenyl group substituted by a trifluoromethyl group.

Specific examples of Ar include a phenylene group, a phenylene group substituted by one or more alkyl groups, a phenylene group substituted by a cycloalkyl group, a phenylene group substituted by an alkoxy group, a phenylene group substituted by an aryloxy group, a phenylene group substituted by an alkylthio group, a phenylene group substituted by an arylthio group, a phenylene group substituted by a monoalkylamino group or a dialkylamino group, a phenylene group substituted by a monoarylamino group or a diarylamino group, a phenylene group substituted by an aryl group, a phenylene group substituted by one or more halogen groups, a phenylene group substituted by one or more haloalkyl groups, a biphenyl-diyl group, a naphthalene-diyl group, a fluorene-diyl group, a 9,9-dialkylfluorene-diyl group, and a 9,9-diarylfluorene-diyl group.

As shown in Scheme (a) below, by reacting a thioether compound containing Ar or an N-substituted thioamide compound containing Ar (A1) with a haloalkyl hydrazide compound (A2), the 3-aryl-4H-1,2,4-triazole derivative can be prepared. Note that in Scheme (a), $R^1$ represents a haloalkyl group having 1 to 9 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an aryl group having 6 to 13 carbon atoms which may have a substituent.

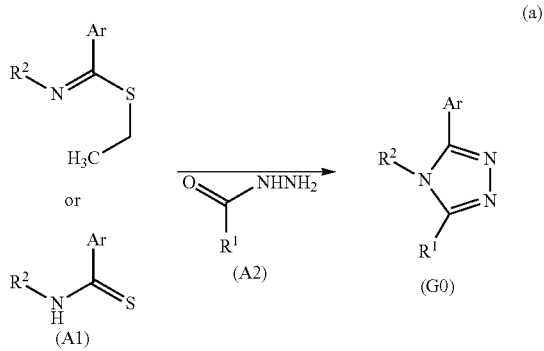

(a)

Note that the synthesis method of the 3-aryl-4H-1,2,4-triazole derivative is not limited to Scheme (a). For example, there is another example of a synthesis method in which a thioether compound containing $R^1$ and $R^2$ or an N-substituted thioamide compound containing $R^1$ and $R^2$ is reacted with an aryl hydrazide compound. As shown in Scheme (a') below, there is also a method in which a dihydrazide compound (A1') and a primary amine compound (A2') are reacted. Note that in Scheme (a'), $R^1$ represents a haloalkyl group having 1 to 9 carbon atoms which may have a substituent. In addition, $R^2$ represents any of an alkyl group having 1 to 6 carbon atoms, a cycloalkyl group having 5 to 8 carbon atoms which may have a substituent, and an aryl group having 6 to 12 carbon atoms which may have a substituent. Further, Ar represents an aryl group having 6 to 13 carbon atoms which may have a substituent.

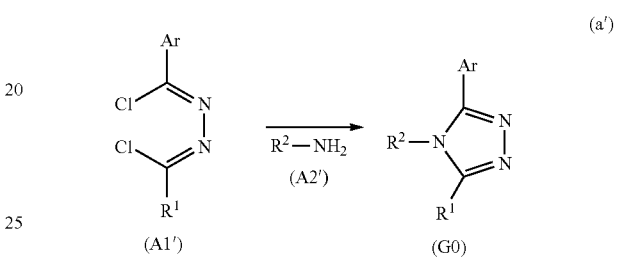

(a')

In the above manner, the 3-aryl-4H-1,2,4-triazole derivative can be synthesized by a simple synthetic scheme.

Step 2: Synthesis Method of Halogen-Bridged Binuclear Metal Complex

As shown in Synthesis Scheme (b) below, by mixing the 3-aryl-4H-1,2,4-triazole derivative, which can be prepared in Step 1, and a Group 9 or Group 10 metal compound (e.g., rhodium chloride hydrate, palladium chloride, iridium chloride hydrate, ammonium hexachloroiridate, potassium tetrachloroplatinate, or the like) containing a halogen, and then by heating the mixture in an inert gas atmosphere, a halogen-bridged binuclear metal complex (B) can be prepared. Note that this heating process may be performed after the 3-aryl-4H-1,2,4-triazole derivative, which can be prepared in Step 1, and a Group 9 or Group 10 metal compound containing a halogen are dissolved in an alcohol-based solvent (e.g., glycerol, ethylene glycol, 2-methoxyethanol, or 2-ethoxyethanol) alone or in a mixed solvent of water and one or more of the alcohol-based solvents. Although there is no particular limitation on a heating means, an oil bath, a sand bath, or an aluminum block bath may be used as a heating means. Alternatively, microwaves can be used as a heating means. Note that in Scheme (b), M represents a Group 9 element or a Group 10 element. When M is a Group 9 element, n is 3, and when M is a Group 10 element, n is 2. Further, X represents a halogen.

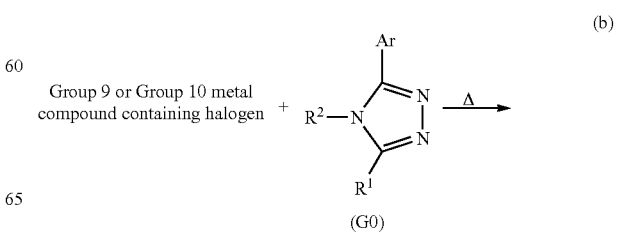

(b)

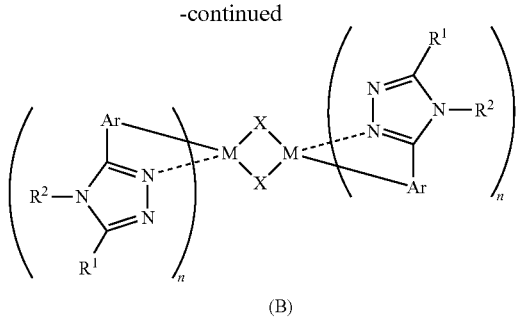

(B)

Step 3: Synthesis Method of Ortho-Metalated Complex Having 3-Aryl-4H-1,2,4-Triazole Derivative as Ligand As shown in Synthesis Scheme (c) below, by mixing the halogen-bridged binuclear metal complex, which can be prepared in Step 2, and HL (H represents hydrogen), which is a source material of a monoanionic bidentate ligand L, and then by heating the mixture in an inert gas atmosphere, a proton of HL is eliminated to be coordinated to the central metal M, so that an organometallic complex represented by General Formula (G2) can be prepared. Although there is no particular limitation on a heating means, an oil bath, a sand bath, or an aluminum block bath may be used as a heating means. Alternatively, microwaves can be used as a heating means.

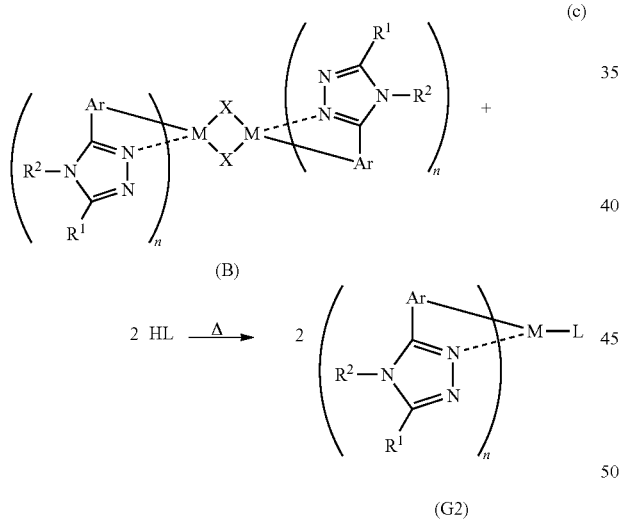

In the present invention, as described above, a haloalkyl group having 1 to 9 carbon atoms which may have a substituent in $R^1$ is used so that an ortho-metalated complex having a 3-aryl-4H-1,2,4-triazole derivative as a ligand can be prepared. Therefore, as compared to the case where an alkyl group is used in $R^1$, decomposition of the halogen-bridged binuclear metal complex synthesized in Synthesis Scheme (b) is suppressed during reaction represented by Synthesis Scheme (c), and a high yield can be obtained. In addition, by using a haloalkyl group having 1 to 9 carbon atoms which may have a substituent in $R^1$, as compared to the case where an alkyl group is used, an organometallic complex having a peak of emission in a short wavelength side can be prepared. Thus, the use of a haloalkyl group having 1 to 9 carbon atoms which may have a substituent in $R^1$ is advantageous in preparing a material that exhibits phosphorescence having a wavelength band of blue.

Note that examples of a monoanionic bidentate ligand include a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen; specifically, ligands represented by Structural Formulas (L1) to (L6) below can be given.

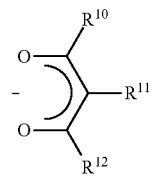

(L1)

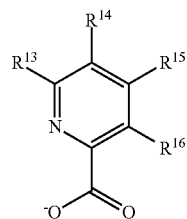

(L2)

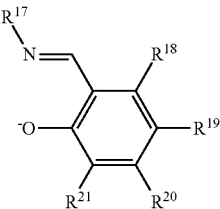

(L3)

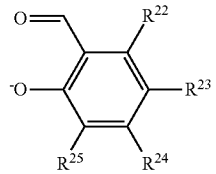

(L4)

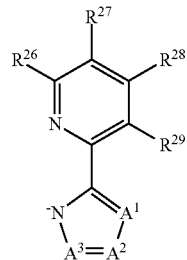

(L5)

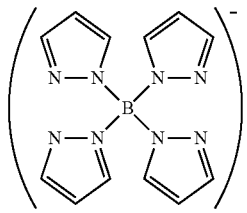

(L6)

A heteroleptic organometallic complex can be prepared in Synthesis Schemes (b) and (c); however, a homoleptic organometallic complex can be prepared in Synthesis Scheme (b') below.

Step 2': Synthesis Method of Ortho-Metalated Complex Having 3-Aryl-4H-1,2,4-Triazole Derivative as Ligand As shown in Synthetic Scheme (b') below, by mixing the 3-aryl-4H-1,2,4-triazole derivative, which can be prepared in Step 1, and a Group 9 or Group 10 metal compound (e.g., rhodium chloride hydrate, palladium chloride, iridium chloride hydrate, ammonium hexachloroiridate, or potassium tetrachloroplatinate) containing a halogen or a Group 9 or Group 10 organometallic complex compound (e.g., an acetylacetonate complex or a diethylsulfide complex), and then by heating the mixture, an organometallic complex having a structure represented by General Formula (G2') can be prepared. This heating process can be performed after the 3-aryl-4H-1,2,4-triazole derivative, which can be prepared in Step 1, and a Group 9 or Group 10 metal compound containing a halogen or a Group 9 or Group 10 organometallic complex compound are dissolved in an alcohol-based solvent (e.g., glycerol, ethylene glycol, 2-metoxyethanol, or 2-ethoxyethanol). Note that in Synthetic Scheme (b'), M represents a Group 9 element or a Group 10 element. When M is a Group 9 element, n is 3, and when M is a Group 10 element, n is 2.

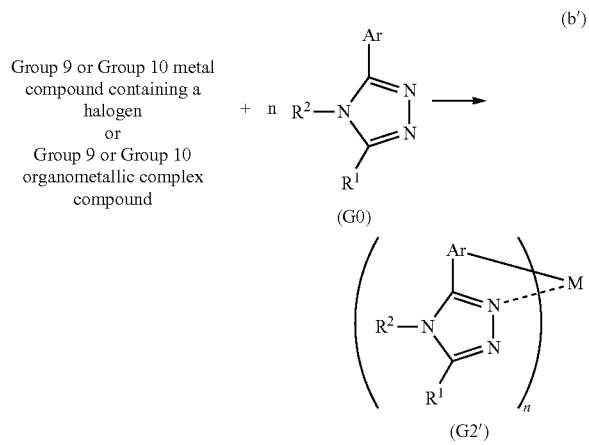

Since various kinds of the above compounds (A1), (A2), (A1'), and (A2') are commercially available or can be synthesized, many kinds of 3-aryl-4H-1,2,4-triazole derivatives represented by General Formula (G0) can be synthesized. Accordingly, an organometallic complex which is one embodiment of the present invention has a feature of wide variations of a ligand. By using such an organometallic complex having wide variations of a ligand in manufacture of a light-emitting element, fine adjustment of element characteristics required for the light-emitting element can be performed easily.

Embodiment 2

One embodiment of a light-emitting element using the organometallic complex described in Embodiment 1 is described with reference to FIG. 1A.

The light-emitting element includes a pair of electrodes (a first electrode 102 and a second electrode 104) and an EL layer 103 interposed between the pair of electrodes. The light-emitting element described in this embodiment is provided over a substrate 101.

The substrate 101 is used as a support of the light-emitting element. As the substrate 101, a glass substrate, a plastic substrate, or the like can be used. As the substrate 101, a substrate having flexibility (a flexible substrate) or a substrate having a curved surface can also be used. A substrate other than the above substrates can also be used as the substrate 101 as long as it functions as a support of the light-emitting element.

One of the first electrode 102 and the second electrode 104 serves as an anode and the other serves as a cathode. In this embodiment, the first electrode 102 is used as the anode and the second electrode 104 is used as the cathode; however, the present invention is not limited to this structure.

It is preferable to use a metal, an alloy, or a conductive compound, a mixture thereof, or the like having a high work function (specifically, more than or equal to 4.0 eV) as a material for the anode. Specifically, indium oxide-tin oxide (ITO: indium tin oxide), indium oxide-tin oxide containing silicon or silicon oxide, indium oxide-zinc oxide (IZO: indium zinc oxide), indium oxide containing tungsten oxide and zinc oxide (IWZO), and the like can be given. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), or the like can be given.

It is preferable to use a metal, an alloy, or a conductive compound, a mixture thereof, or the like having a low work function (specifically, less than or equal to 3.8 eV) as a material for the cathode. Specifically, an element belonging to Group 1 or Group 2 of the periodic table, that is, an alkali metal such as lithium (Li) and cesium (Cs), and an alkaline earth metal such as magnesium (Mg), calcium (Ca), and strontium (Sr) can be given. An alloy containing an alkali metal or an alkaline earth metal (e.g., MgAg or AlLi) can also be used. Moreover, a rare earth metal such as europium (Eu) or ytterbium (Yb), or an alloy containing a rare earth metal can also be used. In the case where an electron-injection layer in contact with the second electrode 104 is provided as part of the EL layer 103, the second electrode 104 can be formed using a variety of conductive materials such as Al, Ag, or ITO, regardless of their work functions. Film formation using such a conductive material can be performed by a sputtering method, an inkjet method, a spin coating method, or the like.

Although the EL layer 103 can be formed to have a single-layer structure, it is normally formed to have a stacked-layer structure. There is no particular limitation on the stacked-layer structure of the EL layer 103. It is possible to combine, as appropriate, a layer containing a substance having a high electron-transport property (an electron-transport layer) or a layer containing a substance having a high hole-transport property (a hole-transport layer), a layer containing a substance having a high electron-injection property (an electron-injection layer), a layer containing a substance having a high hole-injection property (a hole-injection layer), a layer containing a bipolar substance (a substance having high electron- and hole-transport properties), a layer containing a light-emitting substance (a light-emitting layer), and the like. For example, the EL layer 103 can be formed in an appropriate combination of a hole-injection layer, a hole-transport layer, a light-emitting layer, an electron-transport layer, an electron-injection layer, and the like. FIG. 1A illustrates as the EL layer 103 formed over the first electrode 102, a structure in which a hole-injection layer 111, a hole-transport layer 112, a light-emitting layer 113, and an electron-transport layer 114 are sequentially stacked.

In a light-emitting element, when current flows owing to a potential difference generated between the first electrode 102 and the second electrode 104, holes and electrons are recombined in the light-emitting layer 113 containing a substance having a high light-emitting property, and light is emitted. That is, a light-emitting region is formed in the light-emitting layer 113.

The emitted light is extracted out through one or both of the first electrode 102 and the second electrode 104. Therefore, one or both of the first electrode 102 and the second electrode 104 are light-transmitting electrodes. When only the first electrode 102 is an electrode having a light-transmitting property, emitted light is extracted from the substrate side through the first electrode 102. Meanwhile, when only the second electrode 104 has a light-transmitting property, emitted light is extracted from the side opposite to the substrate side through the second electrode 104. In the case where each of the first electrode 102 and the second electrode 104 has a light-transmitting property, emitted light is extracted from both of the substrate side and the side opposite to the substrate side through the first electrode 102 and the second electrode 104.

An organometallic complex including the structure represented by General Formula (G1) which is one embodiment of the present invention can be used for the light-emitting layer 113, for example. In this case, the light-emitting layer 113 may be formed with a thin film containing the organometallic complex including the structure represented by General Formula (G1), or may be formed with a thin film in which a host material is doped with the organometallic complex including the structure represented by General Formula (G1).

In order to suppress energy transfer from an exciton which is generated in the light-emitting layer 113, the hole-transport layer 112 or the electron-transport layer 114 which is in contact with the light-emitting layer 113, particularly a carrier-(electron- or hole-) transport layer in contact with a side closer to a light-emitting region in the light-emitting layer 113, is preferably formed using a substance having an energy gap larger than an energy gap of a light-emitting substance contained in the light-emitting layer or an energy gap of an emission center substance contained in the light-emitting layer.

The hole-injection layer 111 contains a substance having a high hole-injection property, and has a function of helping injection of holes from the first electrode 102 to the hole-transport layer 112. By providing the hole-injection layer 111, a difference between ionization potentials of the first electrode 102 and the hole-transport layer 112 is relieved, so that holes are easily injected. The hole-injection layer 111 is preferably formed using a substance having a smaller ionization potential than a substance contained in the hole-transport layer 112 and having a larger ionization potential than a substance contained in the first electrode 102, or a substance in which an energy band is bent when the substance is provided as a thin film with a thickness of 1 to 2 nm between the hole-transport layer 112 and the first electrode 102. That is, a material for the hole-injection layer 111 is preferably selected so that the ionization potential of the hole-injection layer 111 is relatively smaller than that of the hole-transport layer 112. Specific examples of substances having a high hole-injection property include phthalocyanine (abbreviation: $H_2Pc$), a phthalocyanine-based compound such as copper phthalocyanine (abbreviation: CuPc), a high molecular compound such as poly(ethylenedioxythiophene)/poly(styrenesulfonate) aqueous solution (PEDOT/PSS), and the like.

The hole-transport layer 112 contains a substance with a high hole-transport property. Note that a substance having a high hole-transport property is a substance where hole mobility is higher than electron mobility and the ratio value of hole mobility to electron mobility (=hole mobility/electron mobility) is preferably more than 100. A substance having a hole mobility of more than or equal to $1 \times 10^{-6}$ cm$^2$/Vs is preferably used as a substance having a high hole-transport property. Specific examples of substances having a high hole-transport property include 4,4'-bis[N-(1-naphthyl)-N-phenylamino]biphenyl (abbreviation: NPB), 4,4'-bis[N-(3-methylphenyl)-N-phenylamino]biphenyl (abbreviation: TPD), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), N,N'-bis[4-[bis(3-methylphenyl)amino]phenyl]-N,N'-diphenyl-[1,1'-biphenyl]-4,4'-diamine (abbreviation: DNTPD), 1,3,5-tris[N,N-di(m-tolyl)amino]benzene (abbreviation: m-MTDAB), 4,4',4"-tris(N-carbazolyl)triphenylamine (abbreviation: TCTA), phthalocyanine (abbreviation: $H_2Pc$), copper phthalocyanine (abbreviation: CuPc), vanadyl phthalocyanine (abbreviation: VOPc), and the like can be given. Note that the hole-transport layer 112 may have a single-layer structure or a stacked-layer structure.

The electron-transport layer 114 contains a substance with a high electron-transport property. Note that a substance having a high electron-transport property is a substance where electron mobility is higher than hole mobility and the ratio value of electron mobility to hole mobility (=electron mobility/hole mobility) is preferably more than 100. A substance having an electron mobility of more than or equal to $1 \times 10^{-6}$ cm$^2$/Vs is preferably used as a substance having a high electron-transport property. Specific examples of substances having a high electron-transport property include a metal complex having a quinoline skeleton, a metal complex having a benzoquinoline skeleton, a metal complex having an oxazole-based ligand, and a metal complex having a thiazole-based ligand. Specific examples of metal complexes having a quinoline skeleton include tris(8-quinolinolato)aluminum (abbreviation: Alq), tris(4-methyl-8-quinolinolato)aluminum (abbreviation: Almq$_3$), and bis(2-methyl-8-quinolinolato)(4-phenylphenolato)aluminum (abbreviation: BAlq). A specific example of a metal complex having a benzoquinoline skeleton is bis(10-hydroxybenzo[h]quinolinato)beryllium (abbreviation: BeBq$_2$). A specific example of a metal complex having an oxazole-based ligand is bis[2-(2-hydroxyphenyl)benzoxazolato]zinc (abbreviation: Zn(BOX)$_2$). A specific example of a metal complex having a thiazole-based ligand is bis[2-(2-hydroxyphenyl)benzothiazolato]zinc (abbreviation: Zn(BTZ)$_2$). Instead of the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ01), bathophenanthroline (abbreviation: BPhen), bathocuproine (abbreviation: BCP), or the like can be used. The substances specifically listed above are mainly substances having an electron mobility of more than or equal to $1 \times 10^{-6}$ cm$^2$/Vs. Note that any substance other than the above substances may be used for the electron-transport layer 114 as long as the electron-transport property is higher than the hole-transport property. Further, the electron-transport layer 114 may have a single-layer structure or a stacked-layer structure.

Further, a layer for controlling transport of electron carriers may be provided between the light-emitting layer 113 and the electron-transport layer 114. Note that the layer for controlling transport of electron carriers is a layer obtained by adding a small amount of substance having a high electron-trapping property to the above material having a high electron-transport property. By providing the layer for controlling transport of electron carriers, it is possible to suppress transfer of electron carriers, and to adjust carrier balance. Such a structure is very effective in suppressing a problem (such as shortening of the element lifetime) caused when electrons pass through the light-emitting layer.

In addition, an electron-injection layer may be provided between the electron-transport layer 114 and the second electrode 104, in contact with the second electrode 104. As the electron-injection layer, a layer which contains a substance having an electron-transport property and an alkali metal, an alkaline earth metal, or a compound thereof such as lithium fluoride (LiF), cesium fluoride (CsF), or calcium fluoride ($CaF_2$) may be used. Specifically, a layer containing Alq and magnesium (Mg) can be used. By providing the electron-injection layer, electrons can be injected efficiently from the second electrode 104.

Various methods can be used for forming the EL layer 103, regardless of a dry method or a wet method. For example, a vacuum evaporation method, an inkjet method, a spin-coating method, or the like can be used. When the EL layer 103 has a stacked-layer structure, deposition methods of the layers may be different or the same.

The first electrode 102 and the second electrode 104 may be formed by a wet method using a sol-gel method, or a wet method using a paste of a metal material. Further, the electrodes may be formed by a dry method such as sputtering or vacuum evaporation.

Embodiment 3

In this embodiment, an embodiment of a light-emitting element in which a plurality of light-emitting units are stacked (hereinafter this light-emitting element is referred to as a "tandem light-emitting element") is described with reference to FIG. 1B. The tandem light-emitting element is a light-emitting element having a plurality of light-emitting units between a first electrode and a second electrode. The light-emitting units can be similar to the EL layer 103 described in Embodiment 2. That is, the light-emitting element described in Embodiment 2 has a single light-emitting unit, and the light-emitting element described in this embodiment has a plurality of light-emitting units.

Figure 1B:
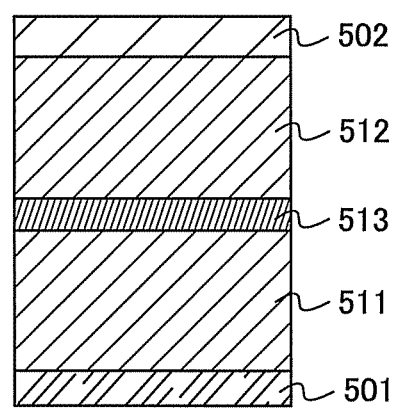

In FIG. 1B, a first light-emitting unit 511 and a second light-emitting unit 512 are stacked between a first electrode 501 and a second electrode 502. Electrodes similar to those described in Embodiment 2 can be used as the first electrode 501 and the second electrode 502. Alternatively, the structures of the first light-emitting unit 511 and the second light-emitting unit 512 may be the same or different from each other, and each of the structures can be similar to the structure described in Embodiment 2.

A charge-generating layer 513 is provided between the first light-emitting unit 511 and the second light-emitting unit 512. The charge-generating layer 513 contains a composite material of an organic compound and a metal oxide and has a function of injecting electrons to one side of the light-emitting unit, and holes to the other side of the light-emitting unit, when voltage is applied between the first electrode 501 and the second electrode 502. The composite material of the organic compound and the metal oxide can achieve low-voltage driving and low-current driving because the carrier-injection property and carrier-transport property are superior.

It is preferable to use an organic compound which has a hole-transport property and has a hole mobility of more than or equal to $1\times10^{-6}$ $cm^2/Vs$ as the organic compound. Specific examples of the organic compound include an aromatic amine compound, a carbazole compound, aromatic hydrocarbon, and a high molecular compound (an oligomer, a dendrimer, a polymer, or the like). It is possible to use oxide of a metal belonging to Group 4 to Group 8 in the periodic table as the metal oxide; specifically, it is preferable to use any of vanadium oxide, niobium oxide, tantalum oxide, chromium oxide, molybdenum oxide, tungsten oxide, manganese oxide, and rhenium oxide. Such metal oxides are preferable since they have high electron-accepting properties. In particular, molybdenum oxide is especially preferable because it is stable in the air, its hygroscopicity is low, and it can be easily handled.

The charge-generating layer 513 may have a single-layer structure or a stacked-layer structure. For example, it is possible to have a stacked-layer structure of a layer containing a composite material of an organic compound and a metal oxide, and a layer containing one compound selected from electron-donating substances and a compound having a high electron-transport property; or a stacked-layer structure of a layer containing a composite material of an organic compound and a metal oxide, and a transparent conductive film.

In this embodiment, the light-emitting element having two light-emitting units is described; however, the present invention is not limited to this structure. That is, a tandem light-emitting element may have three or more light-emitting units. Note that the light-emitting elements having three or more light-emitting units include a charge-generating layer between the light-emitting units. For example, it is possible to form a light-emitting element having a first unit formed using an organometallic complex which is one embodiment of the present invention, and a second unit formed using a light-emitting material which emits light with a longer wavelength than the organometallic complex (e.g., red light). In addition, it is also possible to form a light-emitting element having a first unit formed using an organometallic complex which is one embodiment of the present invention, a second unit formed using a first light-emitting material which emits light with a longer wavelength than the organometallic complex (e.g., red light), and a third unit formed using a second light-emitting material which emits light with a longer wavelength than the organometallic complex and a shorter wavelength than the first light-emitting material (e.g., green light). By using these light-emitting elements, a white light-emitting device can be realized. In particular, an emission spectrum of the organometallic complex which is one embodiment of the present invention has a broad peak. Thus, by using the organometallic complex which is one embodiment of the present invention in at least one light-emitting unit in a tandem light-emitting element, a light-emitting device with excellent white reproducibility (color rendering properties) can be easily provided.

By arranging a plurality of light-emitting units that are partitioned by a charge-generating layer between a pair of electrodes, the tandem light-emitting element of this embodiment can be an element having a long lifetime in a high luminance region while keeping a current density low.

Embodiment 4

In this embodiment, a passive-matrix light-emitting device and an active-matrix light-emitting device are described which are examples of a light-emitting device manufactured with the use of the light-emitting element described in the above embodiments.

FIGS. 2A to 2D and FIG. 3 illustrate an example of the passive-matrix light-emitting device.

A passive-matrix (also called simple-matrix) light-emitting device has a structure in which anodes arranged in stripes (in stripe form) are provided to be perpendicular to cathodes arranged in stripes. A light-emitting layer is interposed at each intersection. Therefore, a pixel at an intersection of an anode selected (to which voltage is applied) and a cathode selected emits light.

Figure 2A:
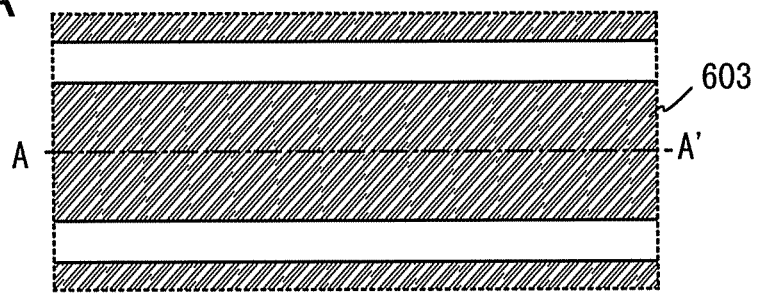
FIGS. 2A to 2D illustrate an example of a light-emitting device according to one embodiment of the present invention.
Figure 2B:
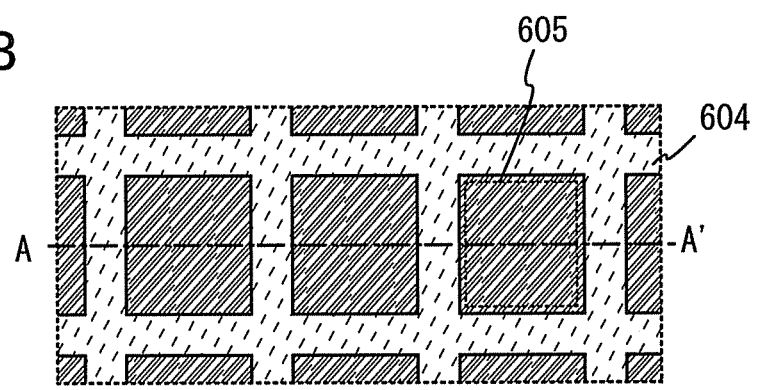
Figure 2C:
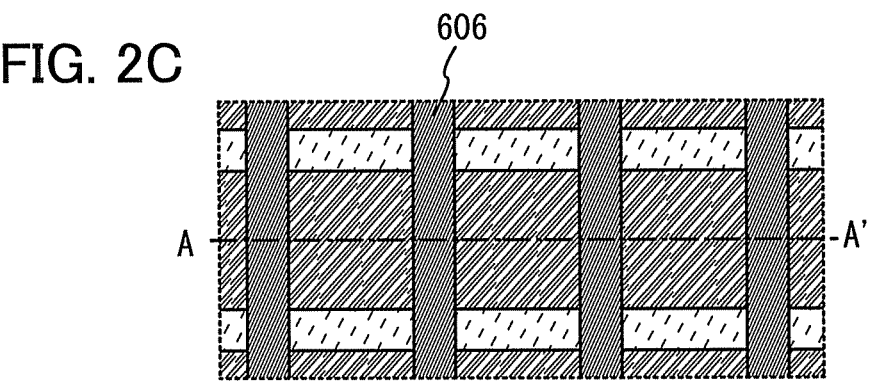
Figure 2D:
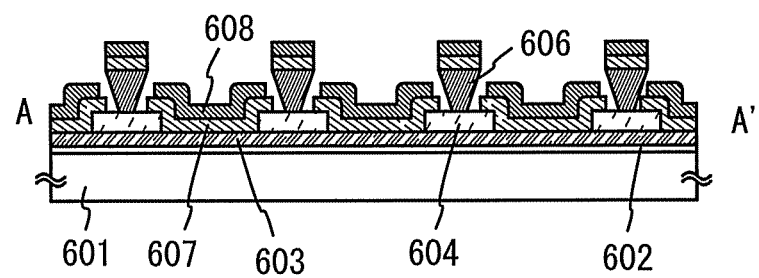

FIGS. 2A to 2C are top views of a pixel portion before sealing. FIG. 2D is a cross-sectional view taken along chain line A-A' in FIGS. 2A to 2C.

Over a substrate 601, an insulating layer 602 is formed as a base insulating layer. Note that the insulating layer 602 may be omitted when unnecessary. Over the insulating layer 602, a plurality of first electrodes 603 are arranged in stripes at regular intervals (see FIG. 2A). Note that each of the first electrodes 603 in this embodiment corresponds to the first electrode 102 in Embodiment 2.

In addition, a partition 604 having openings 605 corresponding to pixels is provided over the first electrodes 603. The partition 604 is formed using an insulating material. For example, a photosensitive or non-photosensitive organic material such as polyimide, acrylic, polyamide, polyimide amide, a resist, or benzocyclobutene, or an SOG film such as an $SiO_x$ film that contains an alkyl group can be used as the insulating material. Note that the openings 605 corresponding to pixels serve as light-emitting regions (see FIG. 2B).

Over the partition 604 having openings, a plurality of partitions 606 are provided to intersect with the first electrodes 603 (see FIG. 2C). The plurality of partitions 606 are formed in parallel to each other, and are inversely tapered.

Over each of the first electrodes 603 and the partition 604, an EL layer 607 and a second electrode 608 are sequentially stacked (see FIG. 2D). Note that the EL layer 607 in this embodiment corresponds to the EL layer 103 in Embodiment 2, and the second electrode 608 in this embodiment corresponds to the second electrode 104 in Embodiment 2. The total thickness of the partition 604 and the partition 606 is larger than the total thickness of the EL layer 607 and the second electrode 608; therefore, the EL layer 607 and the second electrode 608 are divided into regions as illustrated in FIG. 2D. Note that the regions are electrically isolated from one another.

The second electrodes 608 are formed in stripes and extend in the direction in which they intersect with the first electrodes 603. Note that a part of the EL layers 607 and a part of conductive layers forming the second electrodes 608 are formed over the inversely tapered partition walls 606; however, they are separated from the EL layers 607 and the second electrodes 608.

In addition, a sealing member such as a sealing can or a glass substrate may be attached to the substrate 601 with adhesive such as a sealant so that the light-emitting element can be placed in a sealed space, as needed. Thus, deterioration of the light-emitting element can be prevented. Note that the sealed space may be filled with filler or a dry inert gas. Further, a desiccant or the like is preferably put between the substrate and the sealing material to prevent deterioration of the light-emitting element due to moisture or the like. The desiccant removes a minute amount of moisture, thereby achieving sufficient desiccation. As the desiccant, oxide of an alkaline earth metal such as calcium oxide or barium oxide, zeolite, or silicagel can be used. Oxide of an alkaline earth metal absorbs moisture by chemical adsorption, and zeolite and silicagel adsorb moisture by physical adsorption.

Figure 3:
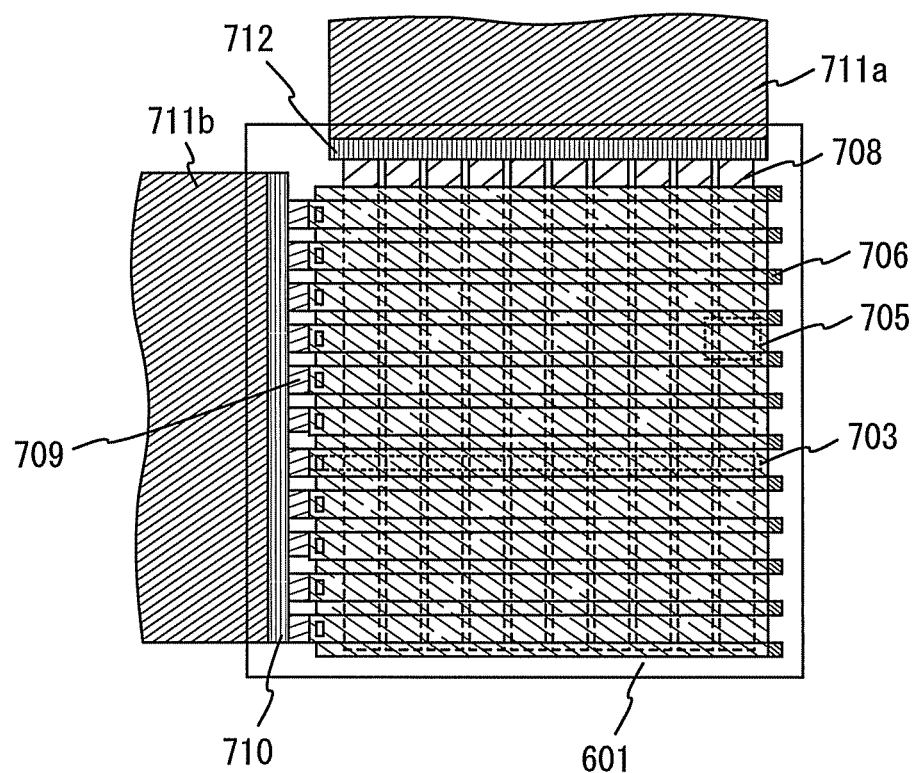
FIG. 3 illustrates an example of a light-emitting device according to one embodiment of the present invention.

FIG. 3 is a top view of the passive-matrix light-emitting device illustrated in FIGS. 2A to 2D that is provided with a flexible printed circuit (an FPC) and the like.

As illustrated in FIG. 3, in a pixel portion forming an image display, scanning lines and data lines are arranged to intersect with each other so that the scanning lines and the data lines are perpendicular to each other.

The first electrodes 603 in FIGS. 2A to 2D correspond to scan lines 703 in FIG. 3; the second electrodes 608 in FIGS. 2A to 2D correspond to data lines 708 in FIG. 3; and the inversely tapered partitions 606 correspond to partitions 706. The EL layers 607 illustrated in FIG. 2D are interposed between the data lines 708 and the scanning lines 703, and an intersection indicated by a region 705 corresponds to one pixel.

Note that the scanning lines 703 are electrically connected at their ends to connection wirings 709, and the connection wirings 709 are connected to an FPC 711b via an input terminal 710. In addition, the data lines 708 are connected to an FPC 711a via an input terminal 712.

An optical film such as a polarizing plate, a circularly polarizing plate (including an elliptically polarizing plate), a retardation plate (a quarter-wave plate or a half-wave plate), or a color filter may be provided as needed. Further, an anti-reflection film may be provided in addition to the polarizing plate or the circularly polarizing plate. By providing the anti-reflection film, anti-glare treatment can be carried out by which reflected light can be scattered by roughness of a surface so as to reduce reflection.

Although FIG. 3 illustrates the example in which a driver circuit is not provided over the substrate, an IC chip including a driver circuit may be mounted on the substrate.

When the IC chip is mounted, a data line side IC and a scanning line side IC, in each of which the driver circuit for transmitting a signal to a pixel portion is formed, are mounted on the periphery of (outside) the pixel portion. As a method for mounting an IC chip, a COG method, TCP, a wire bonding method, or the like can be used. The TCP is a TAB tape mounted with the IC, and the TAB tape is connected to a wiring over an element formation substrate to mount the IC. The data line side IC and the scanning line side IC may be formed over a silicon substrate, a silicon on insulator (SOI) substrate, a glass substrate, a quartz substrate, or a plastic substrate.

Figure 4A:
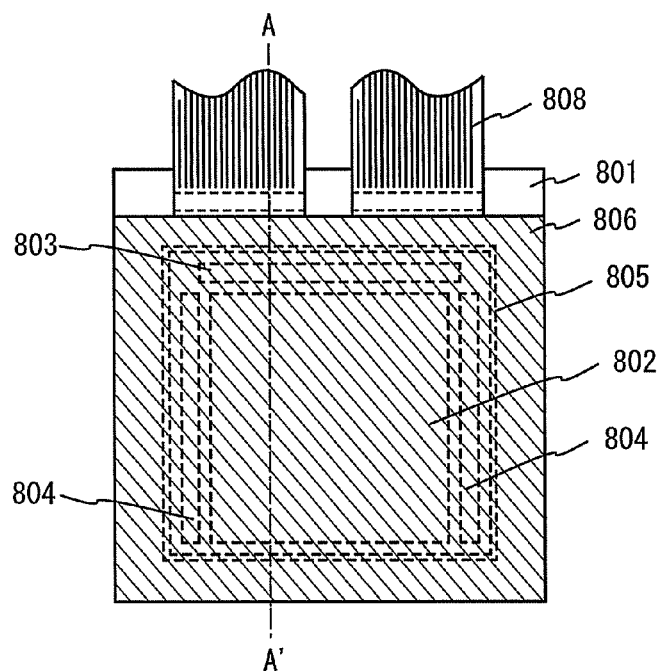
FIGS. 4A and 4B illustrate an example of a light-emitting device according to one embodiment of the present invention.
Figure 4B:
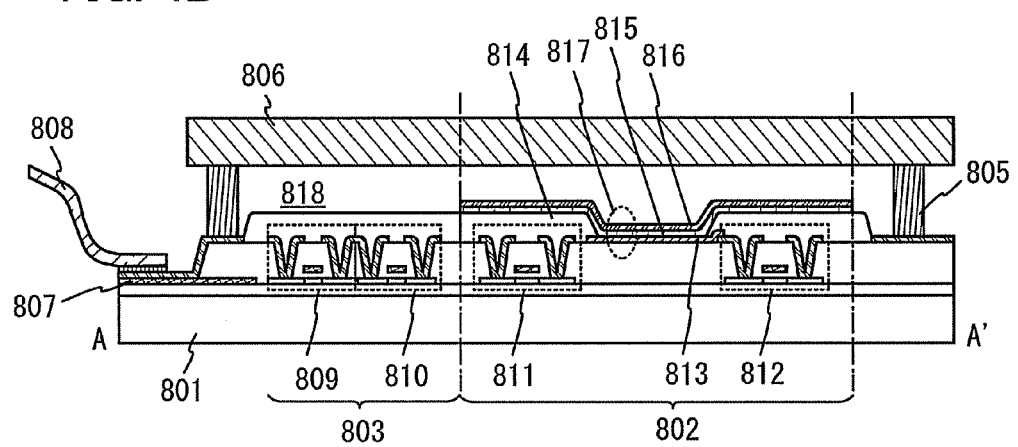

Next, an example of the active-matrix light-emitting device is described with reference to FIGS. 4A and 4B. FIG. 4A is a top view illustrating a light-emitting device and FIG. 4B is a cross-sectional view taken along dashed line A-A' in FIG. 4A. The active-matrix light-emitting device of this embodiment includes a pixel portion 802 provided over an element substrate 801, a driver circuit portion (a source-side driver circuit) 803, and a driver circuit portion (a gate-side driver circuit) 804. The pixel portion 802, the driver circuit portion 803 and the driver circuit portion 804 are sealed between the element substrate 801 and the sealing substrate 806 by the sealing material 805.

Over the element substrate 801, a lead wiring 807 for connecting an external input terminal through which a signal (e.g., a video signal, a clock signal, a start signal, a reset signal, or the like) or electric potential from the external is transmitted to the driver circuit portion 803 and the driver circuit portion 804 is provided. Here, an example is described in which an FPC 808 is provided as the external input terminal. Note that although only an FPC is illustrated here, a printed wiring board (PWB) may be attached thereto. In this specification, the light-emitting device includes in its category the light-emitting device itself and the light-emitting device on which the FPC or the PWB is mounted.

Next, a cross-sectional structure of the active-matrix light-emitting device is described with reference to FIG. 4B. Although the driver circuit portion 803, the driver circuit portion 804, and the pixel portion 802 are formed over the element substrate 801, the pixel portion 802 and the driver circuit portion 803 which is the source side driver circuit are illustrated in FIG. 4B.

In the driver circuit portion 803, an example including a CMOS circuit which is a combination of an n-channel TFT 809 and a p-channel TFT 810 is illustrated. Note that a circuit included in the driver circuit portion can be formed using various types of circuits such as a CMOS circuit, a PMOS circuit, or an NMOS circuit. In this embodiment, a driver-integrated type in which a driver circuit and the pixel portion are formed over the same substrate is shown; however, the present invention is not limited to this structure, and a driver circuit can be formed over a substrate that is different from the substrate over which a pixel portion is formed.

The pixel portion 802 has a plurality of pixels, each including a switching TFT 811, a current-controlling TFT 812, and an anode 813 electrically connected to a wiring (a source electrode or a drain electrode) of the current-controlling TFT 812. An insulator 814 is formed so as to cover an end portion of the anode 813. In this embodiment, the insulator 814 is formed using a positive photosensitive acrylic resin. Note that there is no particular limitation on structures of the TFTs such as the switching TFT 811 and the current-controlling TFT 812. For example, a staggered TFT or an inverted-staggered TFT may be used. In addition, a top-gate TFT or a bottom-gate TFT may be used. There is no particular limitation also on materials of a semiconductor used for the TFTs, and silicon or an oxide semiconductor such as oxide including indium, gallium, and zinc may be used. In addition, crystallinity of a semiconductor used for the TFT is not particularly limited either; an amorphous semiconductor or a crystalline semiconductor may be used.

A light-emitting element 817 includes an anode 813, an EL layer 815, and a cathode 816. Since the structure and materials for the light-emitting element are described in Embodiment 2, a detailed description is omitted in this embodiment. Note that the anode 813, the EL layer 815, and the cathode 816 in FIGS. 4A and 4B correspond to the first electrode 102 (the anode), the EL layer 103, and the second electrode 104 (the cathode) in Embodiment 2, respectively. Although not illustrated, the cathode 816 is electrically connected to the FPC 808 which is an external input terminal.

The insulator 814 is provided at an end portion of the anode 813. In addition, in order that the cathode 816 that is formed over the insulator 814 at least favorably covers the insulator 814, the insulator 814 is preferably formed so as to have a curved surface with curvature at an upper end portion or a lower end portion. For example, it is preferable that the upper end portion or the lower end portion of the insulator 814 have a curved surface with a radius of curvature (0.2 μm to 3 μm). The insulator 814 can be formed using an organic compound such as a negative photosensitive resin which becomes insoluble in an etchant by light or a positive photosensitive resin which becomes soluble in an etchant by light, or an inorganic compound such as silicon oxide or silicon oxynitride.

Although the cross-sectional view of FIG. 4B illustrates only one light-emitting element 817, a plurality of light-emitting elements are arranged in matrix in the pixel portion 802. For example, light-emitting elements that emit light of three kinds of colors (R, G, and B) are formed in the pixel portion 802, so that a light-emitting device capable of full color display can be obtained. Alternatively, a light-emitting device which is capable of full color display may be manufactured by a combination with color filters.

The light-emitting element 817 is formed in a space 818 that is surrounded by the element substrate 801, the sealing substrate 806, and the sealing material 805. The space 818 may be filled with a rare gas, a nitrogen gas, or the sealing material 805.

The sealing material 805 is preferably a material that transmits moisture and oxygen as little as possible, such as an epoxy-based resin. As the sealing substrate 806, a glass substrate, a quartz substrate, a plastic substrate formed of FRP (fiberglass-reinforced plastics), PVF (polyvinyl fluoride), polyester, acrylic, or the like can be used.

In the above manner, the active-matrix light-emitting device can be obtained.

Embodiment 5

In this embodiment, specific examples of electronic devices and lighting devices each of which is manufactured using a light-emitting device described in any of the above embodiments are described with reference to FIGS. 5A to 5E and FIG. 6.

Examples of electronic devices to which the present invention can be applied include a television set (also referred to as a television or a television receiver), a monitor of a computer or the like, a digital camera, a digital video camera, a digital photo frame, a mobile phone, a portable game machine, a portable information terminal, an audio reproducing device, a game machine (e.g., a pachinko machine or a slot machine), a housing of a game machine, and the like. Some specific examples of these electronic devices and lighting devices are illustrated in FIGS. 5A to 5E and FIG. 6.

Figure 5A:
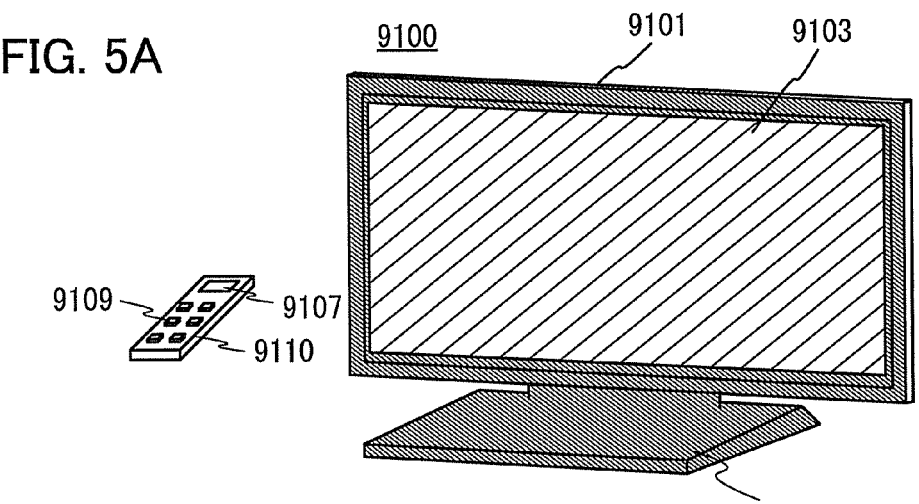
FIGS. 5A to 5E illustrate examples of electronic devices and a lighting device according to one embodiment of the present invention.

FIG. 5A illustrates a television set 9100. In the television set 9100, a display portion 9103 is incorporated in a housing 9101. A light-emitting device manufactured using one embodiment of the present invention can be used in the display portion 9103, so that an image can be displayed on the display portion 9103. Note that the housing 9101 is supported by a stand 9105 here.

The television set 9100 can be operated with an operation switch of the housing 9101 or a separate remote controller 9110. Channels and volume can be controlled with an operation key 9109 of the remote controller 9110 so that an image displayed on the display portion 9103 can be controlled. Furthermore, the remote controller 9110 may be provided with a display portion 9107 for displaying data output from the remote controller 9110.

The television set 9100 illustrated in FIG. 5A is provided with a receiver, a modem, and the like. With the receiver, the television set 9100 can receive a general television broadcast. Further, when the television set 9100 is connected to a communication network by wired or wireless connection via the modem, one-way (from a transmitter to a receiver) or two-way (between a transmitter and a receiver or between receivers) data communication can be performed.

Since a light-emitting device manufactured using one embodiment of the present invention has a favorable chromaticity, the television set including the light-emitting device in the display portion 9103 can display an image with improved image quality as compared with conventional images.

Figure 5B:
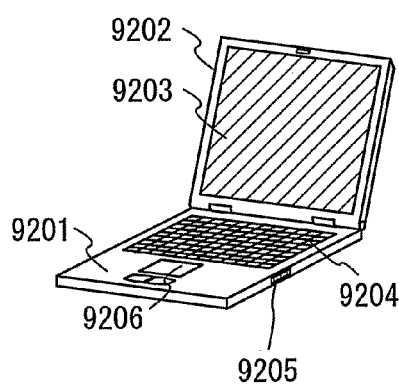

FIG. 5B illustrates a computer which includes a main body 9201, a housing 9202, a display portion 9203, a keyboard 9204, an external connection port 9205, a pointing device 9206, and the like. The computer is manufactured using a light-emitting device manufactured using one embodiment of the present invention for the display portion 9203.

Since a light-emitting device manufactured using one embodiment of the present invention has a favorable chromaticity, the computer including the light-emitting device in the display portion 9203 can display an image with improved image quality as compared with conventional images.

Figure 5C:
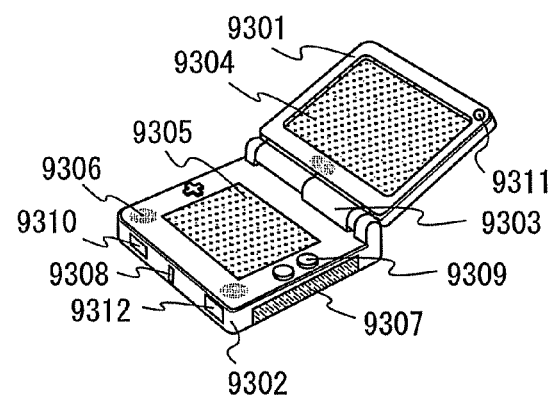

FIG. 5C illustrates a portable game machine including two housings, a housing 9301 and a housing 9302 which are jointed with a connector 9303 so as to be opened and closed. A display portion 9304 is incorporated in the housing 9301, and a display portion 9305 is incorporated in the housing 9302. In addition, the portable game machine illustrated in FIG. 5C includes an input means such as operation keys 9309, a connection terminal 9310, a sensor 9311 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 9312. The portable game machine may further be provided with a speaker portion 9306, a recording medium insertion portion 9307, an LED lamp 9308, and the like. Needless to say, the structure of the portable game machine is not limited to the above, and it is acceptable as long as the light-emitting device manufactured using one embodiment of the present invention is used for one or both of the display portion 9304 and the display portion 9305.

The portable game machine illustrated in FIG. 5C has a function of reading a program or data stored in a recording medium to display it on the display portion, and a function of sharing information with another portable game machine by wireless communication. Note that a function of the portable game machine illustrated in FIG. 5C is not limited to the above, and the portable game machine can have a variety of functions.

Since a light-emitting device manufactured using one embodiment of the present invention has a favorable chromaticity, the portable game machine including the light-emitting device in the display portions (9304 and 9305) can display an image with improved image quality as compared with conventional images.

Figure 5D:
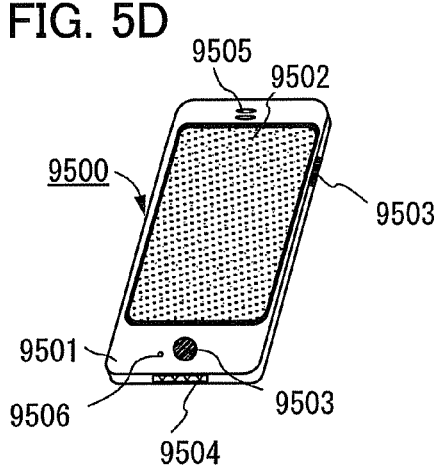

FIG. 5D illustrates an example of a mobile phone. A mobile phone 9500 is provided with a display portion 9502 incorporated in a housing 9501, an operation button 9503, an external connection port 9504, a speaker 9505, a microphone 9506, and the like. Note that the mobile phone 9500 is manufactured using a light-emitting device manufactured using one embodiment of the present invention for the display portion 9502.

Users can input data, make a call, or text a message by touching the display portion 9502 of the mobile phone 9500 illustrated in FIG. 5D with their fingers or the like.

There are mainly three screen modes for the display portion 9502. The first mode is a display mode mainly for displaying images. The second mode is an input mode mainly for inputting data such as text. The third mode is a display-and-input mode in which two modes of the display mode and the input mode are combined.

For example, in the case of making a call or text messaging, a text input mode mainly for inputting text is selected for the display portion 9502 so that characters displayed on a screen can be input. In this case, a keyboard or number buttons are preferably displayed on almost the entire screen of the display portion 9502.

By providing a detection device which includes a sensor for detecting inclination, such as a gyroscope or an acceleration sensor, inside the mobile phone 9500, the direction of the mobile phone 9500 (whether the mobile phone 9500 is placed horizontally or vertically for a landscape mode or a portrait mode) is determined so that display on the screen of the display portion 9502 can be automatically switched.

In addition, the screen mode is switched by touching the display portion 9502 or operating the operation button 9503 of the housing 9501. Alternatively, the screen modes can be switched depending on kinds of images displayed in the display portion 9502. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 9502 is not performed within a specified period of time while a signal detected by an optical sensor in the display portion 9502 is detected, the screen mode may be controlled so as to be switched from the input mode to the display mode.

The display portion 9502 can also function as an image sensor. For example, an image of a palm print, a fingerprint, or the like is taken by touching the display portion 9502 with the palm or the finger, whereby personal authentication can be performed. Further, by providing a backlight or a sensing light source which emits a near-infrared light in the display portion, an image of a finger vein, a palm vein, or the like can be taken.

Since a light-emitting device manufactured using one embodiment of the present invention has a favorable chromaticity, the mobile phone including the light-emitting device in the display portion 9502 can display an image with improved image quality as compared with conventional images.

Figure 5E:
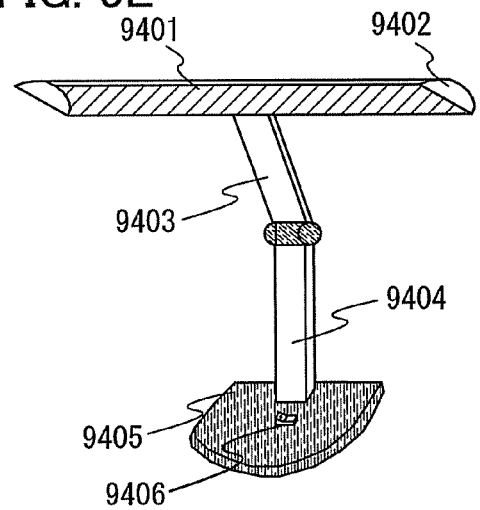

FIG. 5E illustrates a tabletop lighting device including a lighting portion 9401, a shade 9402, an adjustable arm 9403, a support 9404, a base 9405, and a power supply switch 9406. The tabletop lighting device is manufactured using a light-emitting device manufactured using one embodiment of the present invention for the lighting portion 9401. Note that the modes of the lighting device is not limited to tabletop lighting devices, but include ceiling-fixed lighting devices, wall-hanging lighting devices, portable lighting devices, and the like.

Figure 6:
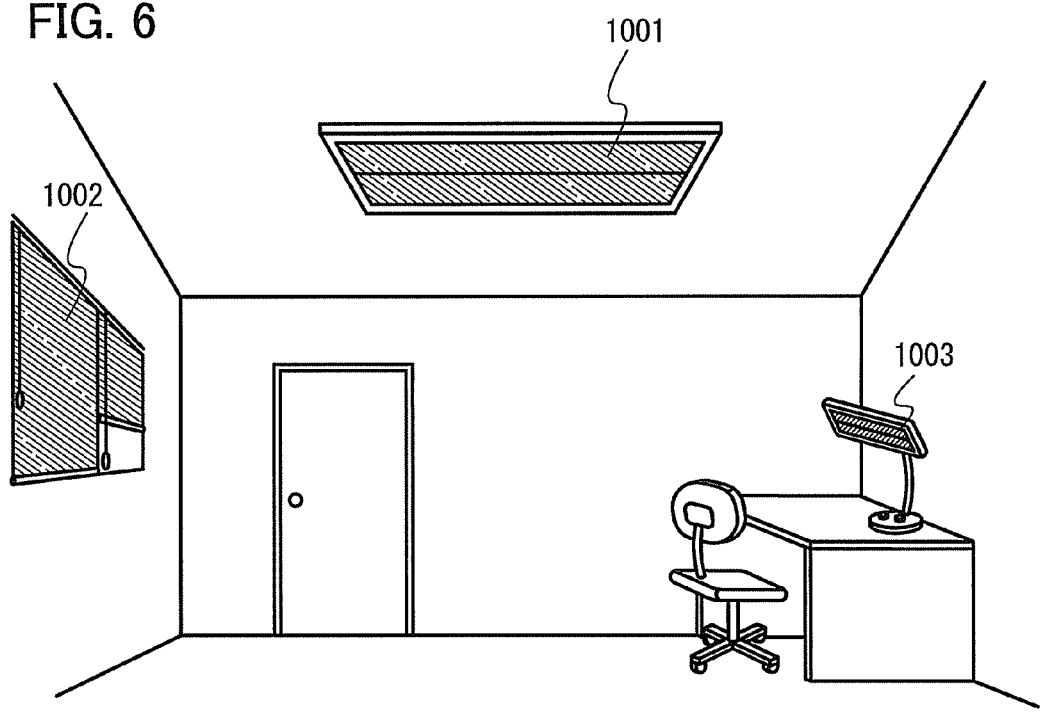
FIG. 6 illustrates examples of lighting devices according to one embodiment of the present invention.

FIG. 6 illustrates an example in which the light-emitting device manufactured using one embodiment of the present invention is used for an indoor lighting device 1001. Since the light-emitting device manufactured using one embodiment of the present invention can have a large area, the light-emitting device can be used as a lighting apparatus having a large area. In addition, the light-emitting device described in the above embodiments can be made thin and thus can be used as a roll-up type lighting device 1002. As illustrated in FIG. 6, a tabletop lighting device 1003 illustrated in FIG. 5E may be used in a room provided with the indoor lighting device 1001.

In the above manner, electronic devices and lighting devices can be provided using the light-emitting device manufactured using one embodiment of the present invention. The scope of application of the light-emitting device manufactured using one embodiment of the present invention is so wide that it can be applied to a variety of fields of electronic devices and lighting devices.

Example 1

Synthesis Example 1

In this example, a synthesis example of an organometallic complex bis[5-(1,1-difluoroethyl)-3,4-diphenyl-4H-1,2,4- triazolato](picolinato)iridium(III) (abbreviation: [Ir(MCF₂ptz)₂(pic)]) represented by a structural formula below (Structural Formula (108) in Embodiment 1) is specifically described.

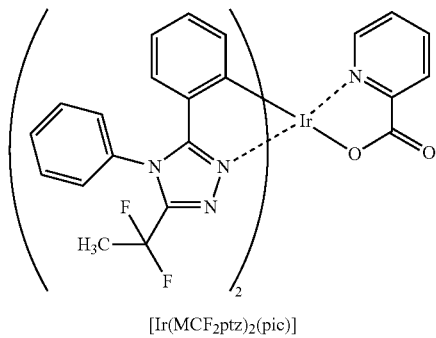

[Ir(MCF₂ptz)₂(pic)]

Step 1: Synthesis of N-[(ethylsulfanyl)phenylmethylidene]aniline

First, 3.2 g of sodium ethoxide, 10 g of N-phenylthiobenzamide, and 60 mL of ethanol were put in a 300 mL three-neck flask, and stirred at room temperature for 1 hour. Then, 3.7 mL of iodoethane was added to this mixture, and the mixture was heated and stirred at 60° C. for 6 hours to be reacted. After the reaction, ethanol was distilled off under a reduced pressure to give an oily substance. This oily substance was dissolved in dichloromethane, and washed with water and then a saturated aqueous solution of sodium hydrogen carbonate. Then, anhydrous magnesium sulfate was added to the resulting organic layer for drying. The resulting mixture was subjected to gravity filtration, and the filtrate was concentrated, so that N-[(ethylsulfanyl)phenylmethylidene]aniline was prepared (a brown oily substance, crude yield: 110%). The synthesis scheme of Step 1 is shown by (a-1).

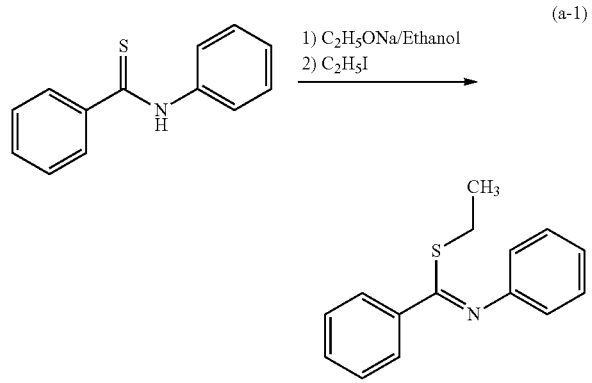

Step 2: Synthesis of 3-(1,1-difluoroethyl)-4,5-diphenyl-4H-1,2,4-triazole (abbreviation: HMCF₂ptz)

Next, 0.54 g (11 mmol) of hydrazine monohydrate and 10 mL of ethanol were put in a 100 mL three-neck flask and stirred at −10° C. for 15 minutes. Then, 1.5 g (11 mmol) of ethyl 2,2-difluoropropionate was dripped to this mixed solution at −10° C. little by little, and the solution was stirred for 48 hours while the temperature was increased to room temperature. Then, 2.6 g (11 mmol) of N-[(ethylsulfanyl)phenylmethylidene]aniline prepared in Step 1 and 20 mL of 1-butanol were added to this mixed solution, and the mixed solution was refluxed at 110° C. for 8 hours. After the reflux, the solvent was distilled off under a reduced pressure to give an oily substance. The given oily substance was purified by silica gel column chromatography. As developing solvents, first, toluene was used, and then ethyl acetate was used. The obtained fraction was concentrated to give a solid. This solid was recrystallized from a mixed solvent of ethanol and hexane, so that 3-(1,1-difluoroethyl)-4,5-diphenyl-4H-1,2,4-triazole (abbreviation: HMCF₂ptz) was prepared (a white solid, yield: 27%). The synthesis scheme of Step 2 is shown by (b-1).

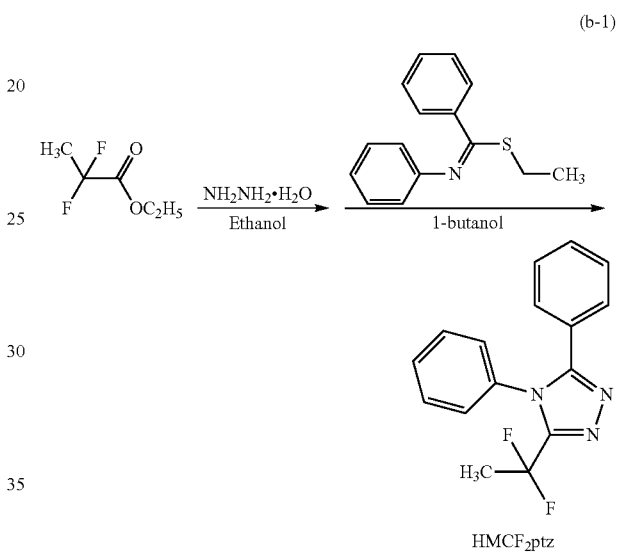

Step 3: Synthesis of bis[5-(1,1-difluoroethyl)-3,4-diphenyl-4H-1,2,4-triazolato](picolinato)iridium(III) (abbreviation: [Ir(MCF₂ptz)₂(pic)])

Next, 0.81 g (2.9 mmol) of the ligand HMCF₂ptz prepared in Step 2, 0.41 g (1.4 mmol) of iridium chloride hydrate (IrCl₃.H₂O), 15 mL of 2-ethoxyethanol, and 5 mL of water were put in a 50 mL flask provided with a reflux pipe, and the air in the flask was replaced by argon. Irradiation with microwaves for 30 minutes was performed on this reaction container to cause reaction. After a predetermined time, this reacted solution was concentrated, so that a crude product of a chlorine-bridged binuclear complex of iridium was given as a brown oily substance. The given oily substance, 0.70 g (5.7 mmol) of picolinic acid, 0.60 g (5.7 mmol) of sodium carbonate, and 15 mL of dichloromethane were put in a 50 mL recovery flask, and the air in the flask was replaced by argon. Irradiation with microwaves for 30 minutes was performed on this reaction container to cause reaction by heat. Note that the irradiation with microwaves was performed using a microwave synthesis system (Discover manufactured by CEM Corporation). Then, this mixture was washed with water, and anhydrate magnesium sulfate was added to the resulting organic layer for drying. After the drying, this mixture was subjected to gravity filtration and the obtained filtrate was concentrated. The obtained residue was recrystallized from a mixed solvent of ethyl acetate and hexane, so that the organometallic complex [Ir(MCF$_2$ptz)$_2$(pic)] was prepared (yellow powder, yield: 33%). The synthesis scheme of Step 3 is shown by (c-1).

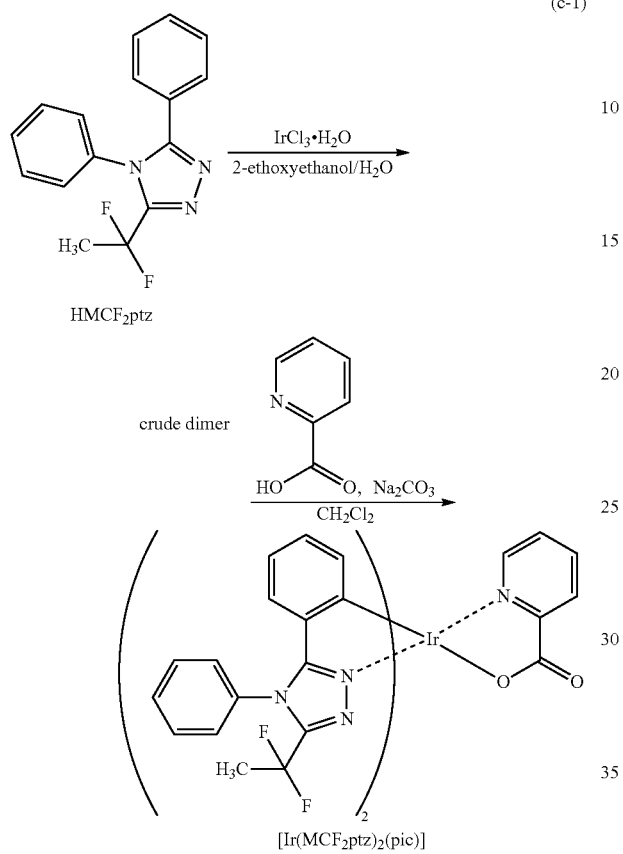

[Ir(MCF$_2$ptz)$_2$(pic)]

Figure 7:
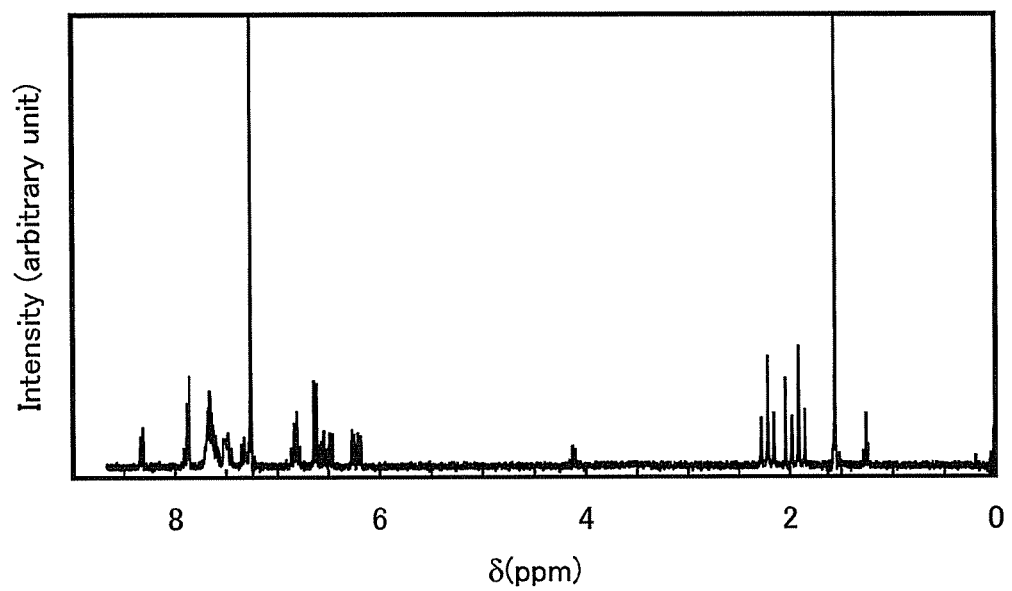
FIG. 7 shows a $^1$H-NMR spectrum of [Ir(MCF$_2$ptz)$_2$(pic)].

An analysis result by nuclear magnetic resonance spectrometry ($^1$H-NMR) of the yellow powder prepared in Step 3 is shown below. The $^1$H-NMR spectrum is shown in FIG. 7. From the results, it is found that the organometallic complex [Ir(MCF$_2$ptz)$_2$(pic)] which is one embodiment of the present invention represented by Structural Formula (108) was prepared in Synthesis Example 1.

$^1$H-NMR. δ (CDCl$_3$): 1.92 (t, 3H), 2.22 (t, 3H), 6.20 (dd, 1H), 6.26 (dd, 1H), 6.55 (m, 4H), 6.81 (m, 2H), 7.31 (dd, 1H), 7.51 (m, 3H), 7.64 (m, 7H), 7.89 (m, 2H), 8.32 (d, 1H).

Figure 8:
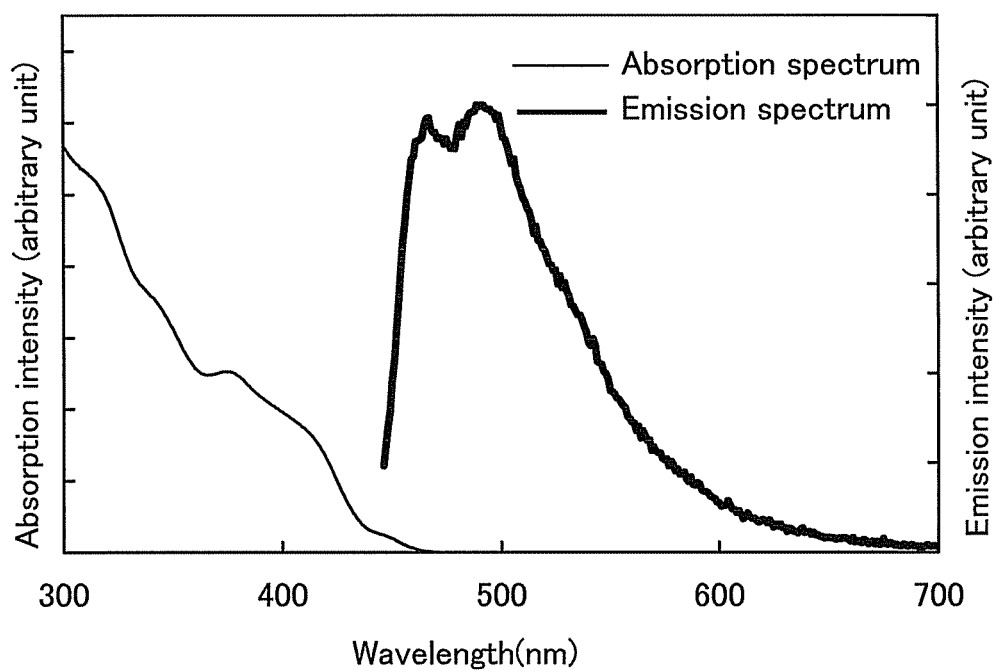
FIG. 8 shows an absorption spectrum and an emission spectrum of [Ir(MCF$_2$ptz)$_2$(pic)] in a dichloromethane solution.

Next, an ultraviolet-visible absorption spectrum (an absorption spectrum) and an emission spectrum of [Ir(MCF$_2$ptz)$_2$(pic)] in dichloromethane solutions were measured. The absorption spectrum was measured with the use of an ultraviolet-visible light spectrophotometer (V-550 manufactured by JASCO Corporation) in the state where a dichloromethane solution (0.068 mmol/L) was put in a quartz cell at room temperature. The emission spectrum was measured with the use of a fluorescence spectrophotometer (FS920 manufactured by Hamamatsu Photonics Corporation) in the state where a degassed dichloromethane solution (0.068 mmol/L) was put in a quartz cell at room temperature. FIG. 8 shows measurement results of the absorption spectrum and emission spectrum. The horizontal axis represents wavelength, and the vertical axis represents absorption intensity and emission intensity. In FIG. 8, two solid lines are shown; a thin line represents the absorption spectrum, and a thick line represents the emission spectrum. Note that the absorption spectrum in FIG. 8 is a result obtained by subtraction of the absorption spectrum of only dichloromethane that was put in a quartz cell from the measured absorption spectrum of the dichloromethane solution (0.068 mmol/L) in a quartz cell.

As shown in FIG. 8, the organometallic complex [Ir(MCF$_2$ptz)$_2$(pic)] which is one embodiment of the present invention has peaks of emission at 469 nm and 489 nm, and light-blue light was observed from the dichloromethane solution.

Example 2

Synthesis Example 2

In this example, a synthesis example of an organometallic complex bis(3,4-diphenyl-5-trifluoromethyl-4H-1,2,4-triazolato)(picolinato)iridium(III) (abbreviation: [Ir(CF$_3$ptz)$_2$(pic)]) represented by a structural formula below (Structural Formula (100) in Embodiment 1) is specifically described.

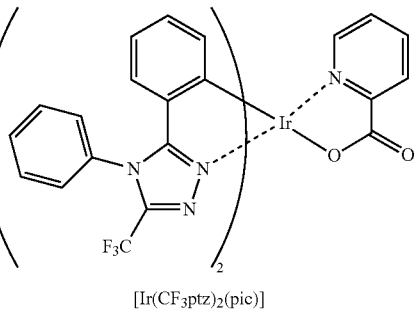

[Ir(CF$_3$ptz)$_2$(pic)]

Step 1: Synthesis of 3,4-diphenyl-5-trifluoromethyl-4H-1,2,4-triazole (abbreviation: HCF$_3$ptz)

First, 1.8 g of ethyl trifluoroacetate and 50 mL of 1-butanol were put in a three-neck flask, and the air in the flask was replaced by nitrogen. After that, the mixture was stirred at 0° C. for 10 minutes, and 0.397 g of hydrazine monohydrate was dripped to the mixed solution. This mixed solution was stirred at 0° C. for 20 minutes, and then stirred at room temperature for 1 hour to be reacted. After the reaction, 3.0 g of N-[(ethylsulfanyl)phenylmethylidene]aniline was further added to the mixed solution, and the solution was heated and stirred at 120° C. for 5 hours to be reacted. The mixed solution after the reaction was cooled down to room temperature and filtered, so that filtrate was obtained. The obtained filtrate was concentrated to give a solid. This solid was washed with hexane, so that the triazole derivative HCF$_3$ptz was prepared (yield: 26%). The synthesis scheme of Step 1 is shown by (a-2).

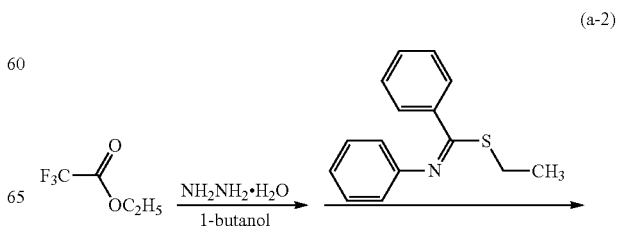

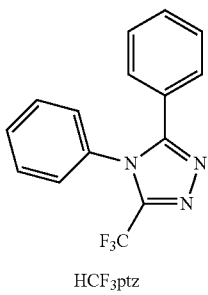

HCF$_3$ptz

Step 2: Synthesis of di-μ-chloro-bis[bis(3,4-diphenyl-5-trifluoromethyl-4H-1,2,4-triazolato)]iridium(III) (abbreviation: [Ir(CF$_3$ptz)$_2$Cl]$_2$)

Next, 12 mL of 2-ethoxyethanol, 4 mL of water, 0.87 g of HCF$_3$ptz prepared in Step 1, and 0.43 g of iridium chloride hydrate (IrCl$_3$·H$_2$O) (manufactured by Sigma-Aldrich Corp.) were put in a recovery flask provided with a reflux pipe, and the air in the flask was replaced by argon. Then, irradiation with microwaves (2.45 GHz, 100 W) for 30 minutes was performed to cause reaction. Note that the irradiation with microwaves was performed using a microwave synthesis system (Discover manufactured by CEM Corporation). Then, the reacted solution was filtered, and the filtrate was concentrated and dried. The obtained residue was recrystallized from ethanol, so that the binuclear complex [Ir(CF$_3$ptz)$_2$Cl]$_2$ was prepared (brown powder, yield: 99%). The synthetic scheme of Step 2 is shown by (b-2).

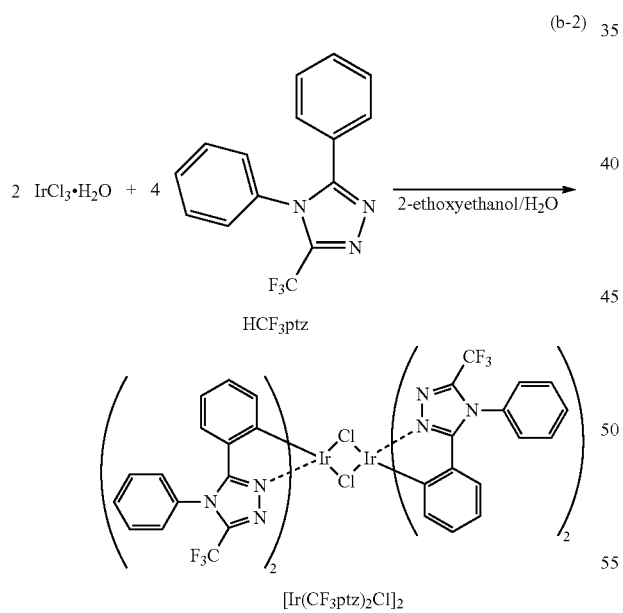

(b-2)

Step 3: Synthesis of bis(3,4-diphenyl-5-trifluoromethyl-4H-1,2,4-triazolato)(picolinato)iridium(III) (abbreviation: [Ir(CF$_3$ptz)$_2$(pic)])

Next, 15 mL of dichloromethane, 1.20 g of the binuclear complex [Ir(CF$_3$ptz)$_2$Cl]$_2$ prepared in Step 2, and 0.74 g of picolinic acid were put in a recovery flask provided with a reflux pipe, and the air in the flask was replaced by argon. Then, irradiation with microwaves (2.45 GHz, 100 W) for 30 minutes was performed to cause reaction. Then, the reacted solution was filtered. The obtained residue was dissolved in dichloromethane and filtration was performed to remove insoluble matter, and then the filtrate was concentrated and dried. The obtained residue was purified by silica gel column chromatography which uses ethyl acetate as a developing solvent. Further, recrystallization with a dichloromethane solvent was performed, so that the organometallic complex [Ir(CF$_3$ptz)$_2$(pic)] which is one embodiment of the present invention was prepared (yellow powder, yield: 18%). The synthesis scheme of Step 3 is shown by (c-2).

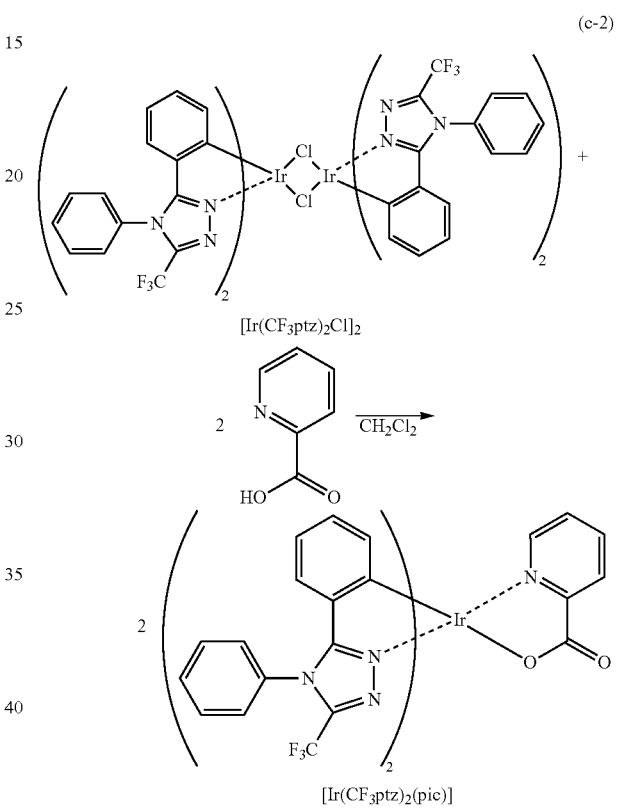

(c-2)

Figure 9:
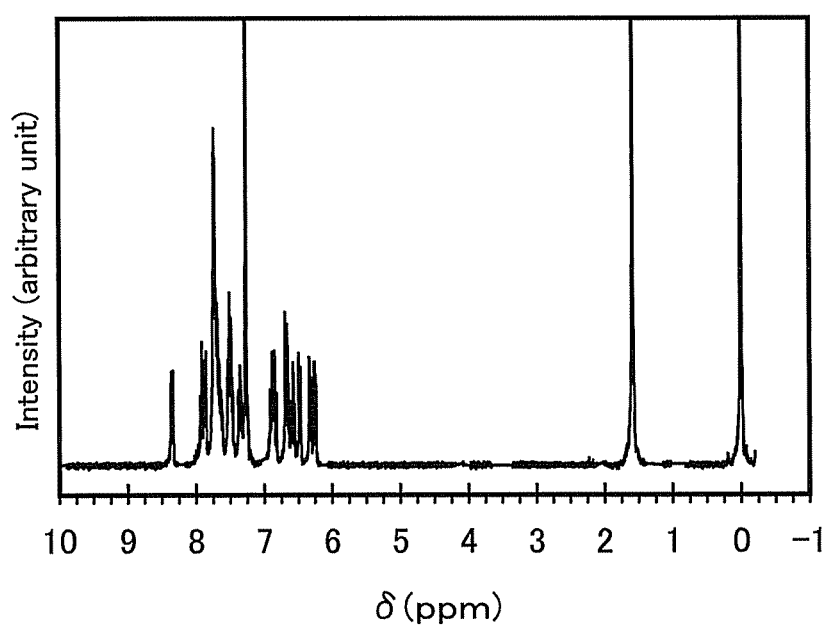
FIG. 9 shows a $^1$H-NMR spectrum of [Ir(CF$_3$ptz)$_2$(pic)].

An analysis result by nuclear magnetic resonance spectrometry ($^1$H-NMR) of the yellow powder prepared in Step 3 is shown below. The $^1$H-NMR spectrum is shown in FIG. 9. From the results, it is found that the organometallic complex [Ir(CF$_3$ptz)$_2$(pic)] which is one embodiment of the present invention represented by Structural Formula (100) was prepared in Synthesis Example 2.

$^1$H-NMR. δ (CDCl$_3$): 6.25 (d, 1H), 6.32 (d, 1H), 6.48 (d, 1H), 5.58 (dd, 1H), 6.67 (m, 2H), 6.86 (m, 2H), 7.35 (dt, 1H), 7.51 (m, 3H), 7.61-7.74 (m, 7H), 7.89 (m, 2H), 8.35 (d, 1H).

Figure 10:
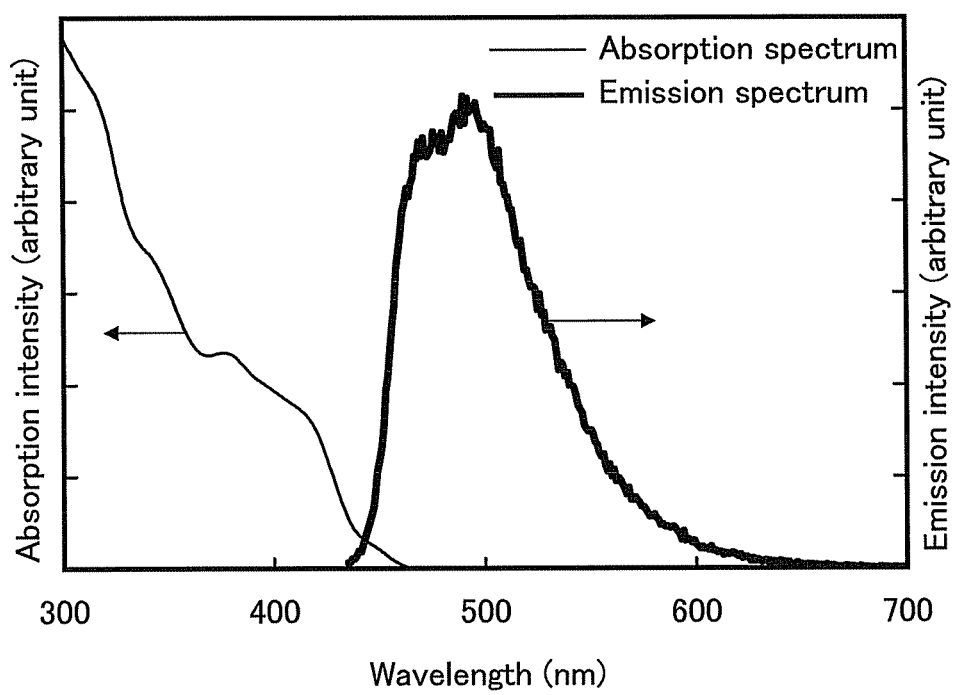
FIG. 10 shows an absorption spectrum and an emission spectrum of [Ir(CF$_3$ptz)$_2$(pic)] in a dichloromethane solution.

Next, an ultraviolet-visible absorption spectrum (an absorption spectrum) and an emission spectrum of [Ir(CF$_3$ptz)$_2$(pic)] in dichloromethane solutions were measured. The absorption spectrum was measured with the use of an ultraviolet-visible light spectrophotometer (V-550 manufactured by JASCO Corporation) in the state where a dichloromethane solution (0.064 mmol/L) was put in a quartz cell at room temperature. The emission spectrum was measured with the use of a fluorescence spectrophotometer (FS920 manufactured by Hamamatsu Photonics Corporation) in the state where a degassed dichloromethane solution (0.39 mmol/L) was put in a quartz cell at room temperature. FIG. 10 shows measurement results of the absorption spectrum and emission spectrum. The horizontal axis represents wavelength, and the vertical axis represents absorption intensity and emission intensity. In FIG. 10, two solid lines are shown; a thin line represents the absorption spectrum, and a thick line represents the emission spectrum. Note that the absorption spectrum in FIG. 10 is a result obtained by subtraction of the absorption spectrum of only dichloromethane that was put in a quartz cell from the measured absorption spectrum of the dichloromethane solution (0.064 mmol/L) in a quartz cell.

As shown in FIG. 10, the organometallic complex [Ir(CF$_3$ptz)$_2$(pic)] which is one embodiment of the present invention has peaks of emission at 470 nm and 495 nm, and blue-green light was observed from the dichloromethane solution.

Example 3

Synthesis Example 3

In this example, a synthesis example of an organometallic complex tris[3-(4-fluorophenyl)-4-phenyl-5-trifluoromethyl-4H-1,2,4-triazolato]iridium(III) (abbreviation: [Ir(CF$_3$Fptz)$_3$]) represented by a structural formula below (Structural Formula (155) in Embodiment 1) is specifically described.

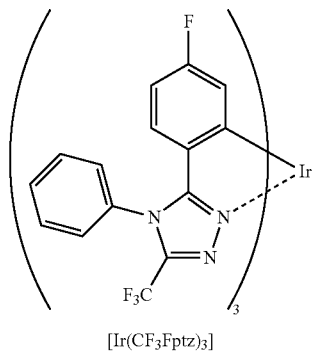

[Ir(CF$_3$Fptz)$_3$]

Step 1: Synthesis of 3-(4-fluorophenyl)-4-phenyl-5-trifluoromethyl-4H-1,2,4-triazole (abbreviation: HCF$_3$Fptz)

First, 3.0 g of ethyl trifluoroacetate and 10 mL of 1-butanol were put in a 100 mL three-neck flask and stirred with being cooled with ice for 10 minutes. After the stirring, 1.1 g of hydrazine monohydrate was added to this mixed solution, and the solution was stirred for 30 minutes while the temperature was increased to room temperature. Then, 5.1 g of ethyl N-phenyl-4-fluorobenzenecarboximidothioate was added to this reacted solution, and the reacted solution was heated and refluxed at 130° C. for 5 hours. After the reflux, 1-butanol was distilled off under a reduced pressure to give an oily substance. The given oily substance was purified by silica gel column chromatography. A mixed solvent of toluene:ethyl acetate=4:1 (v/v) was used as a developing solvent. The obtained fraction was concentrated to give a solid. This solid was recrystallized from a mixed solvent of ethanol and hexane, so that 3-(4-fluorophenyl)-4-phenyl-5-trifluoromethyl-4H-1,2,4-triazole (abbreviation: HCF$_3$Fptz) was prepared (a white solid, yield: 27%). The synthetic scheme of Step 1 is shown by (a-3).

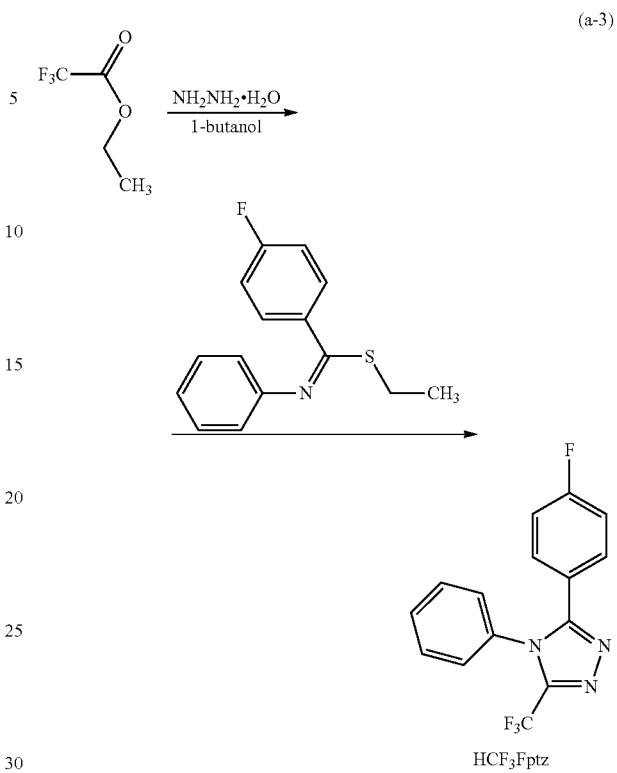

Step 2: Synthesis of tris[3-(4-fluorophenyl)-4-phenyl-5-trifluoromethyl-4H-1,2,4-triazolato]iridium (III) (abbreviation: [Ir(CF$_3$Fptz)$_3$])

Next, 1.61 g of the ligand HCF$_3$Fptz prepared in Step 1 and 0.51 g of tris(acetylacetonato)iridium(III) were put in a reaction container provided with a three-way cock, and the air in the reaction container was replaced by argon. Then, the mixture was heated at 250° C. for 44 hours to be reacted. The reactant was dissolved in dichloromethane and purified by silica gel column chromatography. A mixed solvent of dichloromethane:ethyl acetate=98:2 was used as a developing solvent. The obtained fraction was concentrated to give a solid. This solid was recrystallized from a mixed solvent of dichloromethane and hexane, so that the organometallic complex [Ir(CF$_3$Fptz)$_3$] was prepared (light-yellow powder, yield: 80%). The synthetic scheme of Step 2 is shown by (b-3).

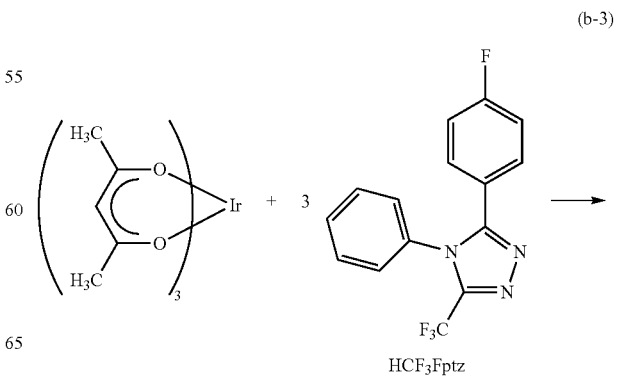

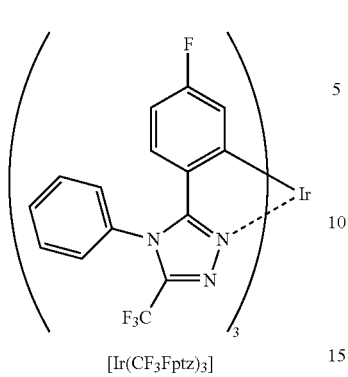

[Ir(CF₃Fptz)₃]

Figure 21:
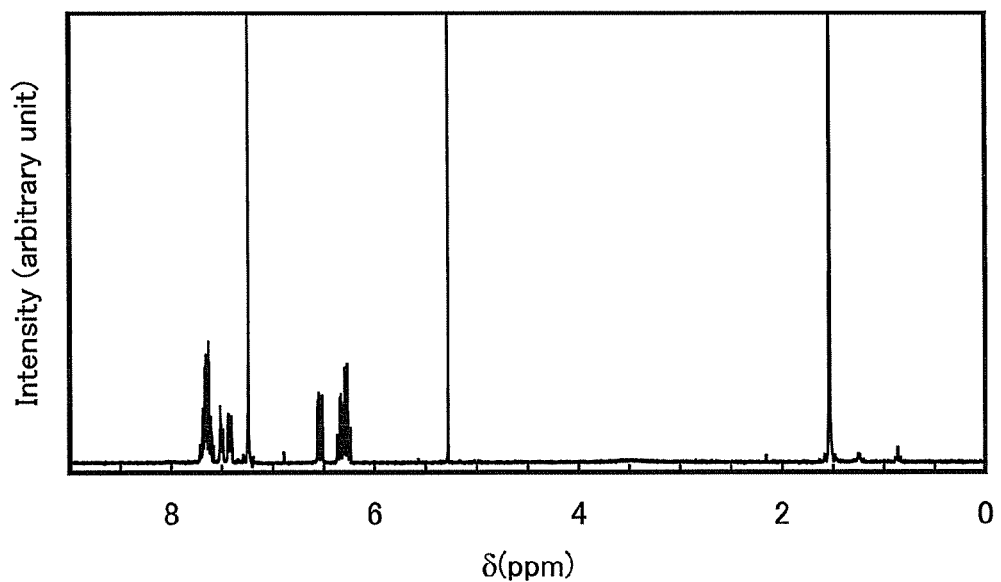
FIG. 21 shows a $^1$H-NMR spectrum of [Ir(CF$_3$Fptz)$_3$].

An analysis result by nuclear magnetic resonance spectroscopy ($^1$H-NMR) of the light-yellow powder prepared in Step 2 is shown below. The $^1$H-NMR spectrum is shown in FIG. 21. From the results, it is found that the organometallic complex [Ir(CF₃Fptz)₃] which is one embodiment of the present invention represented by Structural Formula (155) was prepared in Synthesis Example 3.

$^1$H-NMR. δ (CDCl₃): 6.30 (m, 6H), 6.54 (dd, 3H), 7.42 (d, 3H), 7.50 (m, 3H), 7.65 (m, 9H).

Figure 22:
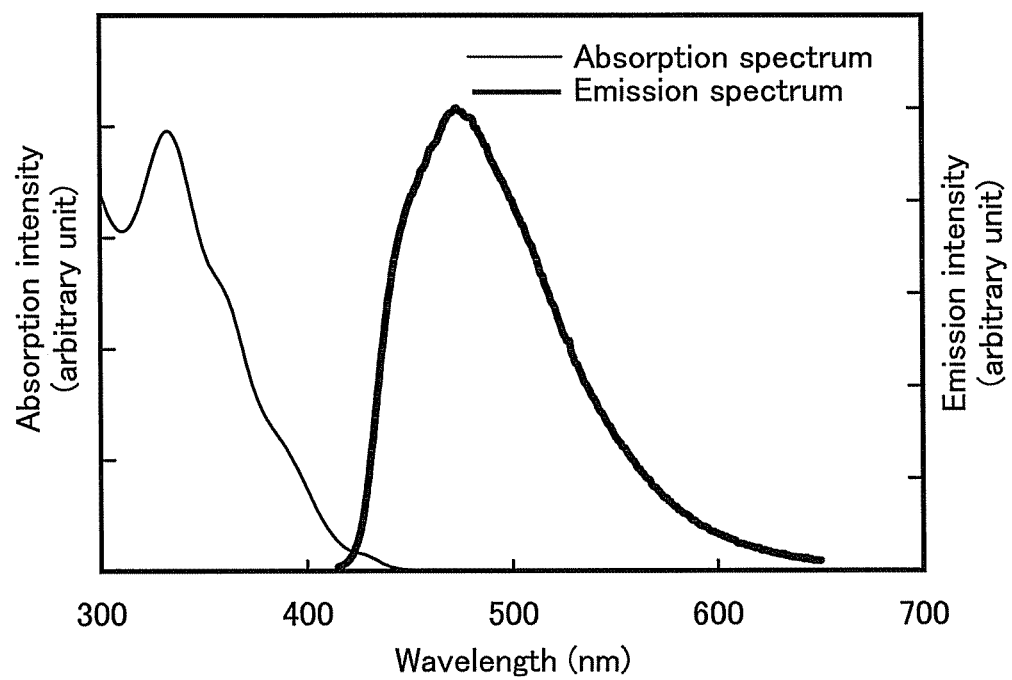
FIG. 22 shows an absorption spectrum and an emission spectrum of [Ir(CF$_3$Fptz)$_3$] in a dichloromethane solution.

Next, an ultraviolet-visible absorption spectrum (an absorption spectrum) and an emission spectrum of [Ir(CF₃Fptz)₃] in dichloromethane solutions were measured. The absorption spectrum was measured with the use of an ultraviolet-visible light spectrophotometer (V-550 manufactured by JASCO Corporation) in the state where a dichloromethane solution (0.081 mmol/L) was put in a quartz cell at room temperature. The emission spectrum was measured with the use of a fluorescence spectrophotometer (FS920 manufactured by Hamamatsu Photonics Corporation) in the state where a degassed dichloromethane solution (0.081 mmol/L) was put in a quartz cell at room temperature. FIG. 22 shows measurement results of the absorption spectrum and emission spectrum. The horizontal axis represents wavelength, and the vertical axis represents absorption intensity and emission intensity. In FIG. 22, two solid lines are shown; a thin line represents the absorption spectrum, and a thick line represents the emission spectrum. Note that the absorption spectrum in FIG. 22 is a result obtained by subtraction of the absorption spectrum of only dichloromethane that was put in a quartz cell from the measured absorption spectrum of the dichloromethane solution (0.081 mmol/L) in a quartz cell.

As shown in FIG. 22, the organometallic complex [Ir(CF₃Fptz)₃] which is one embodiment of the present invention has a peak of emission at 472 nm, and light-blue light was observed from the dichloromethane solution.

Example 4

In this example, a light-emitting element using the organometallic complex bis[5-(1,1-difluoroethyl)-3,4-diphenyl-4H-1,2,4-triazolato](picolinato)iridium(III) (abbreviation: [Ir(MCF₂ptz)₂(pic)]), which is represented by Structural Formula (108) in Embodiment 1, is described (the light-emitting element is referred to as Light-emitting Element 1 below). Structural formulas of part of materials used in this example are shown below.

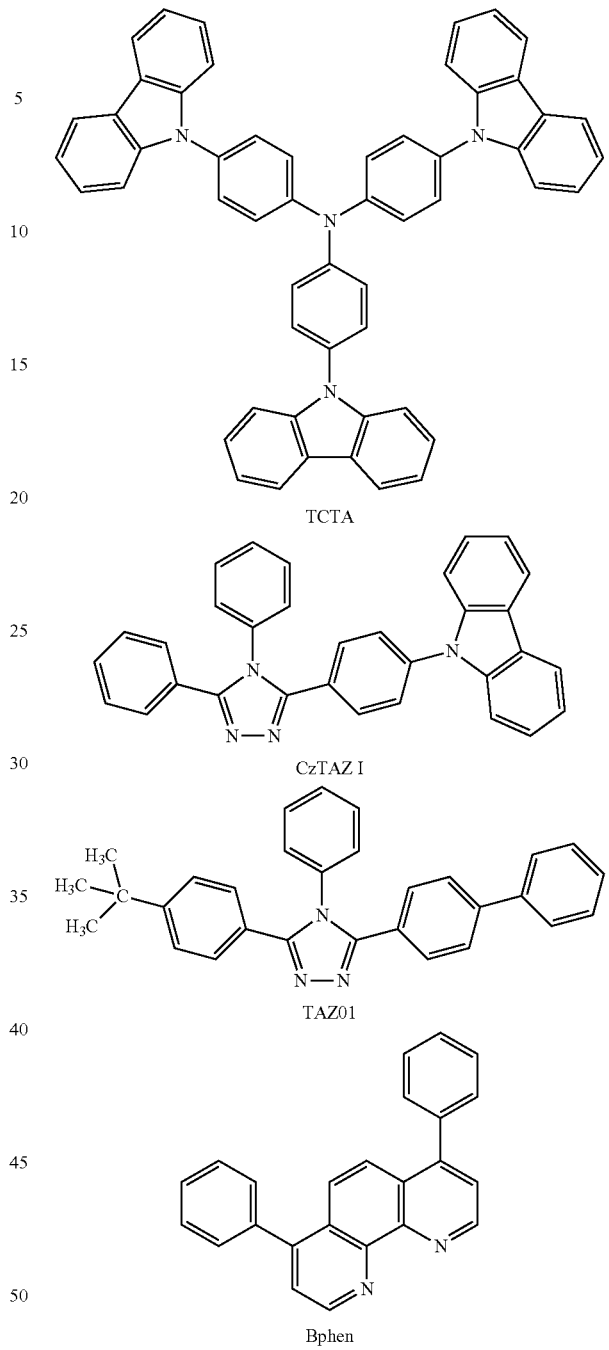

(Light-Emitting Element 1)

First, indium tin oxide containing silicon was deposited over a glass substrate by a sputtering method, so that a first electrode which functions as an anode was formed. The thickness of the first electrode was 110 nm and the electrode area was 2 mm×2 mm.

Next, the glass substrate over which the first electrode was formed was fixed to a substrate holder provided in a vacuum evaporation apparatus such that the side on which the first electrode was formed faced downward, and the pressure was reduced to approximately $10^{-4}$ Pa. After that, over the first electrode, a layer containing a composite material of an organic compound and an inorganic compound was formed by co-evaporation of 4,4',4"-tris(N-carbazolyl)triphenylamine (abbreviation: TCTA) and molybdenum(VI) oxide. The thickness of the layer containing a composite material was 50 nm, and the weight ratio of TCTA and molybdenum oxide was adjusted to 2:1 (=TCTA:molybdenum oxide). Note that the co-evaporation method means an evaporation method in which evaporation of a plurality of materials is performed using a plurality of evaporation sources at the same time in one treatment chamber.

Next, a 10-nm-thick TCTA layer was formed over the layer containing a composite material by an evaporation method using resistance heating, so that a hole-transport layer was formed.

Further, a 30-nm-thick light-emitting layer was formed over the hole-transport layer by co-evaporation of 9-[4-(4,5-diphenyl-4H-1,2,4-triazol-3-yl)phenyl]-9H-carbazole (abbreviation: CzTAZ I) and [Ir(MCF$_2$ptz)$_2$(pic)], which is the organometallic complex represented by Structural Formula (108) in Embodiment 1. Here, the weight ratio of CzTAZ I and [Ir(MCF$_2$ptz)$_2$(pic)] was adjusted to 1:0.06 (=CzTAZ I:[Ir(MCF$_2$ptz)$_2$(pic)]).

After that, over the light-emitting layer, a 10-nm-thick 3-(4-tert-butylphenyl)-4-phenyl-5-(4-biphenylyl)-1,2,4-triazole (abbreviation: TAZ 01) layer was formed by an evaporation method using resistance heating, and then a 20-nm-thick bathophenanthroline (abbreviation: BPhen) layer was formed by an evaporation method using resistance heating. In such a manner, an electron-transport layer in which a layer formed using TAZ 01 and a layer formed using BPhen are stacked was formed over the light-emitting layer.

Furthermore, a 1-nm-thick lithium fluoride layer was formed over the electron-transport layer, so that an electron-injection layer was formed.

Lastly, a 200-nm-thick aluminum layer was formed over the electron-injection layer by an evaporation method using resistance heating, so that a second electrode which functions as a cathode was formed. Through the above process, Light-emitting Element 1 was fabricated.

Figure 11:
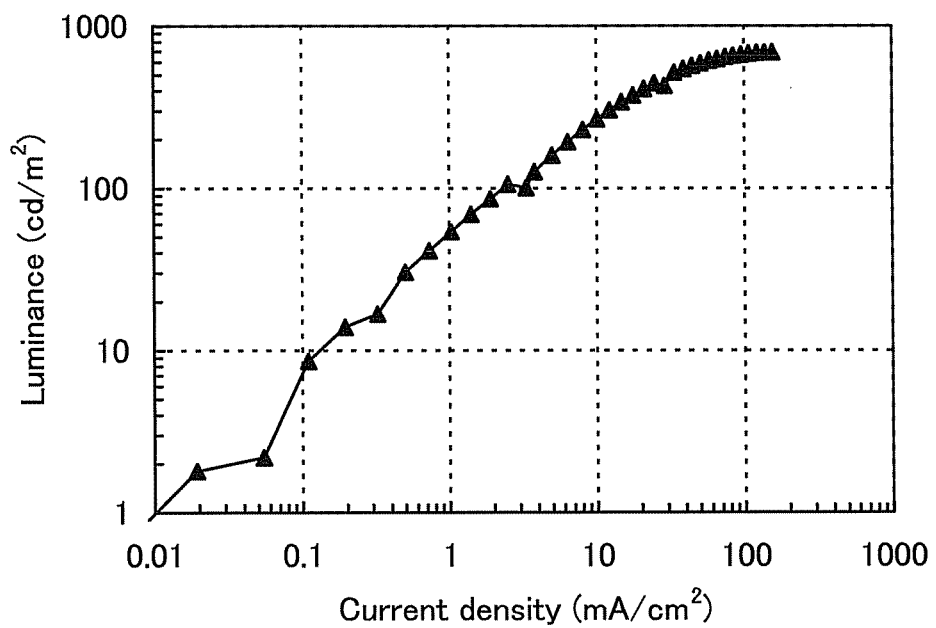
FIG. 11 shows current density vs. luminance characteristics of Light-emitting Element 1.
Figure 12:
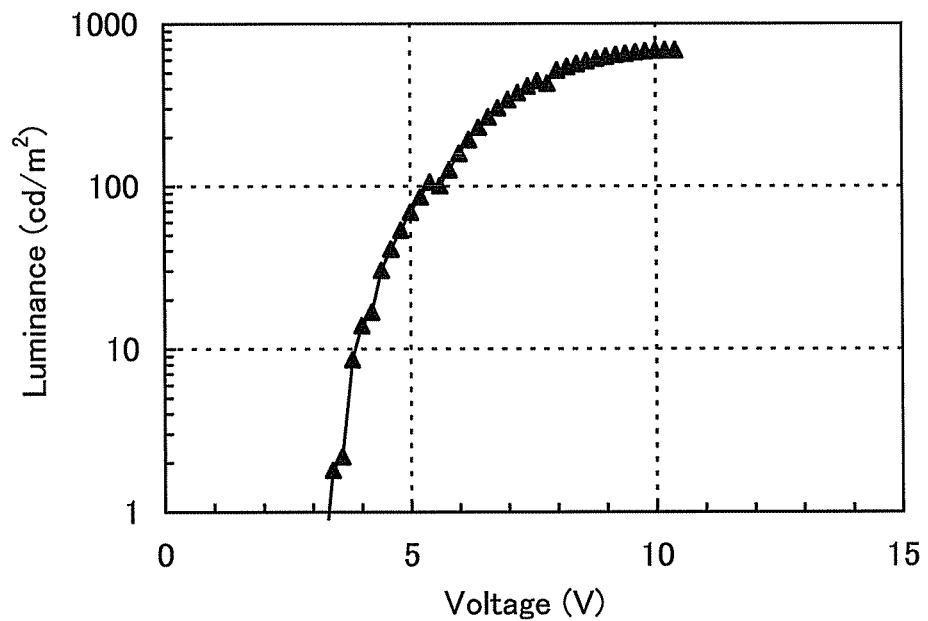
FIG. 12 shows voltage vs. luminance characteristics of Light-emitting Element 1.
Figure 13:
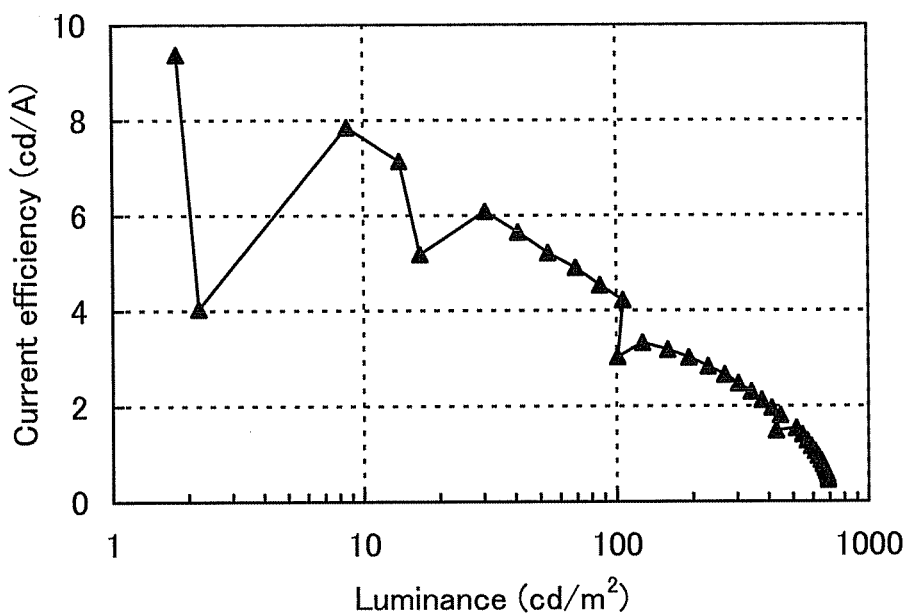
FIG. 13 shows luminance vs. current efficiency characteristics of Light-emitting Element 1.
Figure 14:
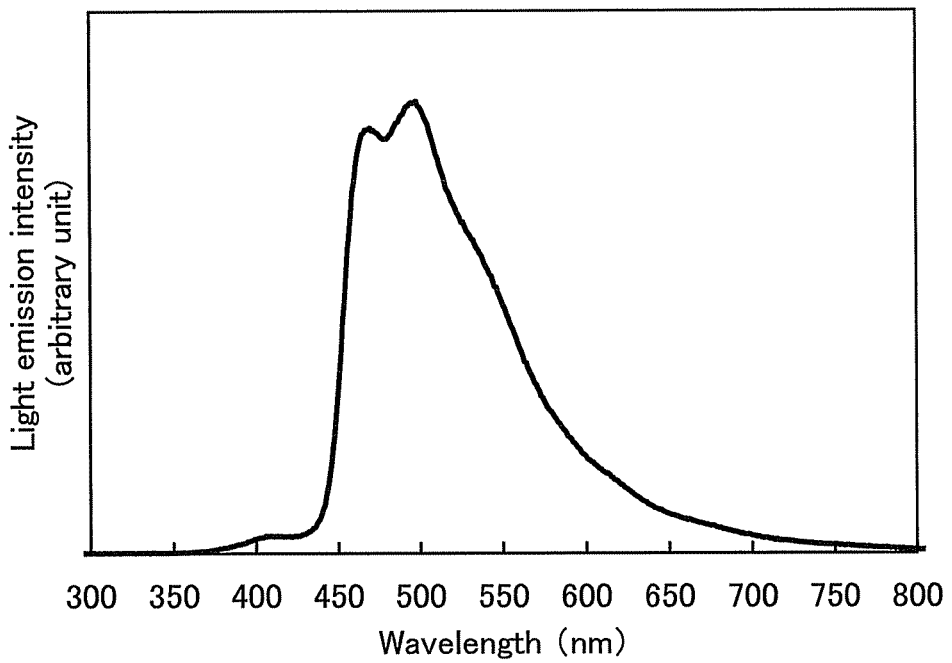
FIG. 14 shows an emission spectrum of Light-emitting Element 1.

FIG. 11 shows current density vs. luminance characteristics of Light-emitting Element 1. FIG. 12 shows voltage vs. luminance characteristics thereof. FIG. 13 shows luminance vs. current efficiency characteristics thereof. FIG. 14 shows an emission spectrum thereof measured at a current of 1 mA. From FIG. 14, it is found that the light emission from Light-emitting Element 1 originates from [Ir(MCF$_2$ptz)$_2$(pic)]. The CIE chromaticity coordinates of Light-emitting Element 1 at a luminance of 106 cd/m$^2$ are (x, y)=(0.24, 0.37), and light-blue light was emitted. From FIG. 13, it is found that the current efficiency of Light-emitting Element 1 at 106 cd/m$^2$ is 4.2 cd/A. From FIG. 12, it is found that the driving voltage at 106 cd/m$^2$ is 5.4 V and that the power efficiency is 2.5 lm/W.

Example 5

In this example, a light-emitting element using the organometallic complex bis(3,4-diphenyl-5-trifluoromethyl-4H-1,2,4-triazolato)(picolinato)iridium(III) (abbreviation: [Ir(CF$_3$ptz)$_2$(pic)]), which is represented by Structural Formula (100) in Embodiment 1, is described (the light-emitting element is referred to as Light-emitting Element 2 below). Structural formulas of part of materials used in this example are shown below.

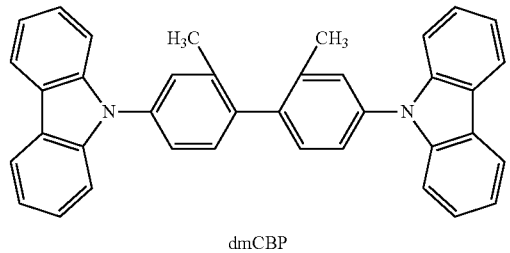 [SMILES: Cc1cc(-n2c3ccccc3c3ccccc32)ccc1-c1ccc(-n2c3ccccc3c3ccccc32)cc1C]

dmCBP (Light Emitting Element 2)

First, indium tin oxide containing silicon was deposited over a glass substrate by a sputtering method, so that a first electrode which functions as an anode was formed. The thickness of the first electrode was 110 nm and the electrode area was 2 mm×2 mm.

Next, the glass substrate over which the first electrode was formed was fixed to a substrate holder provided in a vacuum evaporation apparatus such that the side on which the first electrode was formed faced downward, and the pressure was reduced to approximately 10$^{-4}$ Pa. After that, over the first electrode, a layer containing a composite material of an organic compound and an inorganic compound was formed by co-evaporation of 4,4',4''-tris(N-carbazolyl)triphenylamine (abbreviation: TCTA) and molybdenum(VI) oxide. The thickness of the layer containing a composite material was 40 nm, and the weight ratio of TCTA and molybdenum oxide was adjusted to 2:1 (=TCTA:molybdenum oxide).

Next, a 20-nm-thick TCTA layer was formed over the layer containing a composite material by an evaporation method using resistance heating, so that a hole-transport layer was formed.

Further, a 30-nm-thick light-emitting layer was formed over the hole-transport layer by co-evaporation of 4,4'-bis(9-carbazol)-2,2'-dimethyl-biphenyl (abbreviation: dmCBP) and [Ir(CF$_3$ptz)$_2$(pic)], which is the organometallic complex represented by Structural Formula (100) in Embodiment 1. Here, the weight ratio of dmCBP and [Ir(CF$_3$ptz)$_2$(pic)] was adjusted to 1:0.03 (=dmCBP:[Ir(CF$_3$ptz)$_2$(pic)]).

After that, over the light-emitting layer, a 10-nm-thick 3-(4-tert-butylphenyl)-4-phenyl-5-(4-biphenylyl)-1,2,4-triazole (abbreviation: TAZ 01) layer was formed by an evaporation method using resistance heating, so that an electron-transport layer was formed.

Furthermore, a 20-nm-thick electron-injection layer was formed over the electron-transport layer by co-evaporation of TAZ 01 and lithium. Here, the weight ratio of TAZ 01 and lithium was adjusted to 1:0.02 (=TAZ 01:lithium).

Lastly, a 200-nm-thick aluminum layer was formed over the electron-injection layer by an evaporation method using resistance heating, so that a second electrode which functions as a cathode was formed. Through the above process, Light-emitting Element 2 was fabricated.

Figure 15:
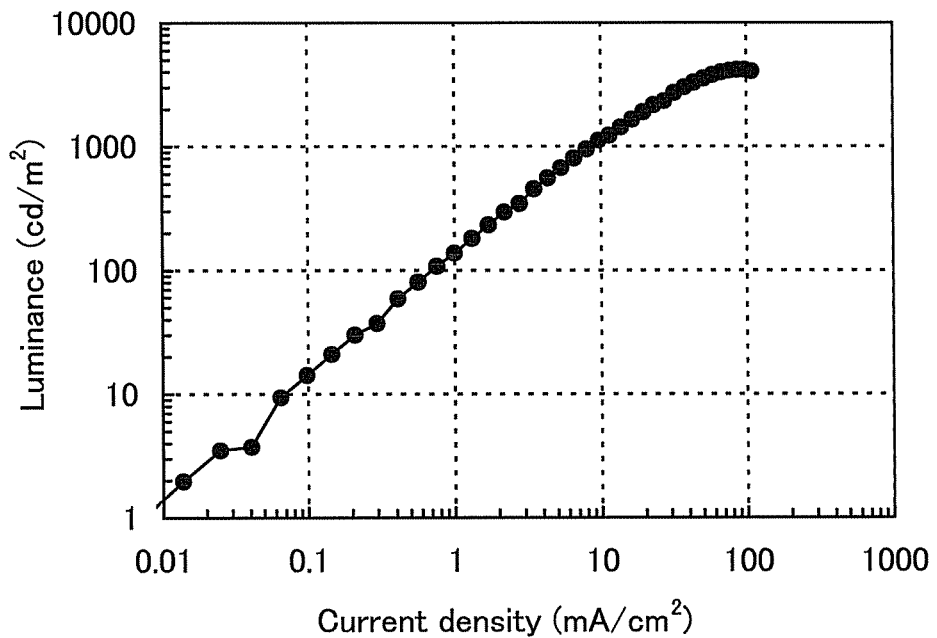
FIG. 15 shows current density vs. luminance characteristics of Light-emitting Element 2.
Figure 16:
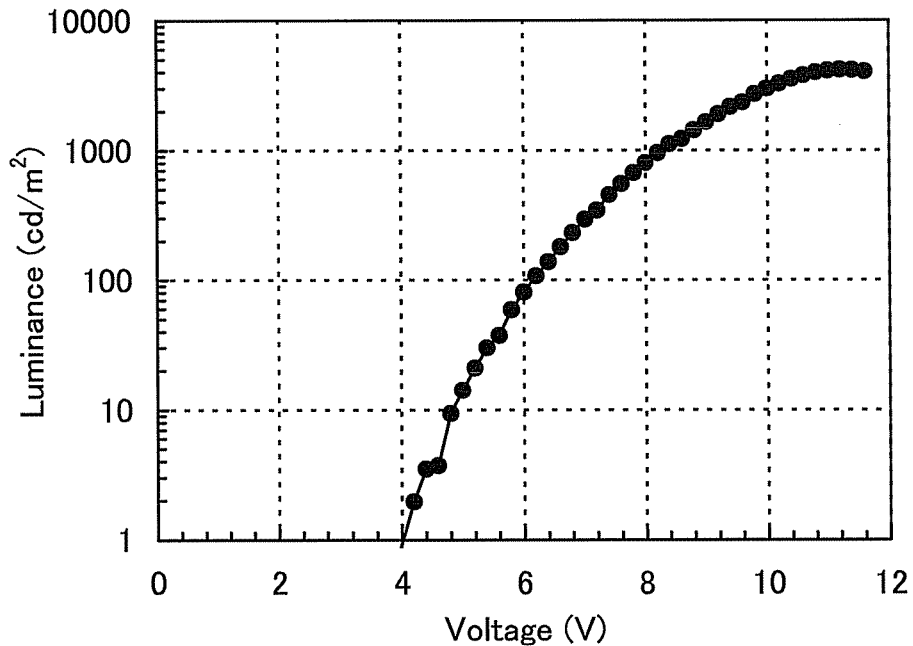
FIG. 16 shows voltage vs. luminance characteristics of Light-emitting Element 2.
Figure 17:
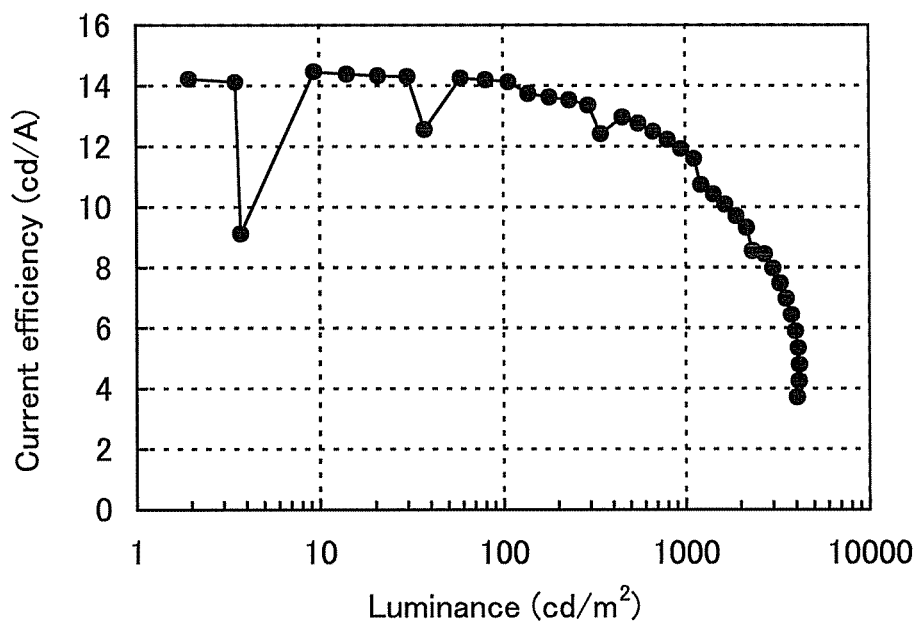
FIG. 17 shows luminance vs. current efficiency characteristics of Light-emitting Element 2.
Figure 18:
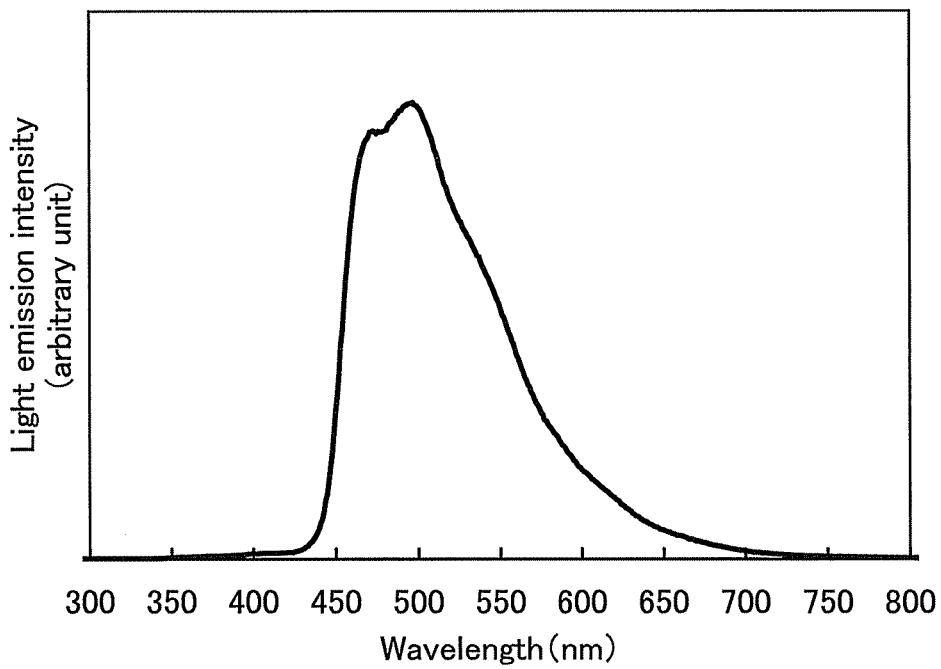
FIG. 18 shows an emission spectrum of Light-emitting Element 2.

FIG. 15 shows current density vs. luminance characteristics of Light-emitting Element 2. FIG. 16 shows voltage vs. luminance characteristics thereof. FIG. 17 shows luminance vs. current efficiency characteristics thereof. Further, FIG. 18 shows an emission spectrum thereof at a current of 1 mA. From FIG. 18, it is found that the light emission from Light-emitting Element 2 originates from [Ir(CF$_3$ptz)$_2$(pic)]. The CIE chromaticity coordinates of Light-emitting Element 2 at a luminance of 951 cd/m$^2$ are (x, y)=(0.23, 0.38), and light-blue light was emitted. From FIG. 17, it is found that the current efficiency of Light-emitting Element 2 at 951 cd/m$^2$ is 11.9 cd/A, which is a high current efficiency. From FIG. 16, it is found that the driving voltage at 951 cd/m² is 8.2 V and that the power efficiency is 4.6 lm/W. These results indicate that Light-emitting Element 2 needs a low voltage for obtaining a certain luminance, has low power consumption, and has high current efficiency.

Example 6

In this example, a light-emitting element using the organometallic complex tris[3-(4-fluorophenyl)-4-phenyl-5-trifluoromethyl-4H-1,2,4-triazolato]iridium(III) (abbreviation: [Ir(CF₃Fptz)₃]), which is represented by Structural Formula (155) in Embodiment 1, is described (the light-emitting element is referred to as Light-emitting Element 3 below).
(Light-Emitting Element 3)

First, indium tin oxide containing silicon was deposited over a glass substrate by a sputtering method, so that a first electrode which functions as an anode was formed. The thickness of the first electrode was 110 nm and the electrode area was 2 mm×2 mm.

Next, the glass substrate over which the first electrode was formed was fixed to a substrate holder provided in a vacuum evaporation apparatus such that the side on which the first electrode was formed faced downward, and the pressure was reduced to approximately $10^{-4}$ Pa. After that, over the first electrode, a layer containing a composite material of an organic compound and an inorganic compound was formed by co-evaporation of 4,4'-di(N-carbazolyl)biphenyl (abbreviation: CBP) and molybdenum(VI) oxide. The thickness of the layer containing a composite material was 50 nm, and the weight ratio of CBP and molybdenum oxide was adjusted to 2:1 (=CBP:molybdenum oxide).

Next, a 10-nm-thick 4,4'-bis(9-carbazol)-2,2'-dimethyl-biphenyl (abbreviation: dmCBP) layer was formed over the layer containing a composite material by an evaporation method using resistance heating, so that a hole-transport layer was formed.

Next, a 40-nm-thick light-emitting layer was formed over the hole-transport layer by co-evaporation of 9-[4-(4,5-diphenyl-4H-1,2,4-triazol-3-yl)phenyl]-9H-carbazole (abbreviation: CzTAZ I) and [Ir(CF₃Fptz)₃], which is the organometallic complex represented by Structural Formula (155) in Embodiment 1. Here, the weight ratio of CzTAZ I and [Ir(CF₃Fptz)₃] was adjusted to 1:0.06 (=CzTAZ I:[Ir(CF₃Fptz)₃]).

After that, over the light-emitting layer, a 10-nm-thick CzTAZ I layer was formed by an evaporation method using resistance heating, and then a 15-nm-thick bathophenanthroline (abbreviation: BPhen) layer was formed over the CzTAZ I layer by an evaporation method using resistance heating. In such a manner, an electron-transport layer in which a layer formed using CzTAZ I and a layer formed using BPhen were stacked was formed over the light-emitting layer.

Furthermore, a 1-nm-thick lithium fluoride layer was formed over the electron-transport layer by an evaporation method using resistance heating, so that an electron-injection layer was formed.

Lastly, a 200-nm-thick aluminum layer was formed over the electron-injection layer by an evaporation method using resistance heating, so that a second electrode which functions as a cathode was formed. Through the above process, Light-emitting Element 3 was fabricated.

Figure 23:
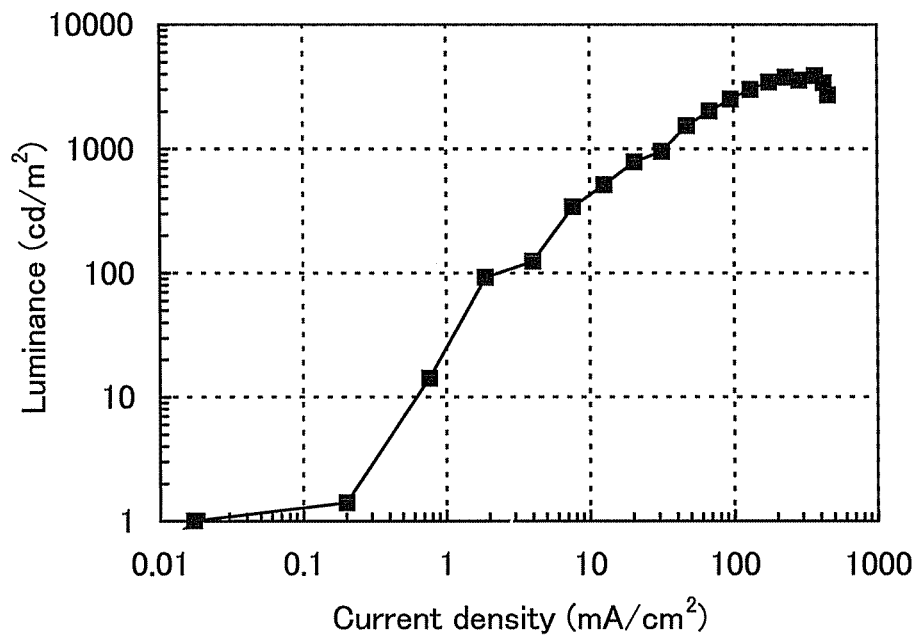
FIG. 23 shows current density vs. luminance characteristics of Light-emitting Element 3.
Figure 24:
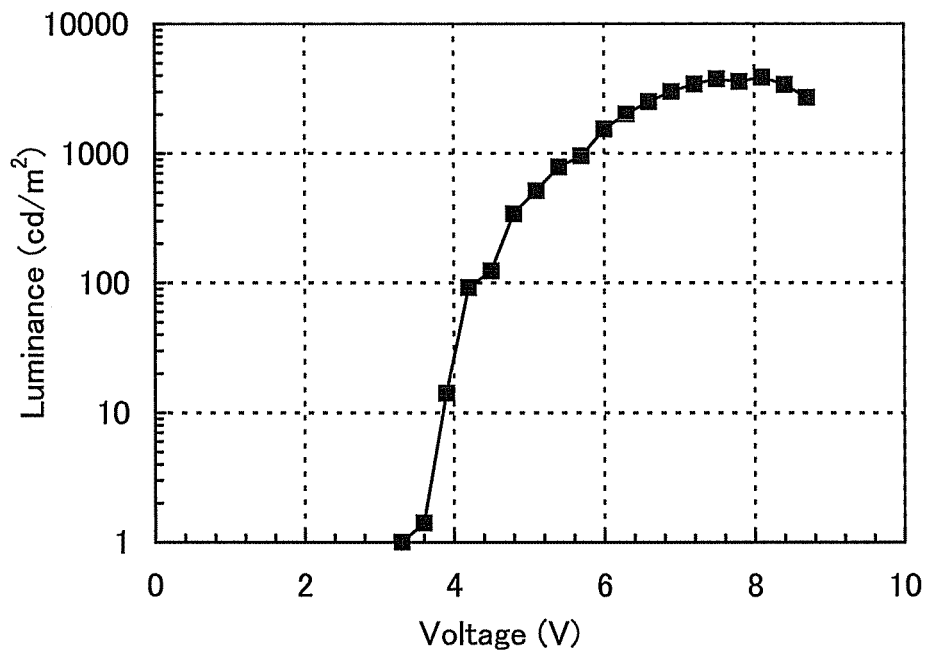
FIG. 24 shows voltage vs. luminance characteristics of Light-emitting Element 3.
Figure 25:
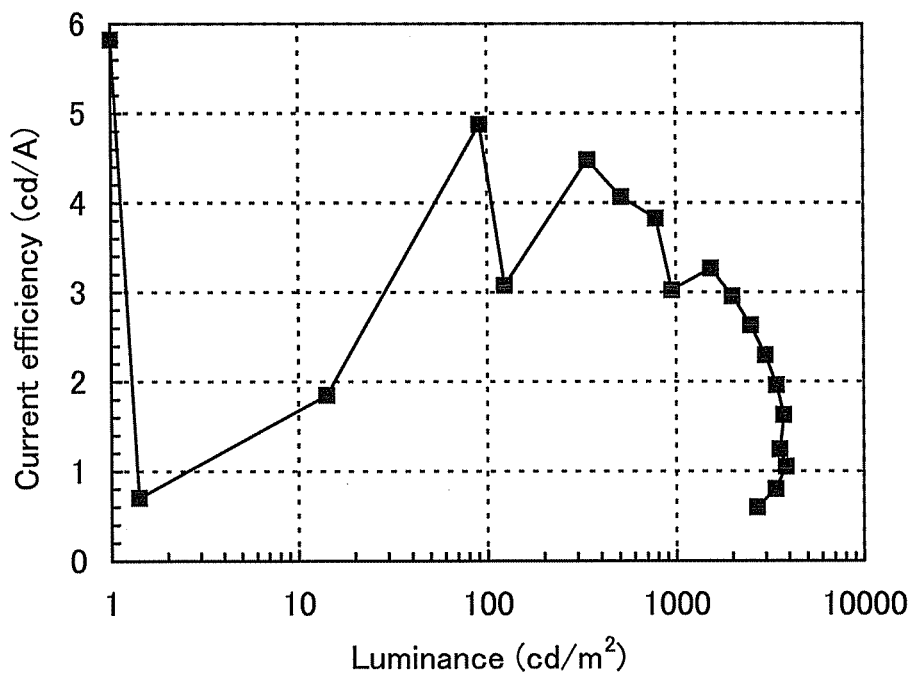
FIG. 25 shows luminance vs. current efficiency characteristics of Light-emitting Element 3.
Figure 26:
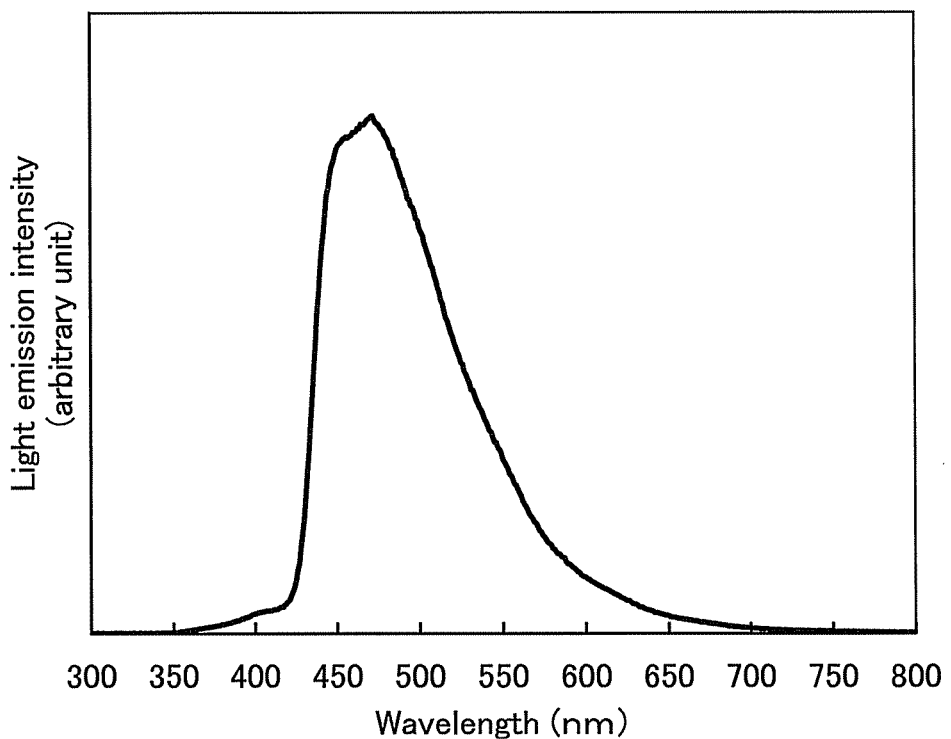
FIG. 26 shows an emission spectrum of Light-emitting Element 3.

FIG. 23 shows current density vs. luminance characteristics of Light-emitting Element 3. FIG. 24 shows voltage vs. luminance characteristics thereof. FIG. 25 shows luminance vs. current efficiency characteristics thereof. FIG. 26 shows an emission spectrum thereof measured at a current of 1 mA. From FIG. 26, it is found that the light emission from Light-emitting Element 3 originates from [Ir(CF₃Fptz)₃]. The CIE chromaticity coordinates of Light-emitting Element 3 at a luminance of 92 cd/m² are (x, y)=(0.18, 0.24), and light-blue light was emitted. From FIG. 25, it is found that the current efficiency of Light-emitting Element 3 at 92 cd/m² is 4.9 cd/A, which is a high current efficiency. From FIG. 24, it is found that the driving voltage at 92 cd/m² is 4.2 V and that the power efficiency is 3.6 lm/W. These results indicate that Light-emitting Element 3 needs a low voltage for obtaining a certain luminance, has low power consumption, and has a high current efficiency.

Comparative Example 1

In this comparative example, a synthesis method of an organometallic complex bis(3,4-diphenyl-4H-1,2,4-triazolato)(picolinato)iridium(III) (abbreviation: [Ir(ptz)₂(pic)]) is described. Note that a structure of [Ir(ptz)₂(pic)] is shown below.

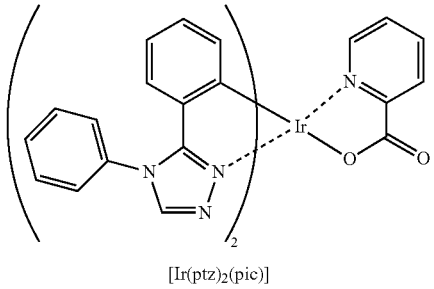

[Ir(ptz)₂(pic)]

Step 1: Synthesis of di-µ-chloro-bis[bis(3,4-diphenyl-4H-1,2,4-triazolato)]iridium(III) (abbreviation: [Ir(ptz)₂Cl]₂)

First, 15 mL of 2-ethoxyethanol, 5 mL of water, 1.77 g of a ligand 3,4-diphenyl-4H-1,2,4-triazole (abbreviation: Hptz), and 0.597 g of iridium chloride hydrate (IrCl₃.H₂O) were put in a recovery flask provided with a reflux pipe, and the air in the flask was replaced by argon. Then, irradiation with microwaves (2.45 GHz, 100 W) for 30 minutes was performed to cause reaction. The reacted solution was filtered and the obtained powder was washed with ethanol, so that a binuclear complex [Ir(ptz)₂Cl]₂ was prepared (yellow powder, yield: 43%). Note that the irradiation with microwaves was performed using a microwave synthesis system (Discover manufactured by CEM Corporation). The synthetic scheme of Step 1 is shown by (a-4).

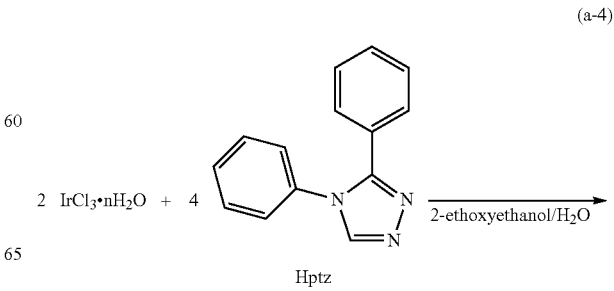

(a-4)

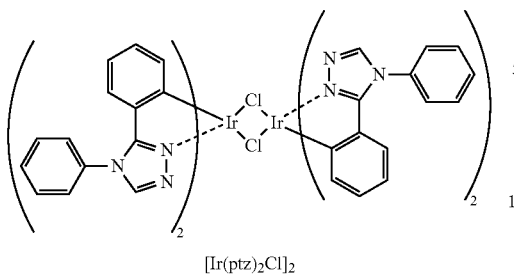

[Ir(ptz)₂Cl]₂

Step 2: Synthesis of bis(3,4-diphenyl-4H-1,2,4-triazolato)(picolinato)iridium(III) (abbreviation: [Ir(ptz)₂(pic)])

Next, 15 mL of dichloromethane, 1.14 g of the binuclear complex [Ir(ptz)₂Cl]₂ prepared in Step 1, 0.985 g of picolinic acid, and 0.848 g of sodium carbonate were put in a recovery flask provided with a reflux pipe, and the air in the flask was replaced by argon. Then, irradiation with microwaves (2.45 GHz, 100 W) for 60 minutes was performed to cause reaction. Although purification of the reacted solution was attempted, the objective iridium complex was not prepared. The synthetic scheme of Step 2 is shown by (b-4).

(b-4)

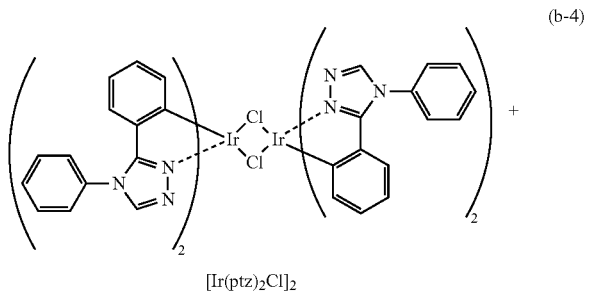

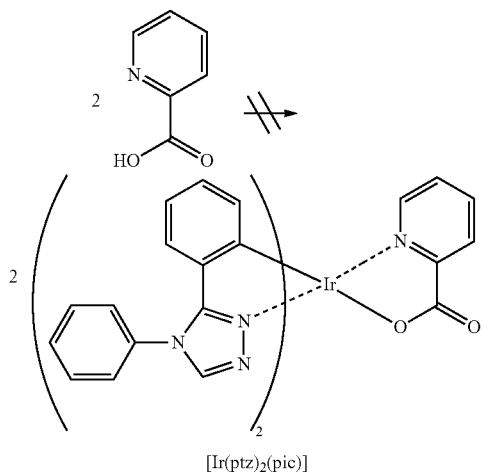

[Ir(ptz)₂(pic)]

As described in this comparative example, the synthesis of [Ir(ptz)₂(pic)] was difficult. Thus, it is found that as compared with the organometallic complexes which are described in Example 1, Example 2, and Example 3 and each of which is one embodiment of the present invention, a substance where a substituent bonded to the fifth position of a triazole ring is hydrogen has an extremely low yield or cannot be synthesized. That is, decomposition reaction can be suppressed in the synthesis of the organometallic complex which is one embodiment of the present invention; therefore, the yield of the synthesis is drastically improved as compared with [Ir(ptz)₂(pic)].

Comparative Example 2

In this comparative example, a synthesis example of an organometallic complex bis[4-(4-tert-butylphenyl)-3,5-diphenyl-4H-1,2,4-triazolato](picolinato)iridium(III) (abbreviation: [Ir(taz-tBuP)₂(pic)]) represented by a structural formula below is specifically described.

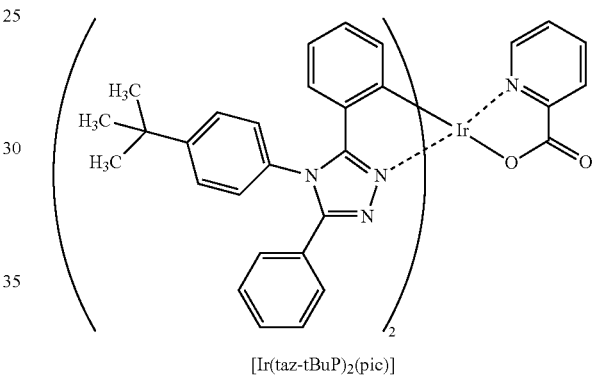

[Ir(taz-tBuP)₂(pic)]

Step 1: Synthesis of di-μ-chloro-bis[bis{4-(4-tert-butylphenyl)-3,5-diphenyl-4H-1,2,4-triazolato}]iridium(III) (abbreviation: [Ir(taz-tBuP)₂Cl]₂)

First, 15 mL of 2-ethoxyethanol, 5 mL of water, 1.71 g of a ligand 4-(4-tert-butylphenyl)-3,5-diphenyl-4H-1,2,4-triazole (abbreviation: Htaz-tBuP), and 0.58 g of iridium chloride hydrate (IrCl₃.H₂O) (manufactured by Sigma-Aldrich Corp.) were put in a recovery flask provided with a reflux pipe, and the air in the flask was replaced by argon. Then, irradiation with microwaves (2.45 GHz, 100 W) for 30 minutes was performed to cause reaction. Note that the irradiation with microwaves in this comparative example was performed using a microwave synthesis system (Discover manufactured by CEM Corporation). Then, the reacted solution was filtered, and the filtrate was concentrated and dried. The obtained residue was dissolved in ethyl acetate and filtration was performed to remove insoluble matter. The obtained filtrate was concentrated and dried, so that the binuclear complex [Ir(taz-tBuP)₂Cl]₂ was prepared (yellow powder, yield: 100%). The synthetic scheme of Step 1 is shown by (a-5).

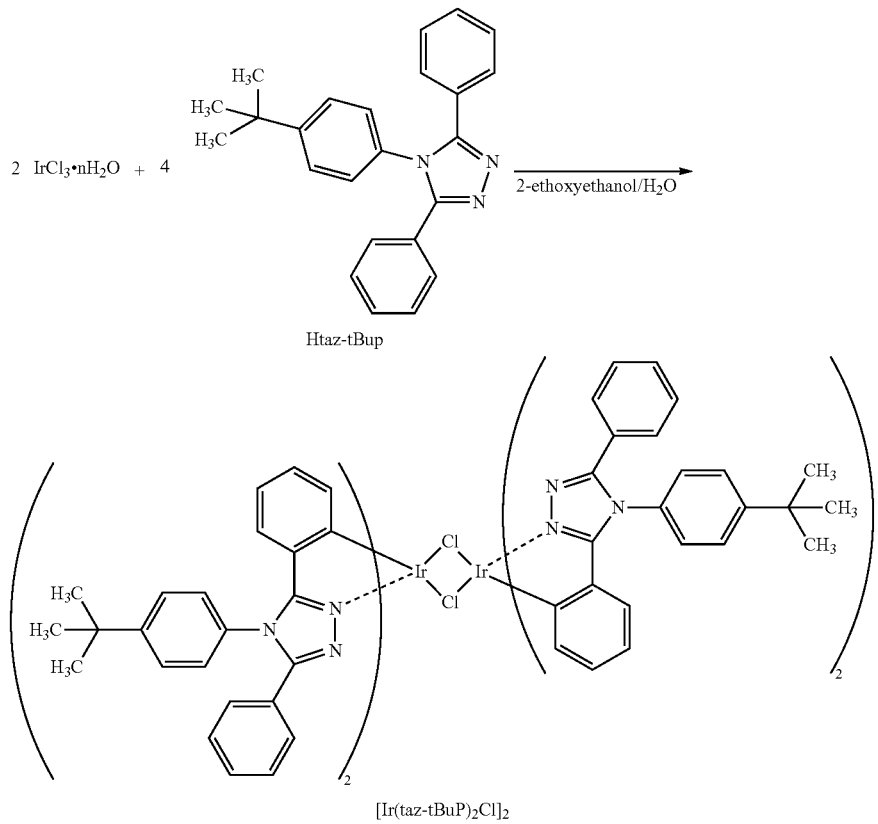

(a-5)

Step 2: Synthesis of bis[4-(4-tert-butylphenyl)-3,5-diphenyl-4H-1,2,4-triazolato](picolinato)iridium(III) (abbreviation: [Ir(taz-tBuP)$_2$(pic)])

Further, 15 mL of dichloromethane, 1.78 g of the binuclear complex [Ir(taz-tBuP)$_2$Cl]$_2$ prepared in Step 1, 0.94 g of picolinic acid, and 1 g of sodium carbonate were put in a recovery flask provided with a reflux pipe, and the air in the flask was replaced by argon. Then, irradiation with microwaves (2.45 GHz, 100 W) for 30 minutes was performed to cause reaction. The reacted solution was filtered. The obtained residue was dissolved in dichloromethane and filtration was performed to remove insoluble matter, and then the filtrate was concentrated and dried. The obtained residue was purified by silica gel column chromatography which uses ethyl acetate as a developing solvent. Further, recrystallization was performed with a methanol solvent, so that the organometallic complex [Ir(taz-tBuP)$_2$(pic)] which is a comparative example was prepared (yellow powder, yield: 19%). The synthetic scheme of Step 2 is shown by (b-5).

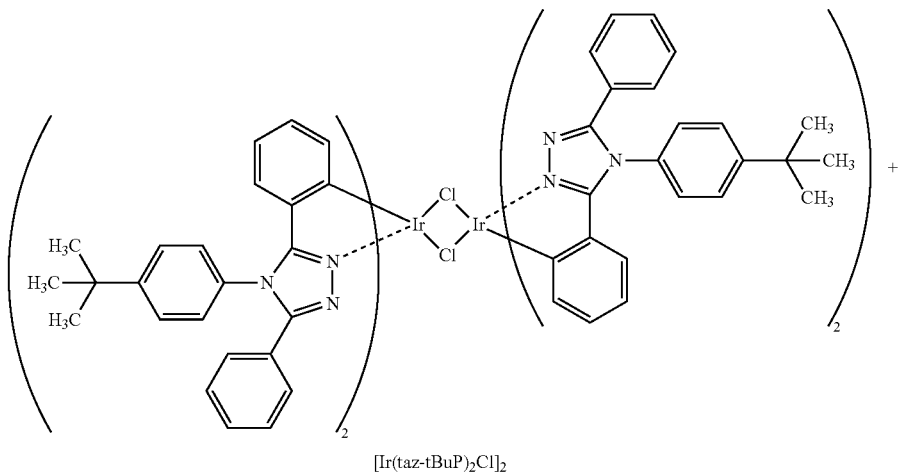

(b-5)

-continued

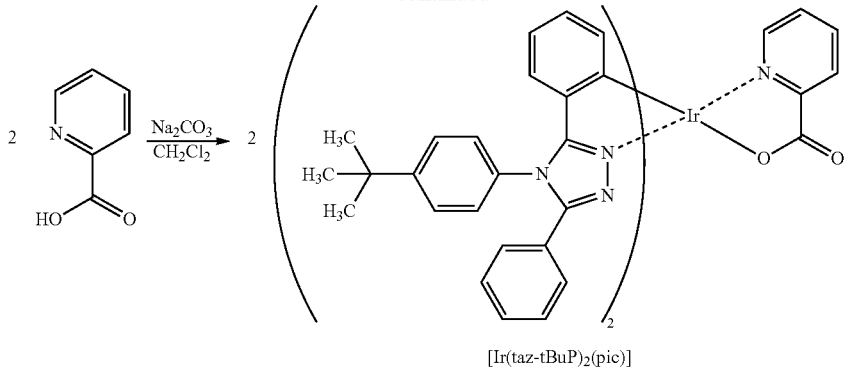

[Ir(taz-tBuP)₂(pic)]

Figure 19:
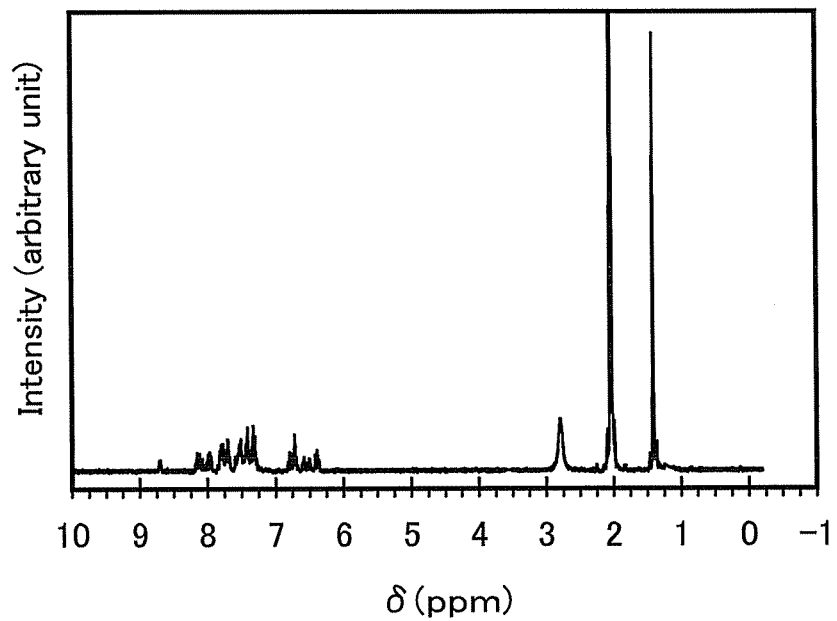
FIG. 19 shows a $^1$H-NMR spectrum of [Ir(taz-tBuP)$_2$(pic)] which is a comparative example.

An analysis result by nuclear magnetic resonance spectroscopy ($^1$H-NMR) of the yellow powder prepared in Step 2 is shown below. The $^1$H-NMR spectrum is shown in FIG. 19. From the results, it is found that [Ir(taz-tBuP)₂(pic)] was prepared by the synthesis method shown in this comparative example.

$^1$H-NMR. δ (acetylacetone-d₆): 1.42 (s, 18H), 6.39 (t, 2H), 6.51 (t, 1H), 6.58 (t, 1H), 6.72 (m, 3H), 7.23-7.59 (m, 12H), 7.68-7.80 (m, 6H), 7.95-8.15 (m, 4H), 8.70 (s, 1H).

Figure 20:
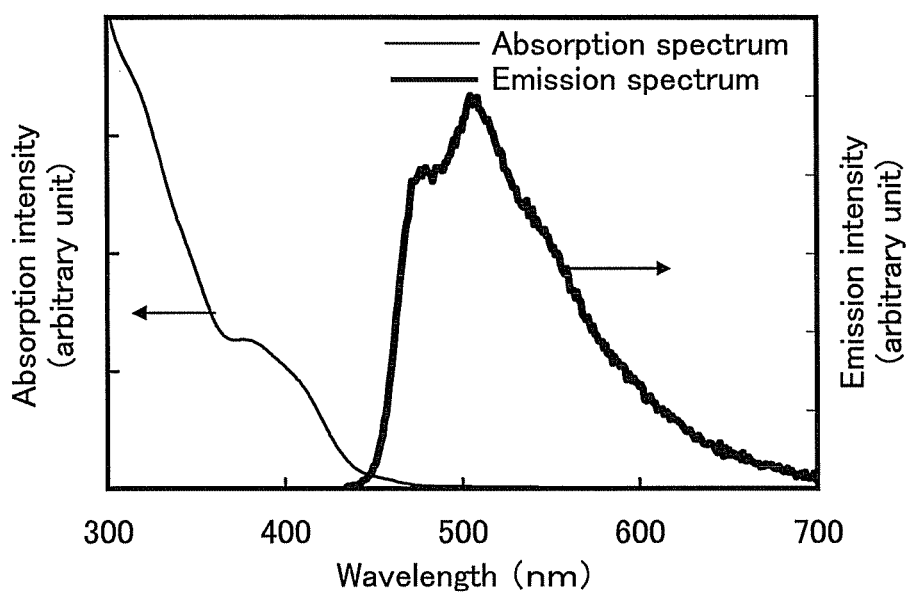
FIG. 20 shows an absorption spectrum and an emission spectrum of [Ir(taz-tBuP)$_2$(pic)] which is a comparative example in a dichloromethane solution.

Next, an ultraviolet-visible absorption spectrum (an absorption spectrum) and an emission spectrum of [Ir(taz-tBuP)₂(pic)] in dichloromethane solutions were measured. The absorption spectrum was measured with the use of an ultraviolet-visible light spectrophotometer (V-550 manufactured by JASCO Corporation) in the state where a dichloromethane solution (0.055 mmol/L) was put in a quartz cell at room temperature. The emission spectrum was measured with the use of a fluorescence spectrophotometer (FS920 manufactured by Hamamatsu Photonics Corporation) in the state where a degassed dichloromethane solution (0.33 mmol/L) was put in a quartz cell at room temperature. FIG. 20 shows measurement results of the absorption spectrum and emission spectrum. The horizontal axis represents wavelength, and the vertical axis represents absorption intensity and emission intensity. In FIG. 20, two solid lines are shown; a thin line represents the absorption spectrum, and a thick line represents the emission spectrum. Note that the absorption spectrum in FIG. 20 is a result obtained by subtraction of the absorption spectrum of only dichloromethane that was put in a quartz cell from a measured absorption spectrum of the dichloromethane solution (0.055 mmol/L) in a quartz cell.

As shown in FIG. 20, the organometallic complex [Ir(taz-tBuP)₂(pic)] which is a comparative example of the present invention has peaks of emission at 480 nm and 508 nm, and blue-green light was observed from the dichloromethane solution.

The wavelengths of the peaks of emission of [Ir(taz-tBuP)₂(pic)] described in this comparative example are longer than those of [Ir(MCF₂ptz)₂(pic)] described in Example 1, [Ir(CF₃ptz)₂(pic)] described in Example 2, and [Ir(CF₃Fptz)₃] described in Example 3. Thus, it is found that the emission spectrum of a substance where a substituent bonded to the fifth position of a triazole ring is a phenyl group shifts to a long wavelength side as compared with a substance where the substituent bonded to the fifth position of a triazole ring is a haloalkyl group. That is, an organometallic complex which is one embodiment of the present invention where a substituent bonded to the fifth position of a triazole ring is a haloalkyl group having 1 to 9 carbon atoms which may have a substituent has a peak of emission on a short wavelength side as compared with an organometallic complex where a substituent bonded to the fifth position of a triazole ring is a phenyl group. Therefore, the organometallic complex which is one embodiment of the present invention is advantageous in manufacture of a material that exhibits phosphorescence having a wavelength band of blue as compared with [Ir(taz-tBuP)₂ (pic)].

This application is based on Japanese Patent Application serial no. 2010-058184 filed with Japan Patent Office on Mar. 15, 2010, the entire contents of which are hereby incorporated by reference.

What is claimed is:
1. An organometallic complex represented by formula (100),

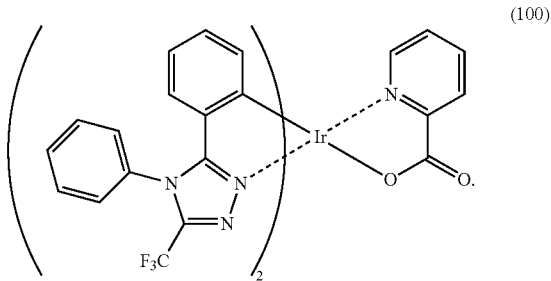

(100)

2. An organometallic complex represented by formula (108),

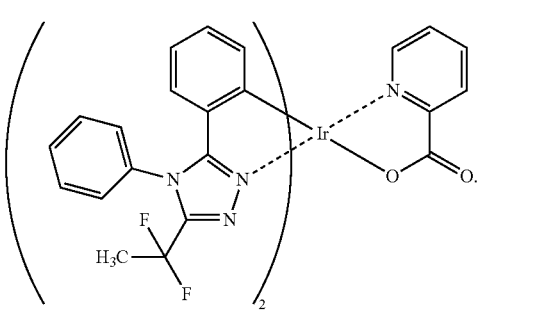

(108)

3. An organometallic complex represented by formula (155),

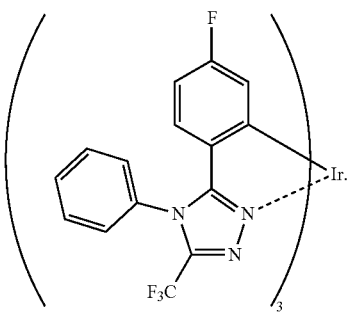

(155)

4. A light-emitting element comprising the organometallic complex according to claim 1 between a pair of electrodes.

5. A light-emitting element comprising the organometallic complex according to claim 2 between a pair of electrodes.

6. A light-emitting element comprising the organometallic complex according to claim 3 between a pair of electrodes.

7. A light-emitting element comprising:
a pair of electrodes;
a first light-emitting unit containing the organometallic complex according to claim 1; and
a second light-emitting unit containing a light-emitting material that emits light with a longer wavelength than the organometallic complex,
wherein the first light-emitting unit and the second light-emitting unit are located between the pair of electrodes.

8. A light-emitting element comprising:
a pair of electrodes;
a first light-emitting unit containing the organometallic complex according to claim 2; and
a second light-emitting unit containing a light-emitting material that emits light with a longer wavelength than the organometallic complex,
wherein the first light-emitting unit and the second light-emitting unit are located between the pair of electrodes.

9. A light-emitting element comprising:
a pair of electrodes;
a first light-emitting unit containing the organometallic complex according to claim 3; and
a second light-emitting unit containing a light-emitting material that emits light with a longer wavelength than the organometallic complex,
wherein the first light-emitting unit and the second light-emitting unit are located between the pair of electrodes.

10. A light-emitting element comprising:
a pair of electrodes;
a first light-emitting unit containing the organometallic complex according to claim 1;
a second light-emitting unit containing a first light-emitting material that emits light with a longer wavelength than the organometallic complex; and
a third light-emitting unit containing a second light-emitting material that emits light with a longer wavelength than the organometallic complex and a shorter wavelength than the first light-emitting material,
wherein the first light-emitting unit, the second light-emitting unit, and the third light-emitting unit are located between the pair of electrodes.

11. A light-emitting element comprising:
a pair of electrodes;
a first light-emitting unit containing the organometallic complex according to claim 2;
a second light-emitting unit containing a first light-emitting material that emits light with a longer wavelength than the organometallic complex; and
a third light-emitting unit containing a second light-emitting material that emits light with a longer wavelength than the organometallic complex and a shorter wavelength than the first light-emitting material,
wherein the first light-emitting unit, the second light-emitting unit, and the third light-emitting unit are located between the pair of electrodes.

12. A light-emitting element comprising:
a pair of electrodes;
a first light-emitting unit containing the organometallic complex according to claim 3;
a second light-emitting unit containing a first light-emitting material that emits light with a longer wavelength than the organometallic complex; and
a third light-emitting unit containing a second light-emitting material that emits light with a longer wavelength than the organometallic complex and a shorter wavelength than the first light-emitting material,
wherein the first light-emitting unit, the second light-emitting unit, and the third light-emitting unit are located between the pair of electrodes.

13. A lighting device comprising the organometallic complex according to claim 1 in a light-emitting component.

14. A lighting device comprising the organometallic complex according to claim 2 in a light-emitting component.

15. A lighting device comprising the organometallic complex according to claim 3 in a light-emitting component.

16. A display device comprising the organometallic complex according to claim 1 in a light-emitting component.

17. A display device comprising the organometallic complex according to claim 2 in a light-emitting component.

18. A display device comprising the organometallic complex according to claim 3 in a light-emitting component.

* * * * *